(12) United States Patent
Bestel-Corre et al.

(10) Patent No.: US 8,795,990 B2
(45) Date of Patent: Aug. 5, 2014

(54) RECOMBINANT ENZYME WITH ALTERED FEEDBACK SENSITIVITY

(75) Inventors: Gwénaëlle Bestel-Corre, Saint Bauzire (FR); Michel Chateau, Riom (FR); Rainer Figge, Riom (FR); Céline Raynaud, Dallet (FR); Philippe Soucaille, Deyme (FR)

(73) Assignee: Metabolic Explorer (FR)

( * ) Notice: Subject to any disclaimer, the term of this patent is extended or adjusted under 35 U.S.C. 154(b) by 1228 days.

(21) Appl. No.: 11/579,907

(22) PCT Filed: May 12, 2005

(86) PCT No.: PCT/EP2005/052180
§ 371 (c)(1),
(2), (4) Date: Dec. 28, 2006

(87) PCT Pub. No.: WO2005/108561
PCT Pub. Date: Nov. 17, 2005

(65) Prior Publication Data
US 2009/0029424 A1    Jan. 29, 2009

(30) Foreign Application Priority Data
May 12, 2004    (WO) .................. PCT/IB2004/001901

(51) Int. Cl.
*C12P 13/04*    (2006.01)
*C12P 13/12*    (2006.01)

(52) U.S. Cl.
USPC ......................... 435/113; 435/69.1; 435/106

(58) Field of Classification Search
None
See application file for complete search history.

(56) References Cited

U.S. PATENT DOCUMENTS 7,611,873 B1 *  11/2009  Usuda et al. .................. 435/113

FOREIGN PATENT DOCUMENTS

| JP | 2000139471 | 5/2000 |
|---|---|---|
| WO | 2004/038013 A2 | 5/2004 |

OTHER PUBLICATIONS

Ngo et al. in the Protein Folding Problem and Tertiary Structure Prediction, 1994, Merz et al. (ed.), Birkhauser, Boston, MA, pp. 433 and 492-495.*
Chattopadhyay M. K. et al., "Control of Methionine Biosynthesis in *Escherichia-coli* K12 A Closer Study with Analogue-Resistant Mutants", Journal of General Microbiology, vol. 137, No. 3, 1991, pp. 685-692.
Database USPTO Proteins 'Online!, Dec. 18, 2003, "Sequence 8623 from patent US 6610836".
Database Geneseq 'Online!, Nov. 20, 2003, "Photorhabdus luminescens protein sequence #2067".
Kumar D. et al., "Production of methionine by a multi-analogue resistant mutant of *Corynebacterium ilium*", Process Biochemistry, vol. 38, No. 8, Mar. 28, 2003, pp. 1165-1171.
Reczkowski, R.S. et al., "Structural and Functional Roles of Cysteine 90 and Cysteine 240 in *S*-Adenosylmethionine Synthetase," *The Journal of Biological Chemistry*, Aug. 4, 1995, vol. 270, No. 31, pp. 18484-18490.

* cited by examiner

*Primary Examiner* — Richard Hutson
(74) *Attorney, Agent, or Firm* — DLA Piper LLP (US)

(57) ABSTRACT

The present invention relates to the use of recombinant homoserine transsuccinylase enzymes with altered feedback sensitivity (MetA*) and possibly recombinant S-adenosyl methionine synthetase enzymes with reduced activity (MetK*) for the production of methionine, its precursors or derivatives thereof.

5 Claims, 9 Drawing Sheets

Figure 3A:
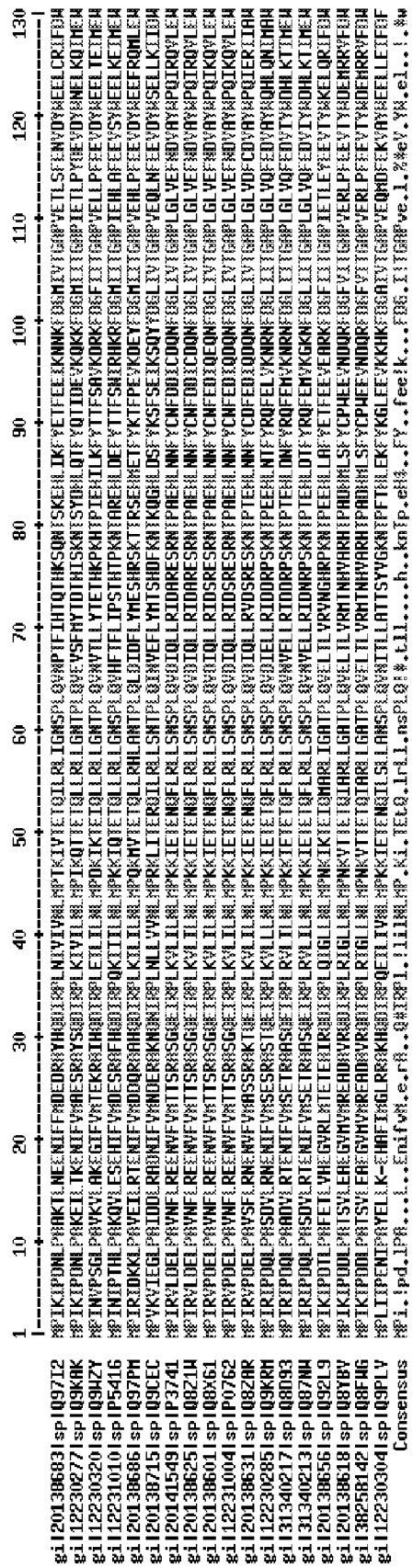

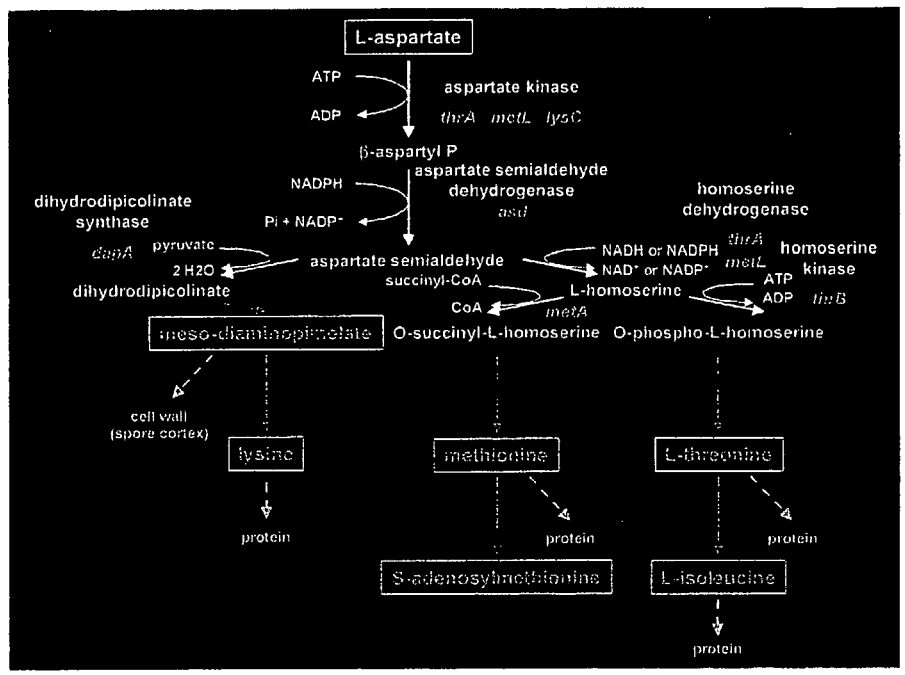
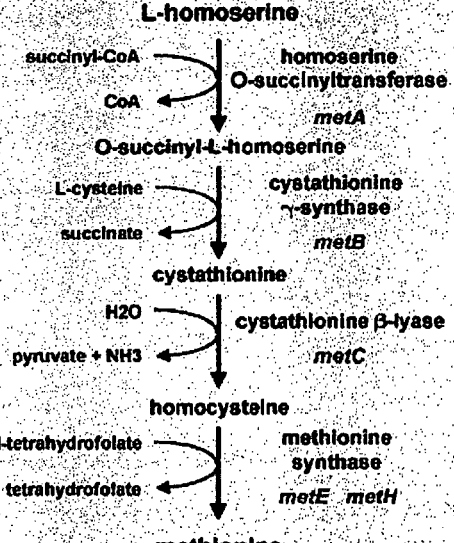
Fig.1A/B

```
                        1                                                  50
        metA      (1)   MPIRVPDELPAVNFLREENVFVMTTSRASGQEIRPLKVLILNLMPKKIET
metA11/metA12     (1)   MPIRVPDELPAVNFLREENVFVMTTSRASGQEIRPLKVLILNLMPKKIET
      metA13      (1)   MPIRVPDELPAVNFLREENVFVMTTSRASGQEIRPLKVLILNLMPKKIET
      metA14      (1)   MPIRVPDELPAVNFLREENVFVMTTSRVSGQEIRPLKVLILNLMPKKIET
   Consensus      (1)   MPIRVPDELPAVNFLREENVFVMTTSRASGQEIRPLKVLILNLMPKKIET
                        51                                                100
        metA     (51)   ENQFLRLLSNSPLQVDIQLLRIDSRESRNTPAEHLNNFYCNFEDIQDQNF
metA11/metA12    (51)   ENQFLRLLSNSPLEVDIQLLRIDSRESRNTPAEHLNNFYCNFEDIQDQNF
      metA13     (51)   ENQFLRLLSNSPFQVDIQLLRIDSRESRNTPAEHLNNFYCNFEDIQDQNF
      metA14     (51)   ENQFLRLLSNSPLQVDIQLLRIDSRESRNTPAEHLNNFYCNFEDIQDQNF
   Consensus     (51)   ENQFLRLLSNSPLQVDIQLLRIDSRESRNTPAEHLNNFYCNFEDIQDQNF
                        101                                               150
        metA    (101)   DGLIVTGAPLGLVEFNDVAYWPQIKQVLEWSKDHVTSTLFVCWAVQAALN
metA11/metA12   (101)   DGLIVTGAPLGLVEFNDVAYWPQIKQVLEWSKDHVTSTLFVCWAVQAALN
      metA13    (101)   DGLIVTGAPLGLVEFNDVAYWPQIKQVLEWSKDHVTSTLFVCWAVQAALN
      metA14    (101)   DGLIVTGAPLGLVEFNDVAYWPQIKQVLEWSKDHVTSTLFVCWAVQAALN
   Consensus    (101)   DGLIVTGAPLGLVEFNDVAYWPQIKQVLEWSKDHVTSTLFVCWAVQAALN
                        151                                               200
        metA    (151)   ILYGIPKQTRTEKLSGVYEHHILHPHALLTRGFDDSFLAPHSRYADFPAA
metA11/metA12   (151)   ILYGIPKQTRTEKLSGVYEHHILHPHALLTRGFDDSFLAPHSRYADFPAA
      metA13    (151)   ILYGIPKQTRTEKLSGVYEHHILHPHALLTRGFDDSFLAPHSRYADFPAA
      metA14    (151)   ILYGIPKQTRTEKLSGVYEHHILHPHALLTRGFDDSFLAPHSRYADFPAA
   Consensus    (151)   ILYGIPKQTRTEKLSGVYEHHILHPHALLTRGFDDSFLAPHSRYADFPAA
                        201                                               250
        metA    (201)   LIRDYTDLEILAETEEGDAYLFASKDKRIAFVTGHPEYDAQTLAQEFFRD
metA11/metA12   (201)   LIRDYTDLEILAETEEGDAYLFASKDKRIAFVTGHPEYDAQTLAQEFFRD
      metA13    (201)   LIRDYTDLEILAETEEGDAYLFASKDKRIAFVTGHPEYDAQTLAQEFFRD
      metA14    (201)   LIRDYTDLEILAETEEGDAYLFASKDKRIAFVTGHPEYDAQTLAQEFFRD
   Consensus    (201)   LIRDYTDLEILAETEEGDAYLFASKDKRIAFVTGHPEYDAQTLAQEFFRD
                        251                                               300
        metA    (251)   VEAGLDPDVPYNYFPHNDPQNTPRASWRSHGNLLFTNWLNYYVYQITPYD
metA11/metA12   (251)   VEAGLDPDVPYNYFPHNDPQNTPRASWRSHGNLLFTNWLNYYVYQITPYD
      metA13    (251)   VEAGLDPDVPYNYFPHNDPQNTPRASWRSHGNLLFTNWLNYYVYQITPYD
      metA14    (251)   VEAGLDPDVPYNYFPHNDPQNTPRASWRSHGNLLFTNWLNYYVYQITPYD
   Consensus    (251)   VEAGLDPDVPYNYFPHNDPQNTPRASWRSHGNLLFTNWLNYYVYQITPYD
                        301
        metA    (301)   LRHMNPTLD-
metA11/metA12   (301)   LRHMNPTLD-
      metA13    (301)   LRHMNPTLD-
      metA14    (301)   LRHMNPTLD-
   Consensus    (301)   LRHMNPTLD
```

```
MAKHLFTSESVSEGHPDKIADQISDAVLDAILEQDPKARVACETYVKTGM        49

N                             A
VLVGGEITTSAWVDIEEITRNTVREIGYVHSDMGFDANSCAVLSAIGKQS        99

S          S                    L    Y
PDINQGVDRADPLEQGAGDQGLMFGYATNETDVLMPAPITYAHRLVQRQA       149

C                        D    Y
EVRKNGTLPWLRPDAKSQVTFQYDDGKIVGIDAVVLSTQHSEEIDQKSLQ       199

I      S    A
EAVMEEIIKPILPAEWLTSATKFFINPTGRFVIGGPMGDCGLTGRKIIVD       249

D                      F
TYGGMARHGGGAFSGKDPSKVDRSAAYAARYVAKNIVAA GLADRCEIQVS      299

L
YAIGVAEPTSIMVETFGTEKVPSEQLTLLVREFFDLRPYGLIQMLDLLHP       349

AMLPV
IYKETAAYGHFGREHFPWEKTDKAQLLRDAAGLK       383
```

Fig. 5

US 8,795,990 B2

RECOMBINANT ENZYME WITH ALTERED FEEDBACK SENSITIVITY

SEQUENCE LISTING

This application contains a Sequence Listing which has been submitted via EFS-Web and is hereby incorporated by reference in its entirety. Said ASCII copy, created on Mar. 15, 2010, is named REG06146.txt, and is 196,993 bytes in size.

FIELD OF THE INVENTION

The present invention relates to the use of recombinant homoserine transsuccinylase enzymes with altered feedback sensitivity (MetA*) and eventually, recombinant S-adenosyl methionine synthetase enzymes with reduced activity (MetK*) for the production of methionine, its precursors or derivatives thereof.

PRIOR ART

Sulfur-containing compounds such as cysteine, homocysteine, methionine or S-adenosylmethionine are critical to cellular metabolism and are produced industrially to be used as food or feed additives and pharmaceuticals. In particular methionine, an essential amino acid, which cannot be synthesized by animals, plays an important role in many body functions. Aside from its role in protein biosynthesis, methionine is involved in transmethylation and in the bioavailability of selenium and zinc. Methionine is also directly used as a treatment for disorders like allergy and rheumatic fever. Nevertheless most of the methionine which is produced is added to animal feed.

With the decreased use of animal-derived proteins as a result of BSE and chicken flu, the demand for pure methionine has increased. Chemically D,L-methionine is commonly produced from acrolein, methyl mercaptan and hydrogen cyanide. Nevertheless the racemic mixture does not perform as well as pure L-methionine, as for example in chicken feed additives (Saunderson, C. L., (1985) British Journal of Nutrition 54, 621-633). Pure L-methionine can be produced from racemic methionine e.g. through the acylase treatment of N-acetyl-D,L-methionine which increases production costs dramatically. The increasing demand for pure L-methionine coupled to environmental concerns render microbial production of methionine attractive.

Microorganisms have developed highly complex regulatory mechanisms that fine-tune the biosynthesis of cell components thus permitting maximum growth rates. Consequently only the required amounts of metabolites, such as amino acids, are synthesized and can usually not be detected in the culture supernatant of wild-type strains. Bacteria control amino acid biosynthesis mainly by feedback inhibition of enzymes, and repression or activation of gene transcription. Effectors for these regulatory pathways are in most cases the end products of the relevant pathways. Consequently, strategies for overproducing amino acids in microorganisms require the deregulation of these control mechanisms.

The pathway for L-methionine synthesis is well known in many microorganisms (FIG. 1A/B). Methionine is derived from the amino acid aspartate, but its synthesis requires the convergence of two additional pathways, cysteine biosynthesis and C1 metabolism (N-methyltetrahydrofolate). Aspartate is converted into homoserine by a sequence of three reactions. Homoserine can subsequently enter the threonine/isoleucine or methionine, biosynthetic pathway. In E. coli entry into the methionine pathway requires the acylation of homoserine to succinylhomoserine. This activation step allows subsequent condensation with cysteine, leading to the thioether-containing cystathionine, which is hydrolyzed to give homocysteine. The final methyl transfer leading to methionine is carried out by either a $B_{12}$-dependent or a $B_{12}$-independent methyltransferase.

Methionine biosynthesis in E. coli is regulated by repression and activation of methionine biosynthetic genes via the MetJ and MetR proteins, respectively (reviewed in Neidhardt, F. C. (Ed. in Chief), R. Curtiss III, J. L. Ingraham, E. C. C. Lin, K. B. Low, B. Magasanik, W. S. Reznikoff, M. Riley, M. Schaechter, and H. E. Umbarger (eds). 1996. Escherichia coli and Salmonella: Cellular and Molecular Biology. American Society for Microbiology; Weissbach et al., 1991 Mol. Microbiol., 5, 1593-1597). MetJ uses S-adenosylmethionine as a corepressor, that is made from methionine by the enzyme S-adenosylmethionine synthetase (EC 2.5.1.6) encoded by the essential gene metK. metA encoding homoserine transsuccinylase (EC 2.3.1.46), the first enzyme unique to the synthesis of methionine is another major control point for methionine production. Besides the transcriptional regulation of metA by MetJ and MetR the enzyme is also feedback regulated by the end-products methionine and S-adenosylmethionine (Lee, L.-W. et al. (1966) Multimetabolite control of a biosynthetic pathway by sequential metabolites, JBC 241 (22), 5479-5780). Feedback inhibition by these two products is synergistic meaning that low concentrations of each metabolite alone are only slightly inhibitory, while in combination a strong inhibition is exerted.

Amino acid analogues inhibit bacterial growth through the synthesis of abnormal polypeptides and by interfering with feedback inhibition, which lead to detrimental processes inside the cell. Analogue-resistant mutants have been obtained which show altered and deregulated enzymes leading to excess synthesis of the corresponding metabolites that can outcompete the analogue. Several groups have used the methionine analogues norleucine, ethionine, and α-methylmethionine to generate microbial strains that overproduce methionine. It was shown that α-methylmethionine is a potent inhibitor of the homoserine transsuccinylase enzyme MetA (Rowbury R J, (1968) The inhibitory effect of α-methylmethionine on Escherichia coli, J. gen. Microbiol., 52, 223-230). Feedback resistant mutants in Salmonella typhimurium that mapped to the metA locus were isolated (Lawrence D. A., (1972) Regulation of the methionine feedback-sensitive enzyme in mutants of Salmonella typhimurium; Lawrence, D. A., Smith, D. A., Rowbury, R. J. (1967) Regulation of methionine synthesis in Salmonella typhimurium: Mutants resistant to inhibition by analogues of methionine; Genetics 58, 473-492). Norleucine resistant mutants were shown to map to the metK locus. (Chattopadhyay, M. K., Ghosh, A. K. and Sengupta, S. (1991), Control of methionine biosynthesis in Escherichia coli K12: a closer study with analogue resistant mutants, Journal of General Microbiology, 137, 685-691). The same authors have reported the isolation of feedback resistant metA mutants and norleucine resistant mutants in E. coli, but the actual mutations in metA and metK have not been described.

The critical role of homoserine transsuccinylase for bacterial methionine production by fermentation has been demonstrated (Kumar, D. Garg, S. Bisaria V. S., Sreekrishnan, T. R. and Gomes, J. (2003) Production of methionine by a multi-analogue resistant mutant of Corynebacterium lilium, Process Biochemistry 38, 1165-1171). The patent application JP2000139471 describes a process for the production of L-methionine using mutants in the genes metA and metK. In this case the precise location of the mutations has been determined. The MetA mutant enzymes have partially lost the sensitivity to feed-back inhibition by methionine and S-adenosyl-methionine. Nevertheless their initial activities are decreased down to about 25% when compared to the wildtype enzyme, and at concentrations of 1 mM methionine for some mutants or 1 mM SAM for others another 25-90% of the enzyme activity is lost. The meiK mutants were not characterized enzymatically but used in fermentations to increase the amount of methionine produced.

GENERAL DISCLOSURE OF THE INVENTION

This invention relates to a method for the preparation of methionine, its precursors or products derived thereof in a fermentative process with a microorganism where L-homoserine is converted into O-succinyl-homoserine with a homoserine transsuccinylase, comprising the step of culturing the said microorganism on an appropriate medium and recovering methionine, its precursors or products derived thereof once produced, wherein the homoserine transsuccinylase is a mutated homoserine transsuccinylase with reduced sensitivity for the feedback inhibitors S-adenosylmethionine and methionine.

The invention also relates to the same method with microorganisms where the S-adenosyl-methionine synthetase enzyme activity is reduced.

The present invention also concerns the mutated enzymes, nucleotide sequences coding for the said enzymes with reduced sensitivity or activity and microorganisms comprising the said nucleotide sequences as disclosed above and below.

The recombinant enzymes can be used together and can also be combined with several other changes in the corresponding microorganisms such as overexpression of genes or their deletion. Preferentially the gene encoding aspartokinase/homoserine dehydrogenase (metL or thrA) is over expressed and the gene encoding the methionine repressor metJ is deleted.

In the description of the present invention, genes and proteins are identified using the denominations of the corresponding genes in *E. coli*. However, and unless specified otherwise, use of these denominations has a more general meaning according to the invention and covers all the corresponding genes and proteins in other organisms, more particularly microorganisms.

PFAM (protein families database of alignments and hidden Markov models) represents a large collection of protein sequence alignments. Each PFAM makes it possible to visualize multiple alignments, see protein domains, evaluate distribution among organisms, gain access to other databases, and visualize known protein structures.

COGs (clusters of orthologous groups of proteins) are obtained by comparing protein sequences from 43 fully sequenced genomes representing 30 major phylogenic lines. Each COG is defined from at least three lines, which permits the identification of former conserved domains.

The means of identifying homologous sequences and their percentage homologies are well known to those skilled in the art, and include in particular the BLAST programs, which can be used with the default parameters. The sequences obtained can then be exploited (e.g., aligned) using, for example, the sequence alignment programs with the default parameters.

Using the references given on GenBank for known genes, those skilled in the art are able to determine the equivalent genes in other organisms, bacterial strains, yeasts, fungi, mammals; plants, etc. This routine work is advantageously done using consensus sequences that can be determined by carrying out sequence alignments with genes derived from other microorganisms, and designing degenerate probes to clone the corresponding gene in another organism. These routine methods of molecular biology are well known to those skilled in the art, and are described, for example, in Sambrook et al. (1989 Molecular Cloning: a Laboratory Manual. $2^{nd}$ ed. Cold Spring Harbor Lab., Cold Spring Harbor, N.Y.).

DETAILED DESCRIPTION OF THE INVENTION

The modified homoserine succinyltransferases showing a decreased feed-back sensitivity to methionine and S-adenosylmethionine in comparison to the wild-type enzyme, according to the present invention, comprises at least one amino acid mutation when compared with the wild-type sequence. The mutation is preferentially selected in the conserved regions coding for amino acids 24 to 30 or in the region coding for amino acids 58 to 65 or in the region coding for amino acids 292 to 298 with the first amino acid proline after the formylmethionine counting as number 1.

All references to amino acid positions are made based on the homoserine succinyltransferase encoded by the metA gene of *E. coli* represented in FIG. 2. The relative positions of corresponding conserved regions in other homoserin succinyltransferases from different organisms can be found by a person skilled in the art by simple sequence alignment as represented on FIG. 3 with the enzymes listed below:

gi|20138683|sp|Q97I29|META *Clostridium acetobutylicum* Homoserine O-succinyltransferase gi|12203304|sp|Q9PLV2|META *Campylobacter jejuni* Homoserine O-succinyltransferase gi|12230277|sp|Q9KAK7|META *Bacillus halodurans* Homoserine O-succinyltransferase gi|20138686|sp|Q97PM9|META *Streptococcus pneumoniae* Homoserine O-succinyltransferase gi|20138715|sp|Q9CEC5|META *Lactococcus lactis* Homoserine O-succinyltransferase gi|20138656|sp|Q92L99|META *Sinorhizobium meliloti* Homoserine O-succinyltransferase gi|20138618|sp|Q8YBV5|META *Brucella melitensis* Homoserine O-succinyltransferase gi|20141549|sp|P37413|META *Salmonella typhimurium* Homoserine O-succinyltransferase gi|20138601|sp|Q8X610|META *Escherichia coli* O157: H7 Homoserine O-succinyltransferase gi|12231004|sp|P07623|META *Escherichia coli* Homoserine O-succinyltransferase gi|12230285|sp|Q9KRM5|META *Vibrio cholerae* Homoserine O-succinyltransferase gi|38258142|sp|Q8FWG9|META *Brucella melitensis* biovar suis Homoserine O-succinyltransferase gi|20138631|sp|Q8ZAR4|META *Yersinia pestis* Homoserine O-succinyltransferase gi|12231010|sp|P54167|META *Bacillus subtilis* Homoserine O-succinyltransferase gi|12230320|sp|Q9WZY3|META *Thermotoga maritima* Homoserine O-succinyltransferase gi|20138625|sp|Q8Z1W1|META *Salmonella typhi* Homoserine O-succinyltransferase >gi|31340217|sp|Q8D937|META *Vibrio vulnificus* Homoserine O-succinyltransferase gi|31340213|sp|Q87NW7|META *Vibrio parahaemolyticus* Homoserine O-succinyltransferase The modified homoserine succinyltransferases preferentially exhibit a specific activity which is at least ten times that of the wild-type enzyme in the presence of 10 mM methionine and 1 mM S-adenosylmethionine and at least 80 tunes that of the wild-type enzyme in the presence of 10 mM methionine and 0.1 mM S-adenosylmethionine. Preferred enzymes retain an activity of at least two percent of their initial activity in the presence of 100 mM methionine and 1 mM S-adenosylmethionine.

Preferentially, the protein sequence of the modified homoserine succinyltransferase according to the invention contains the amino acid mutation of at least one of the conserved regions sequences specified below.

Preferentially at least one mutation is present in the conserved region 1 comprising the amino acid sequence defined below, in the N-terminal part of the wild type homoserine transsuccinylases, corresponding to amino acid 24 to 30 in the amino acid sequence of *E. coli* MetA shown in SEQ ID NO 1. This non mutated conserved region I has the following sequence:

X1-X2-X3-A-X4-X5-Q    (SEQ ID NO: 35)

In which
X1 represents E, D, T, S, L, preferentially T
X2 represents D, S, K, Q, E, A, R, preferentially S
X3 represents R, E, D, preferentially R
X4 represents Y, I, F, A, K, S, V, preferentially S
X5 represents H, S, N, G, T, R, preferentially G.

In a preferred embodiment the unmodified homoserine succinyltransferase conserved region 1 has the following amino acid sequence:

T-S-R-A-S-G-Q    (SEQ ID NO: 36).

In another preferred embodiment of the invention, at least one mutation is present in the conserved region 2, also in the N-terminal part of the wild type homoserine transsuccinylase, corresponding to amino acid 58 to 65 in the amino acid sequence of *E. coli* MetA shown in SEQ ID NO 1. The non mutated conserved region 2 has the following formula:

X1-X2-X3-P-L-Q-X4-X5    (SEQ ID NO: 37)

In which
X1 represents G, A, S, preferentially S
X2 represents N, A, preferentially N
X3 represents S, T, preferentially S
X4 represents V, L, I, preferentially V
X5 represents N, E, H, D, preferentially D.

In a preferred embodiment the unmodified homoserine succinyltransferase conserved region 2 has the following amino acid sequence:

S-N-S-P-L-Q-V-D    (SEQ ID NO: 38).

In a third embodiment of the invention the homoserine succinyltransferase comprises at least one mutation in a conserved region in its C-terminal part, corresponding to amino acid 292 to 298 in the amino acid sequence of *E. coli* MetA shown in SEQ ID NO 1. The non mutated conserved region 3 has the following formula:

X1-Y-Q-X2-T-P-X3    (SEQ ID NO: 39)

In which
X1 represents V, I, M, preferentially V
X2 represents E, K, G, I, Q, T, S, preferentially I
X3 represents F, Y, preferentially Y.

In a preferred embodiment, the unmodified homoserine succinyltransferase conserved region 3 has the following amino acid sequence:

V-Y-Q-I-T-P-Y    (SEQ ID NO: 40).

In a preferred embodiment, the conserved alanine in conserved region 1 is replaced with another amino acid, more preferentially with a valine. The modified conserved region has most preferentially the following amino acid sequence:

T-S-R-V-S-G-Q    (SEQ ID NO: 41).

In another preferred embodiment, the conserved amino acids L and/or Q in conserved region 2 are replaced with other amino acids. Preferentially, leucine is replaced by phenylalanine and/or glutamine is replaced with a glutamate or aspartate. Most preferentially, the modified conserved region 2 has the following amino acid sequence:

S-N-S-P-L-E-V-D    (SEQ ID NO: 42).

In a further preferred embodiment, the conserved amino acids L and/or Q in conserved region 3 are replaced with another amino acid.

In a preferred application the metA gene is the homoserine transsuccinylase enzyme of *E. coli* K12 represented by the SEQ ID NO 1 and sequences homologous to that sequence that have homoserine transsuccinylase activity and that share at least 80% homology, preferentially 90% homology with the amino acid sequence of SEQ ID NO 1.

Modified homoserine succinyltransferases, may be obtained, for example, by selecting strains growing in the presence of methionine analogues such as α-methylmethionine, norleucine or ethionine. Preferentially these strains will be selected while growing in the presence of α-methylmethionine.

The present invention furthermore relates to nucleotide sequences, DNA or RNA sequences, which encode a mutated homoserine succinyltransferase according to the invention as defined above. In a preferred embodiment, the DNA sequence is characterized by the fact that it comprises at least one mutation in the coding regions of the conserved regions 1 to 3 of the wild type metA gene, represented in SEQ ID NO 1, the said mutation being not a silent mutation.

These DNA sequences can be prepared, for example, from the strains growing in the presence of methionine analogues. The starting DNA fragment encompassing the modified metA gene, is cloned in a vector using standard known techniques for preparing recombinant DNA.

These DNA sequences can also be prepared, for example, by non-specific or by targeted mutagenesis methods from strains harboring the DNA sequence encoding wild-type homoserine succinyltransferase.

Non-specific mutations within the said DNA region may be produced, for example, by chemical agents (e.g. nitrosoguanidine, ethylmethanesulfonic acid and the like) and/or by physical methods and/or by PCR reactions, which are carried out under particular conditions.

Methods for introducing mutations at specific positions within a DNA fragment are known and are described in Molecular Cloning: a Laboratory Manual, 1989, $2^{nd}$ ed. Cold Spring Harbor Lab., Cold Spring Harbor, N.Y.

Using the aforementioned methods, one or more mutations which cause the modified homoserine succinyltransferase to possess an amino acid sequence which leads to methionine and S-adenosylmethionine insensitivity can be introduced in the said DNA region of any metA gene. Preferentially, one or more nucleotides in the DNA sequence encoding homoserine succinyltransferase are changed such that the amino acid sequence that is encoded by the gene exhibits at least one mutation.

Another method of producing feedback-resistant metA alleles consists in combining different point mutations which lead to feedback resistance, thereby giving rise to multiple mutants possessing new properties.

The modified S-adenosylmethionine synthetase according to the invention has decreased activity in comparison to the wild-type enzyme, and has at least one mutation in its protein sequence when compared to the wild-type sequence.

The mutation is preferentially in one of the conserved regions defined below.

All references to amino acid positions are made based on the S-adenosylmethionine synthetase encoded by the metK gene of *E. coli*. The relative positions of corresponding conserved regions in other S-adenosylmethionine synthetases from different organisms can be found by a person skilled in the art by simple sequence alignment as represented in FIG. 4 with enzymes listed below:

>gi|39574954|emb|CAE78795.1| methionine adenosyltransferase *Bdellovibrio bacteriovorus* HD100]
>gi|45657232|ref|YP_001318.1| s-adenosylmethionine synthetase protein *Leptospira interrogans* serovar Copenhageni str. Fiocruz L1-130
>gi|28378057|ref|NP_784949.1| methionine adenosyltransferase *Lactobacillus plantarum* WCFS1
>gi|26453553|dbj|BAC43885.1| S-adenosylmethionine synthetase *Mycoplasma penetrans*
>gi|24212014|sp|Q9K5E4| S-adenosylmethionine synthetase. *Corynebacterium glutamicum*
>gi|18145842|dbj|BAB81883.1| S-adenosylmethionine synthetase *Clostridium perfringens* str. 13
>gi|13363290|dbj|BAB37241.1| methionine adenosyltransferase 1 *Escherichia coli* O157:H7
>gi|45443250|ref|NP_994789.1| S-adenosylmethionine synthetase *Yersinia pestis* biovar Mediacvails. str. 91001
>gi|44888151|sp|Q7WQX8|METK S-adenosylmethionine synthetase *Borrelia burgdorferi*
>gi|44888141|sp|Q7U4S6| S-adenosylmethionine synthetase *Synechococcus* sp. WH8102
>gi|44888135|sp|Q7 MHK6| S-adenosylmethionine synthetase *Vibrio vulnificus* YJ016
>gi|23466330|ref|NP_696933.1| S-adenosylmethionine synthetase *Bifidobacterium longum* NCC2705]
>gi|21219978|ref|NP_625757.1| S-adenosylmethionine synthetase *Streptomyces coelicolor* A3(2)]
>gi|39937076|ref|NP_949352.1| methionine S-adenosyltransferase *Rhodopseudomonas palustris* CGA009
>gi|16766391|ref|NP_462006.1| methionine adenosyltransferase 1 *Salmonella typhimurium* LT2
>gi|33594910|ref|NP_882553.1| S-adenosylmethionine synthetase *Bordetella parapertussis* 12822
>gi|44888148|sp|Q7VRG5| S-adenosylmethionine synthetase *Candidatus Blochmannia floridanus*
>gi|44888147|sp|Q7VNG71METK_HAEDU S-adenosylmethionine synthetase *Haemophilus ducreyi*
>gi|4488811146|sp|Q7VFY5| S-adenosylmethionine synthetase *Helicobacter hepaticus*
>gi|44888145|sp|Q7VDM7| S-adenosylmethionine synthetase *Prochlorococcus marinus*
>gi|44888142|sp|Q7URU7| S-adenosylmethionine synthetase *Pirellula* spec.
>gi|44888138|sp|Q7NHG0| S-adenosylmethionine synthetase *Gloeobacter violaceus*
>gi|44888137|sp|Q7N119| S-adenosylmethionine synthetase *Photorhabdus luminescens* subsp. *laumondii*
>gi|44888136|sp|Q7MTQ0| S-adenosylmethionine synthetase *Porphyromonas gingivalis*
>gi|39650934|emb|CAE29457.1| methionine S-adenosyltransferase *Rhodopseudomonas palustris* CGA009
>gi|15792421|ref|NP_282244.1| S-adenosylmethionine synthetase *Campylobacter jejuni* subsp. *jejuni* NCTC 11168
>gi|39574954|cmb|CAE78795.1| methionine adenosyltransferase *Bdellovibrio bacteriovorus* HD100
>gi|45657232|ref|YP_001318.1| s-adenosylmethionine synthetase protein *Leptospira interrogans* serovar Copenhageni str. Fiocruz L1-130
>gi|28378057|ref|NP_784949.1| methionine adenosyltransferase *Lactobacillus plantarum* WCFS1
>gi|45600470|gb|AAS69955.1| s-adenosylmethionine synthetase protein *Leptospira interrogans* serovar Copenhageni sr. Fiocruz L1-130
>gi|264535531 dbj|BAC43885.1| S-adenosylmethionine synthetase *Mycoplasma penetrans*
>gi|18145842|dbj|BAB81883.1| S-adenosylmethionine synthetase *Clostridium perfringens* str. 13
>gi|13363290|dbj|BAB37241.1| methionine adenosyltransferase I *Escherichia coli* O157:H7
>gi|45443250|ref|NP_994789.1| S-adenosylmethionine synthetase *Yersinia pestis* biovar. Mediaevails str. 91001
>gi|44888153|sp|Q8CXS7| S-adenosylmethionine synthetase *Leptospira interrogans*
>gi|44888151|sp|Q7WQX8| S-adenosylmethionine synthetase *Bordetella bronchiseptica*
>gi|44888150|sp|Q7W200| S-adenosylmethionine synthetase *Bordetella parapertussis*
>gi|44888149|sp|Q7VUL5| S-adenosylmethionine synthetase *Bordetella pertussis*

The modified S-adenosylmethionine synthetase preferentially exhibits a specific activity which is at least five times less than that of the wild-type enzyme.

Preferentially, the protein sequence of a modified S-adenosylmethionine synthetase contains the amino acid mutation of at least one of the sequences specified below.

In one embodiment of the invention the amino acid changes concern the cystein at position 89 or the cystein at position 239 that both reduce the activity of MetK (Reczkowski and Markham, 1995, JBC 270, 31, 18484-18490).

In a preferred embodiment at least one mutation is present in the conserved region 1, corresponding to amino acid 54 to 59 in the amino acid sequence of *E. coli* MetK shown in SEQ ID NO 2, the non mutated conserved region I comprising the amino acid sequence defined below:

G-E-X1-X2-X3-X4    (SEQ ID NO: 43)

wherein
X1 represents I, V, L, T preferentially I
X2 represents T, K, S, R, preferentially T
X3 represents T, S, G, preferentially T
X4 represents S, N, T, K, E, R, P, N, A preferentially S.

Preferentially the unmodified S-adenosylmethionine synthetase conserved region I has the following amino acid sequence:

G-E-I-T-T-S    (SEQ ID NO: 44).

In another preferred embodiment at least one mutation is present in the conserved region 2, corresponding to amino acid 98 to 107 in the amino acid sequence of *E. coli* MetK shown in SEQ ID NO 2, the non mutated conserved region 2 comprising the amino acid sequence defined below:

Q-S-X1-D-I-X2-X3-G-V-X4    (SEQ ID NO: 45)

wherein
X1 represents P, Q, A, S, preferentially P
X2 represents A, N, Q, S, F, preferentially N
X3 represents V, Q, Y, R, M, N preferentially Q
X4 represents K, D, N, T, S, A, E preferentially D.

Preferentially the unmodified S-adenosylmethionine synthetase conserved region 2 has the following amino acid sequence:

Q-S-P-D-I-N-Q-G-V-D (SEQ ID NO: 46).

Preferentially the unmodified S-adenosylmethionine synthetase conserved region 2 has the following amino acid sequence: Q-S-P-D-I-N-Q-G-V-D.

In another preferred embodiment at least one mutation is present in the conserved region 3, corresponding to amino acid 114 to 121 in the amino acid sequence of *E. coli* MetK shown in SEQ ID NO 2, the non mutated conserved region 3 comprising the amino acid sequence defined below:

X1-G-A-G-D-Q-G-X2 (SEQ ID NO: 47)

wherein
X1 represents Q, A, I, V, E, T, preferentially Q
X2 represents L, I, S, V, M, preferentially L.

Preferentially the unmodified S-adenosylmethionine synthetase conserved region 3 has the following amino acid sequence:

Q-G-A-G-D-Q-G-L (SEQ ID NO: 48).

In another preferred embodiment at least one mutation is present in the conserved region 4, corresponding to amino acid 137 to 144 in the amino acid sequence of *E. coli* MetK shown in SEQ ID NO 2, the non mutated conserved region 4 comprising the amino acid sequence defined below:

X1-I-X2-X3-X4-H-X5-X6 (SEQ ID NO: 49)

wherein
X1 represents S, P, T, A, preferentially P
X2 represents A, T, W, Y, F, S, N preferentially T
X3 represents M, Y, L, V preferentially Y
X4 represents S, A, preferentially A
X5 represents K, R, E, D, preferentially R
X6 represents L, I, preferentially L.

Preferentially the unmodified S-adenosylmethionine synthetase conserved region 4 has the following amino acid sequence:

P-I-T-Y-A-H-R-L (SEQ ID NO: 50).

In another preferred embodiment at least one mutation is present in the conserved region 5, corresponding to amino acid 159 to 163 in the amino acid sequence of *E. coli* MetK shown in SEQ ID NO 2, the non mutated conserved region 5 comprising the amino acid sequence defined below:

X1-L-X2-X3-D (SEQ ID NO: 51)

wherein
X1 represents W, F, Y, V, E preferentially W
X2 represents R, G, L, K, preferentially R
X3 represents P, L, H, V, preferentially P.

Preferentially the unmodified S-adenosylmethionine synthetase conserved region 5 has the following amino acid sequence:

W-L-R-P-D (SEQ ID NO: 52).

Preferentially at least one mutation is present in the conserved region 6, corresponding to amino acid 183 to 189 in the amino acid sequence of *E. coli* MetK shown in SEQ ID NO 2, the non mutated conserved region 6 comprising the amino acid sequence defined below.

X1-X2-X3-S-X4-Q-H (SEQ ID NO: 53)

In which
X1 represents V, I, preferentially V
X2 represents V, L, I, preferentially V
X3 represents V, L, I, M, preferentially L
X4 represents T, V, A, S, H, preferentially T.

In a preferred embodiment the unmodified S-adenosylmethionine synthetase conserved region 6 has the following amino acid sequence:

V-V-L-S-T-Q-H (SEQ ID NO: 54).

Preferentially the mutations are introduced in the conserved region 7, corresponding to amino acid 224 to 230 in the amino acid sequence of *E. coli* MetK shown in SEQ ID NO 2, the non mutated conserved region 7 comprising the amino acid sequence defined below:

X1-N-P-X2-G-X3-F (SEQ ID NO: 55)

In which
X1 represents I, V preferentially I
X2 represents T, G, S, preferentially T
X3 represents R, T, Q, K, S, preferentially R.

In a preferred embodiment the unmodified S-adenosylmethionine synthetase conserved region 7 has the following amino acid sequence:

I-N-P-T-G-R-F (SEQ ID NO: 56).

Preferentially the mutations are introduced into the conserved region 8, corresponding to amino acid 231 to 237 in the amino acid sequence of *E. coli* MetK shown in SEQ ID NO 2, the non mutated conserved region 8 comprising the amino acid sequence defined below:

X1-X2-G-X3-P-X4-X5 (SEQ ID NO: 57)

In which
X1 represents T, V, I, Y, E, preferentially V
X2 represents V, I, L, N, preferentially I
X3 represents G, S, preferentially G
X4 represents M, I, Q, A, H, D preferentially M
X5 represents G, S, A, H preferentially G.

In a preferred embodiment the unmodified S-adenosylmethionine synthetase conserved region 8 has the following amino acid sequence: V-I-G-G-P-M-G (SEQ ID NO: 58).

Preferentially the mutations are introduced in the conserved region 9, corresponding to amino acid 246 to 253 in the amino acid sequence of *E. coli* MetK shown in SEQ ID NO 2, the non mutated conserved region 9 comprising the amino acid sequence defined below:

X1-X2-D-T-Y-G-G (SEQ ID NO: 59)

In which
X1 represents M, I, preferentially I
X2 represents V, I preferentially I.

In a preferred embodiment the unmodified S-adenosylmethionine synthetase conserved region 9 has the following amino acid sequence:

I-V-D-T-Y-G-G (SEQ ID NO: 60).

Preferentially the mutations are introduced into the conserved region 10, corresponding to amino acid 269 to 275 in the amino acid sequence of *E. coli* MetK shown in SEQ ID NO 2, the non mutated conserved region 10 comprising the amino acid sequence defined below:

K-V-D-R-S-X1-X2 (SEQ ID NO: 61)

In which
X1 represents A, G, preferentially A
X2 represents A, S, L, preferentially A.

In a preferred embodiment the unmodified S-adenosylmethionine synthetase conserved region 10 has the following amino acid sequence:

K-V-D-R-S-A-A (SEQ ID NO: 62).

In another preferred application of the invention at least one mutation is present in the conserved region 11. The unmodified S-adenosylmethionine synthetase harbors the conserved region in its C-terminal part with the following amino acid sequence:

X1-X2-Q-X3-X4-Y-A-I-G-X5-X6  (SEQ ID NO: 63)

In which
X1 represents L, E, I, Q, T preferentially E
X2 represents V, I, L preferentially I
X3 represents V, L, I preferentially V
X4 represents A, S preferentially S
X5 represents V, I, R, K, A preferentially V
X6 represents A, V, T, S, preferentially A.

This region corresponds to amino acid 295 to 305 in the amino acid sequence of E. coli MetK shown in SEQ ID NO 2.

In a preferred embodiment the unmodified S-adenosylmethionine synthetase conserved region 11 has the following amino acid sequence:

E-I-Q-V-S-Y-A-I-G-V-A  (SEQ ID NO: 64).

In another preferred application of the invention the mutations are introduced into the N-terminus of the protein leading to a frameshift and changes in the last 6 amino acids.

In the S-adenosylmethionine synthetase with decreased activity preferentially the serine in conserved region 1 is replaced with another amino acid. In a preferred application of the invention the serine is replaced with a asparagine.

In a preferred embodiment the modified S-adenosylmethionine synthetase has the following amino acid sequence in conserved region 1:

G-E-I-T-T-N  (SEQ ID NO: 65).

In the S-adenosylmethionine synthetase with decreased activity preferentially the conserved glycine in conserved region 2 is replaced with another amino acid. In a preferred application of the invention the conserved glycine is replaced with a serine.

In a preferred embodiment the modified S-adenosylmethionine synthetase has the following amino acid sequence in conserved region 2:

Q-S-P-D-I-N-Q-S-V-D  (SEQ ID NO: 66).

In the S-adenosylmethionine synthetase with decreased activity preferentially the conserved glycine in conserved region 3 is replaced with another amino acid. In a preferred application of the invention the conserved glycine is replaced with a serine.

In a preferred embodiment the modified S-adenosylmethionine synthetase has the following amino acid sequence in conserved region 3:

Q-S-A-G-D-Q-G-L  (SEQ ID NO: 67).

In the S-adenosylmethionine synthetase with decreased activity preferentially the conserved histidine and/or the semi-conserved proline in conserved region 4 is/are replaced with other amino acids. In a preferred application of the invention the conserved histidine is replaced with a tyrosine and/or the semi-conserved proline is replaced with a leucine.

In a preferred embodiment the modified S-adenosylmethionine synthetase has one of the following amino acid sequences in conserved region 4:

P-I-T-Y-A-Y-R-L  (SEQ ID NO: 68),

L-I-T-Y-A-H-R-L  (SEQ ID NO: 69),

L-I-T-Y-A-Y-R-L  (SEQ ID NO: 70).

In the S-adenosylmethionine synthetase with decreased activity preferentially the semi-conserved arginine in conserved region 5 is replaced with another amino acid. In a preferred application of the invention the arginine is replaced with a cysteine.

In a preferred embodiment the modified S-adenosylmethionine synthetase has the following amino acid sequence in conserved region 5:

W-L-C-P-D  (SEQ ID NO: 71).

In the S-adenosylmethionine synthetase with decreased activity preferentially the conserved histidine or semi-conserved valine in conserved region 6 is replaced with another amino acid. In a preferred application of the invention the conserved histidine is replaced with a tyrosine and/or the valine with aspartate.

In a preferred embodiment the modified S-adenosylmethionine synthetase has one of the three following amino acid sequences in conserved region 6:

V-V-L-S-T-Q-Y  (SEQ ID NO: 72)

V-D-L-S-T-Q-H  (SEQ ID NO: 73)

V-D-L-S-T-Q-Y  (SEQ ID NO: 74).

In the S-adenosylmethionine synthetase with decreased activity preferentially the semi-conserved threonine in conserved region 7 is replaced with another amino acid. In a preferred application of the invention the threonine is replaced with an isoleucine.

In a preferred embodiment the modified S-adenosylmethionine synthetase has the following amino acid sequence in conserved region 7:

I-N-P-I-G-R-F  (SEQ ID NO: 75).

In the S-adenosylmethionine synthetase with decreased activity preferentially the conserved proline in conserved region 8 is replaced with another amino acid. In a preferred application of the invention the proline is replaced with a serine.

In a preferred embodiment the modified S-adenosylmethionine synthetase has the following amino acid sequence in conserved region 8:

V-I-G-G-S-M-G  (SEQ ID NO: 76).

In the S-adenosylmethionine synthetase with decreased activity preferentially the second conserved glycine in conserved region 9 is replaced with another amino acid. In a preferred application of the invention the glycine is replaced with an aspartate.

In a preferred embodiment the modified S-adenosylmethionine synthetase has the following amino acid sequence in conserved region 9:

I-V-D-T-Y-G-D  (SEQ ID NO: 77).

In the S-adenosylmethionine synthetase with decreased activity preferentially the conserved serine in conserved region 10 is replaced with another amino acid. In a preferred application of the invention the serine is replaced with a phenylalanine.

In a preferred embodiment the modified S-adenosylmethionine synthetase has the following amino acid sequence in conserved region 10:

K-V-D-R-F-A-A  (SEQ ID NO: 78).

In the S-adenosylmethionine synthetase with decreased activity preferentially the conserved isoleucine in conserved region 11 is replaced with other amino acids. In a preferred application of the invention isoleucine is replaced by leucine.

In a preferred embodiment the modified S-adenosylmethionine synthetase has the following amino acid sequence in conserved region 11:

E-I-Q-V-S-Y-A-L-G-V-A        (SEQ ID NO: 79).

The present invention furthermore relates to nucleotide sequences, DNA or RNA sequences, which encode a mutated S-adenosylmethionine synthetase according to the invention as defined above. In a preferred embodiment, these DNA sequences are characterized by the fact that they comprise at least one mutation in the coding DNA sequence regions for the conserved regions 1 to 11 of the wild type metK gene, represented as wild type in SEQ ID NO. 2, the said mutation being not a silent mutation.

In a preferred application the metK gene is the S-adenosylmethionine synthetase of *E. coli* K12 represented by the SEQ ID NO 2 and sequences homologous to that sequence that have S-adenosylmethionine synthetase activity and that share at least 80% homology, preferentially 90% homology with the amino acid sequence of SEQ ID NO 2.

The mutated S-adenosylmethionine synthetase genes described above may be obtained by conventional techniques known to the person skilled in the art disclosed above and below, including random or targeted mutagenesis or synthetic DNA construction.

The metA gene encoding modified homoserine succinyltransferase and/or the metK gene encoding modified S-adenosylmethionine synthetase may be encoded chromosomally or extrachromosomally. Chromosomally there may be one or several copies on the genome that can be introduced by methods of recombination known to the expert in the field. Extrachromosomally both genes may be carried by different types of plasmids that differ with respect to their origin of replication and thus their copy number in the cell. They may be present as 1-5 copies, ca 20 or up to 500 copies corresponding to low copy number plasmids with tight replication (pSC101, RK2), low copy number plasmids (pACYC, pRSF1010) or high copy number plasmids (pSK bluescript II).

The metA and/or metK gene may be expressed using promoters with different strength that need or need not to be induced by inducer molecules. Examples are the promoter Ptrc, Ptac, Plac, the lambda promoter cl or other promoters known to the expert in the field.

MetA and/or MetK expression may be boosted or reduced by elements stabilizing or destabilizing the corresponding messenger RNA (Carrier and Keasling (1998) Biotechnol. Prog. 15, 58-64) or the protein (e.g. GST tags; Amersham Biosciences).

The present invention also relates to microorganisms which contain a feedback-resistant metA allele according to the invention and eventually a metK allele with reduced activity according to the invention.

Such strains are characterized by the fact that they possess a methionine metabolism which is deregulated by at least one feedback-resistant metA allele and/or by a reduced production of SAM caused by a MetK enzyme with reduced activity.

Novel strains may be prepared from any microorganism in which methionine metabolism proceeds by the same metabolic pathway.

Gram-negative bacteria, in particular *E. coli*, are especially suitable.

For the purpose of expressing the modified homoserine succinyltransferase enzyme and S-adenosylmethionine synthetase, the feedback-resistant metA alleles and metK alleles with reduced activity are transformed in a host strain using customary methods. The screening for strains possessing modified homoserine succinyltransferase and S-adenosylmethionine synthetase properties is, for example, realized using enzymatic tests.

For example, the homoserine succinyltransferase activity can be determined in an enzymatic test with homoserine and succinyl-CoA as substrates. The reaction is started by adding the protein extract containing the homoserine succinyltransferase enzyme, and the formation of O-succinylhomoserine is monitored by GC-MS after protein precipitation and derivatization with a silylating reagent. Feedback inhibition is tested in the presence of methionine and S-adenosylmethionine in the reaction mixture.

S-adenosylmethionine synthetase activity can be determined in an enzymatic test with methionine and ATP as substrates. The reaction is started by adding the protein extract containing the S-adenosylmethionine synthetase enzyme, and the formation of S-adenosylmethionine is monitored by FIA-MS/MS.

Preferentially, use is made of *E. coli* strains in which the endogenous metA and metK genes are inactivated and complemented by novel recombinant genes.

The feedback-resistant metA alleles and the metK alleles with reduced activity render it possible to abolish the control at important biosynthetic control points, thereby amplifying the production of a large number of compounds which are situated downstream of aspartate. These include, in particular, homoserine, O-succinylhomoserine, cystathionine, homocysteine, methionine and S-adenosylmethionine.

In particular the invention relates to the preparation of L-methionine, its precursors or compounds derived thereof, by means of cultivating novel microorganisms. The above-described products are classified below as compound (I).

An increase in the production of compound (I) can be achieved by changing the expression levels or deleting the following genes implicated in the production of aspartate, a precursor of compound (I).

| Gene | genbank entry | name |
| --- | --- | --- |
| ackA | g1788633 | acetate kinase |
| pta | g1788635 | phosphotransacetylase |
| acs | g1790505 | acetate synthase |
| aceA | g1790445 | isocitrate lyase |
| aceB | g1790444 | malate synthase |
| aceE | g1786304 | pyruvate deydrogenase E1 |
| aceF | g1786305 | pyruvate deydrogenase E2 |
| lpd | g1786307 | pyruvate deydrogenase E3 |
| aceK | g1790446 | isocitrate dehydrogenase kinase/phosphatase |
| sucC | g1786948 | succinyl-CoA synthetase, beta subunit |
| sucD | g1786949 | succinyl-CoA synthetase, alpha subunit |
| ppc | g1790393 | phosphoenolpyruvate carboxylase |
| pck | g1789807 | phosphoenolpyruvate carboxykinase |
| pykA | g1788160 | pyruvate kinase II |
| pykF | g1787965 | pyruvate kinase I |
| poxB | g1787096 | pyruvate oxidase |
| pps | g1787994 | phosphoenolpyruvate synthase |
| ilvB | g1790104 | acetohydroxy acid synthase I, large subunit |
| ilvN | g1790103 | acetohydroxy acid synthase I, small subunit |
| ilvG | g1790202 g1790203 | acetohydroxy acid synthase II, large subunit |
| ilvM | g1790204 | acetohydroxy acid synthase II, small subunit |
| ilvI | g1786265 | acetohydroxy acid synthase III, large subunit |
| ilvH | g1786266 | acetohydroxy acid synthase III, small subunit |
| aroF | g1788953 | DAHP synthetase |
| aroG | g1786969 | DAHP synthetase |
| aroH | g1787996 | DAHP synthetase |
| aspC | g1787159 | aspartate aminotransferase |

In addition pyruvate carboxylase, from *Rhizobium etli*, (accession number U51439) may be introduced by genetic engineering into *E. coli* and overexpressed.

An additional increase in the production of compound (I) can be achieved by overexpressing genes of the lysine/methionine/pathway, such as the homoserine synthesizing enzymes encoded by the genes thrA (homoserine dehydrogenase/aspartokinase, gI786183) or metL (homoserine dehydrogenase/aspartokinase, gI790376) or lysC (apartokinase, gI790455) or asd (aspartate semialdehyde dehydrogenase, gI789841) or a combination thereof.

A further increase in the production of (I) is possible by overexpressing genes involved in sulfate assimilation and production of cysteine. This can be achieved by overexpressing the following genes (see below) or by deregulating the pathway through the introduction of a constitutive cysB allele as described by Colyer and Kredich (1994 Mol Microbiol 13 797-805) and by introducing a cysE allele encoding a serine acetyl transferase with decreased sensitivity for its inhibitor L-cysteine (U.S. Pat. No. 6,218,168, Denk & Bock 1987 J Gen Microbiol 133 515-25). The following genes need to be overexpressed.

| CysA | gI788761 | sulfate permease |
| --- | --- | --- |
| CysU | gI788764 | cysteine transport system |
| CysW | gI788762 | membrans bound sulphate transport system |
| CysZ | gI788753 | ORF upstream of cysK |
| cysN | gI789108 | ATP sulfurylase |
| cysD | gI789109 | sulfate adenylyltransferase |
| cysC | gI789107 | adenylylsulfate kinase |
| cysH | gI789121 | adenylylsulfate reductase |
| cysI | gI789122 | sulfite reductase, alpha subunit |
| cysJ | gI789123 | sulfite reductase, beta subunit |
| cysE | gI790035 | serine acetyltransferase |
| cysK | gI788754 | cysteine synthase |
| cysM | g2367138 | O-acetyl-sulfhydrolase |

In addition genes involved in the production of C1 (methyl) groups may be enhanced by overexpressing the following genes:

| serA | gI789279 | phosphoglycerate dehydrogenase |
| --- | --- | --- |
| serB | gI790849 | phosphoserine phosphatase |
| serC | gI787136 | phosphoserine aminotransferase |
| glyA | gI788902 | serine hydroxymethyltransferase |
| metF | gI790377 | 5,10-Methylenetetrahydrofolate reductase |

In addition genes directly involved in the production of methionine may be overexpressed:

| metB | gI790375 | Cystathionine gamma-synthase |
| --- | --- | --- |
| metC | gI789383 | Cystathionine beta-lyase |
| metH | gI790450 | B12-dependent homocysteine-N5-methyltetrahydrofolate transmethylase |
| metE | g2367304 | Tetrahydropteroyltriglutamate methyltransferase |
| metF | gI790377 | 5,10-Methylenetetrahydrofolate reductase |
| metR | gI790262 | Positive regulatory gene for metE and metH and autogenous regulation. |

Furthermore expression of genes in pathways degrading methionine or deviating from the methionine production pathway may be reduced or the genes may be deleted.

| speD | gI786311 | S-Adenosylmethionine decarboxylase |
| --- | --- | --- |
| speC | gI789337 | Ornithine decarboxylase |
| thrB | gI786184 | Homoserine kinase |
| astA | gI788043 | Arginine succinyltransferase |
| dapA | gI788823 | Dihydrodipicolinate synthase. |

A further increase in the production of (1) is possible by means of deleting the gene for the repressor protein MetJ, responsible for the down-regulation of the methionine regulon as was suggested in JP 2000157267-A/3 (see also GenBank gI790373).

Production of (I) may be further increased by using an altered metB allele that uses preferentially or exclusively $H_2S$ and thus produces homocysteine from O succinylhomoserine as has been described in the patent application PCT No PCT/FR04/00354, which content is incorporated herein by reference.

In another preferred embodiment, the gene encoding aspartokinase/homoserine dehydrogenase is over expressed and/or the gene encoding methionine repressor metJ is deleted in the microorganism of the present invention and in the microorganism used in the method according to the invention.

Preferably, the aspartokinase/homoserine dehydrogenase is encoded by a feed-back deregulated ThrA allele. Such feed-back deregulation may be obtained by introducing the mutation Phe318Ser in the ThrA enzyme. Enzyme position is given here by reference to the ThrA sequence disclosed in genebank accession number V00361.1 (gI786183).

The metA and metK alleles described above may be used in eukaryotes or prokaryotes. Preferentially the organism used is a prokaryote. In a preferred application the organism is either *E. coli* or *C. glutamicum*.

The invention also concerns the process for the production of compound (I). Compound (I) is usually prepared by fermentation of the designed bacterial strain.

According to the invention, the terms 'culture' and 'fermentation' are used indifferently to denote the growth of a microorganism on an appropriate culture medium containing a simple carbon source.

According to the invention a simple carbon source is a source of carbon that can be used by those skilled in the art to obtain normal growth of a microorganism, in particular of a bacterium. In particular it can be an assimilable sugar such as glucose, galactose, sucrose, lactose or molasses, or by-products of these sugars. An especially preferred simple carbon source is glucose. Another preferred simple carbon source is sucrose.

Those skilled in the art are able to define the culture conditions for the microorganisms according to the invention. In particular the bacteria are fermented at a temperature between 20° C. and 55° C., preferentially between 25° C. and 40° C., and more specifically about 30° C. for *C. glutamicum and* about 37° C. for *E. coli*.

The fermentation is generally conducted in fermenters with an inorganic culture medium of known defined composition adapted to the bacteria used, containing at least one simple carbon source, and if necessary a co-substrate necessary for the production of the metabolite.

In particular, the inorganic culture medium for *E. coli* can be of identical, or similar composition to an M9 medium (Anderson, 1946, *Proc. Natl. Acad. Sci. USA* 32:120-128), an M63 medium (Miller, 1992; A Short Course in Bacterial Genetics: A Laboratory Manual and Handbook for *Escherichia coli* and Related Bacteria, Cold Spring Harbor Laboratory Press, Cold Spring Harbor, N.Y.) or a medium such as defined by Schaefer et al. (1999, *Anal. Biochem.* 270: 88-96).

Analogously, the inorganic culture medium for *C. glutamicum* can be of identical or similar composition to BMCG medium (Liebl et al., 1989, *Appl. Microbiol. Biotechnol.* 32: 205-210) or to a medium such as that described by Riedel et al. (2001, *J. Mol. Microbiol. Biotechnol.* 3: 573-583). The media can be supplemented to compensate for auxotrophies introduced by mutations.

After fermentation compound (I) is recovered and purified if necessary. The methods for the recovery and purification of compound (I) such as methionine in the culture media are well known to those skilled in the art.

FIG. 1A/B: Methionine metabolism in *Escherichia coli*.

FIG. 2: Alignment of wildtype and recombinant metA genes obtained upon selection on α-methyl-methionine. Conserved residues are represented by light grey boxes and mutated residues are indicated by white boxes. The figure discloses SEQ ID NO:s 84-88, respectively, in order of appearance.

FIG. 3A: Alignment of MetA sequences from different microorganisms. The figure discloses SEQ ID NO:s 89-106, respectively, in order of appearance.

Figure 3B:
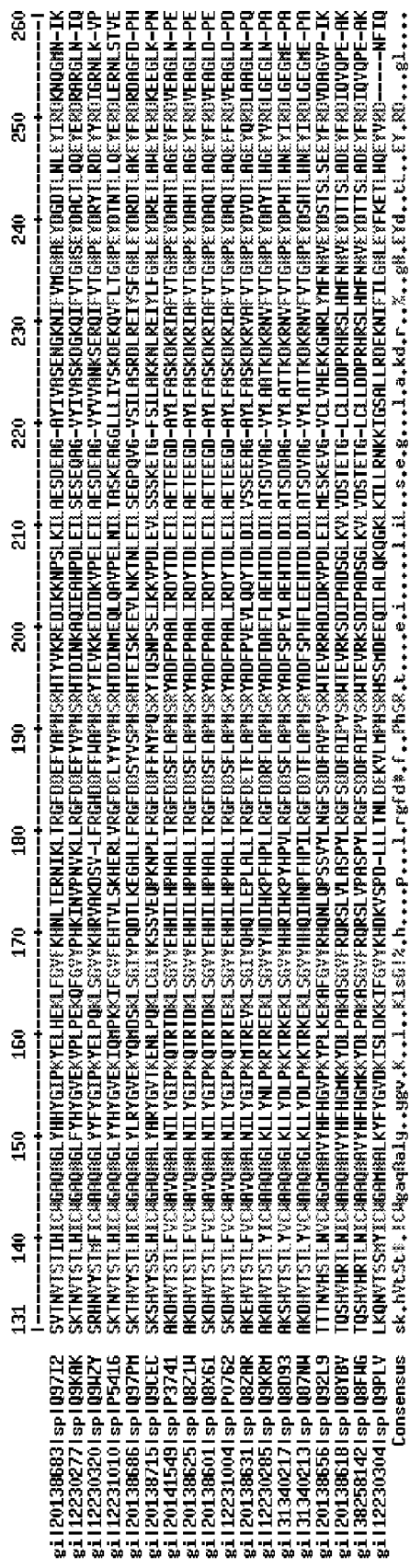

FIG. 3B: Continuation of the alignment of MetA sequences from different microorganisms depicted in FIG. 3A.

Figure 3C:
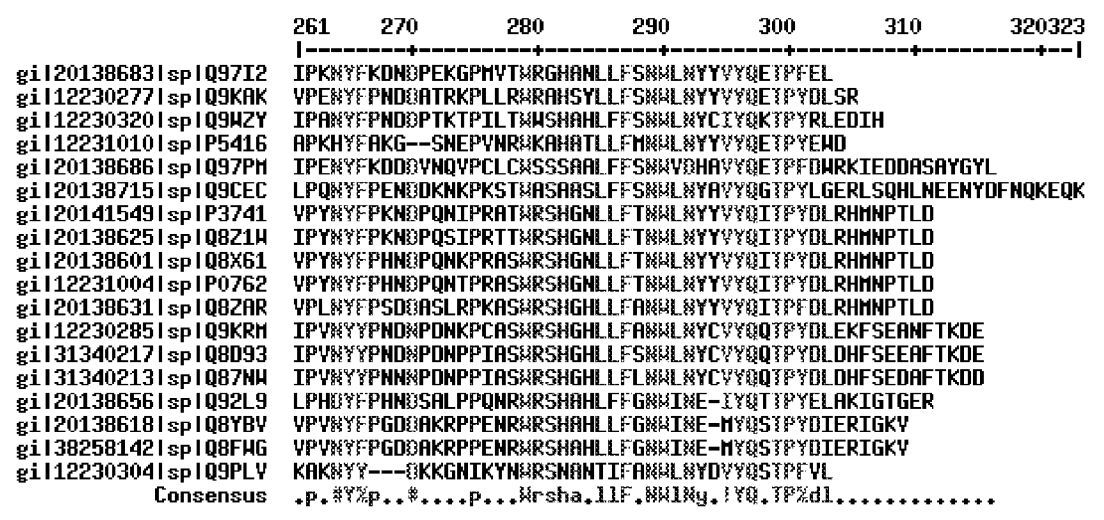

FIG. 3C: Continuation of the alignment of MetA sequences from different mircoorganisms depicted in FIG. 3B.

Figure 4A:
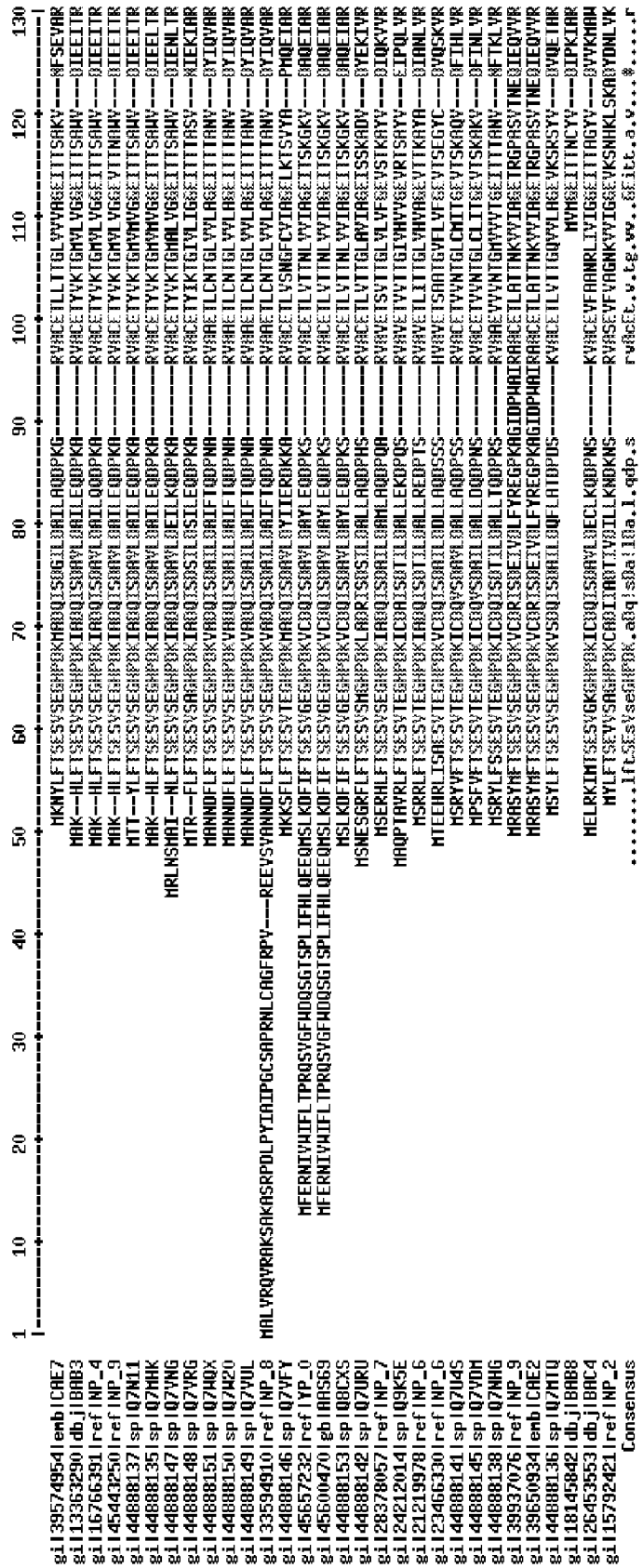

FIG. 4A: Alignment of MetK sequences from different microorganisms. The figure discloses SEQ ID NO:s 107-136, respectively, in order of appearance.

Figure 4B:
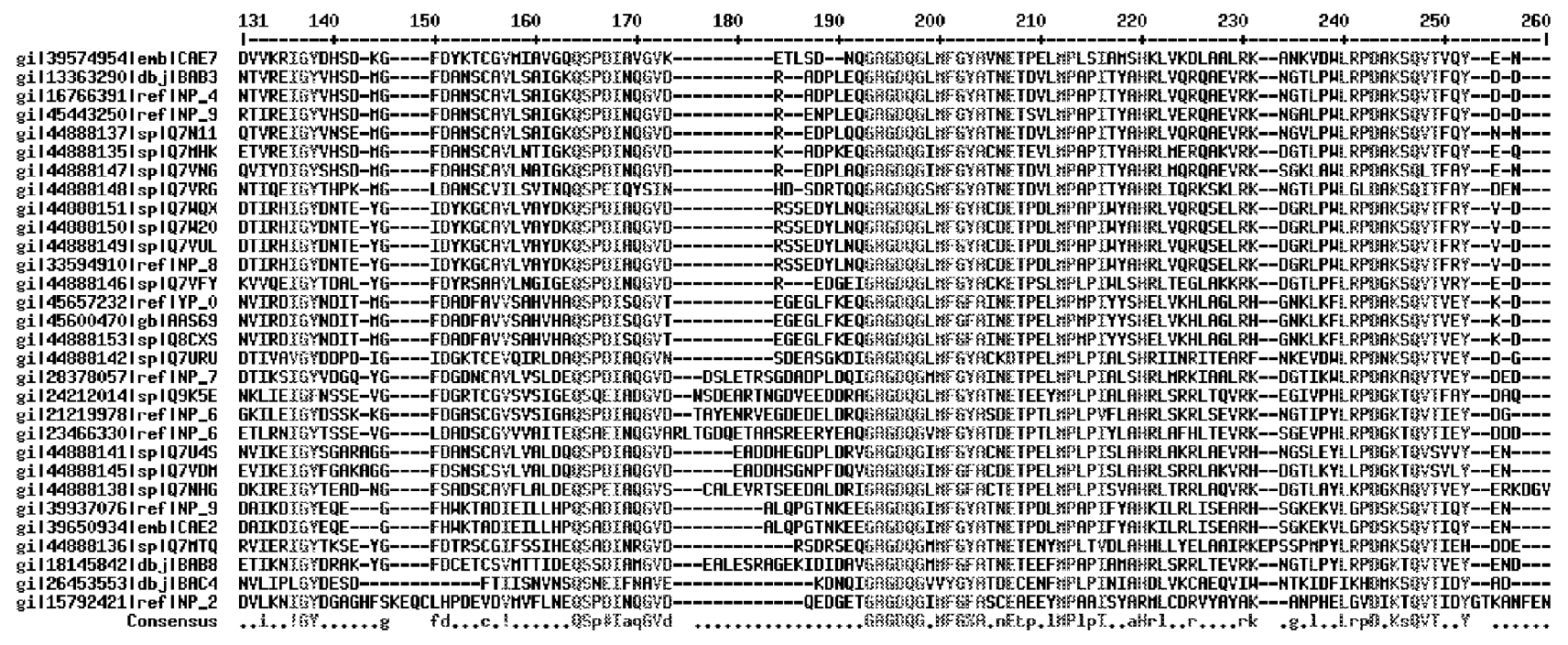

FIG. 4B: Continuation of alignment of MetK sequences from different microorganisms depicted in FIG. 4A.

Figure 4C:
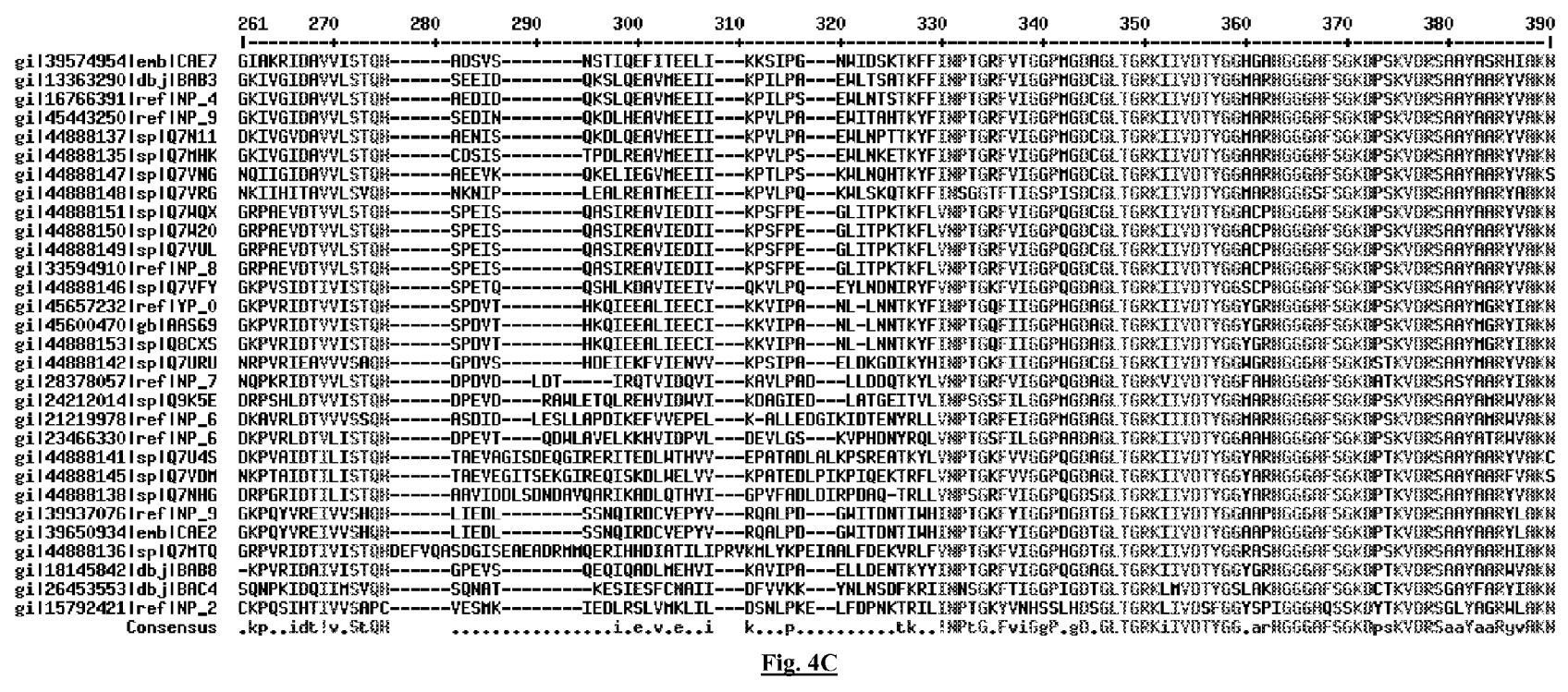

FIG. 4C: Continuation of alignment of MetK sequences from different microorganisms depicted in FIG. 4B.

Figure 4D:
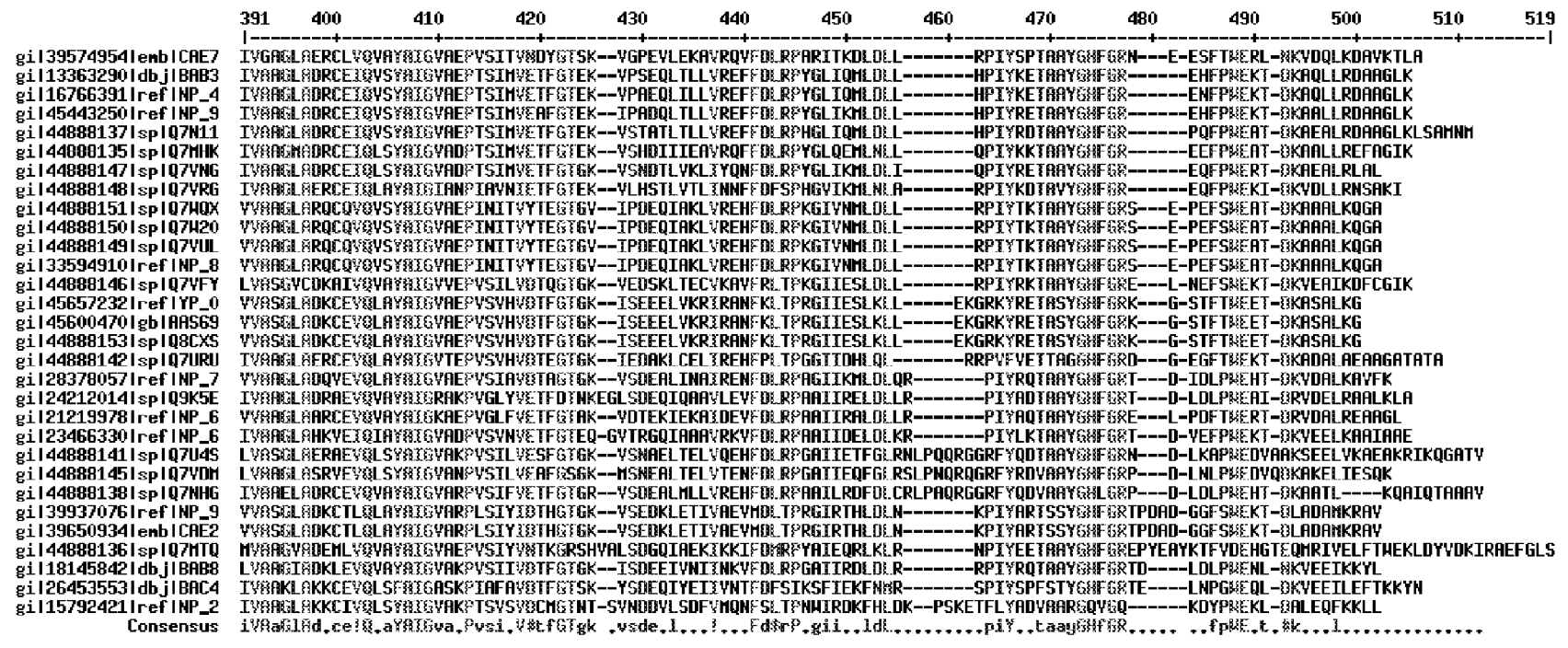

FIG. 4D: Continuation of alignment of MetK sequences from different microorganisms depcited in FIG. 4C.

FIG. 5: Amino acid replacements in the *E. coli* MetK protein. Amino acids above the coherent lines indicate the position and the replacing amino acid. The figure discloses SEQ ID NO: 137.

EXAMPLES

Example 1

Isolation of *E. coli* Mutants Containing Homoserine Transsuccinylase Enzymes which Show Decreased Feedback-Sensitivity Towards Methionine and S-Adenosylmethionine Isolation of *E. Coli* Strains Growing on α-Methylmethionine α-methylmethionine is a growth-inhibitory analogue of methionine producing an immediate effect on the growth rate of *E. coli* at very low concentrations (minimal inhibitory concentration of 1 µg/ml and minimal concentration for a maximal inhibition 5 µg/ml, Rowbury et al., 1968). Analogues can mimic methionine in the feedback inhibition of homoserine transsuccinylase and interfere with protein synthesis without being metabolized. Only mutant strains are able to grow in a medium containing the analogue.

*E. coli* was routinely grown aerobically at 37° C. in LB supplemented when needed with the appropriate antibiotic. The medium used for the α-methyl-methionine analogue resistant was a minimal medium containing (per liter): $K_2HPO_4$ 8 g, $Na_2HPO_4$ 2 g, $(NH_4)_2SO_4$ 0.75 g, $(NH_4)_2HPO_4$ 8 g, $NH_4Cl$ 0.13 g, citric acid 6.55 g, $MgSO_4$ 2.05 g, $CaCl_2$ 40 mg, $FeSO_4$ 40 mg, $MnSO_4$ 20 mg, $CoCl_2$ 8 mg, $ZnSO_4$ 4 mg, $(NH_4)_2Mo_2O_7$ 2.8 mg, $CuCl_2$ 2 mg, $H_3BO_3$ 1 mg. The pH was adjusted to 6.7 and the medium sterilized. Before use, glucose 10 g/l and thiamine 10 mg/l were added.

The α-methylmethionine powder commercialized by Sigma contains methionine traces. An overnight liquid culture of an *E. coli* strain (MG1655 ΔmetE) unable to grow without methionine addition was carried out to eliminate the methionine (coming from α-methylmethionine) from the minimal medium. The culture was centrifuged 10 minutes at 7000 rpm and the supernatant was filtered (Sartorius 0.2 µm). Agar 15 g/l was added to this minimal medium.

$1*10^8$ cells/ml from an overnight culture in minimal medium of the wild type strain (MG1655) were spread onto plates with minimal medium and α-methylmethionine after 4 washing steps in sterile water. The plates were incubated at 37° C. until colonies appeared.

Evidence of Mutations in the Coding Sequence of the metA Gene Coding for the Homoserine Transsuccinylase Enzyme.

Genomic DNA was prepared from 4 clones that grew on α-methyl-methionine at 4 mg/ml after cultivation in LB medium. The cell pellet was washed once with sterile water and resuspended in 30 µl of sterile water. Cells were broken by heating 5 minutes at. 95° C. and the debris were pelleted. The metA gene was PCR-amplified using Taq polymerase and the following primers:

```
MetAF (SEQ ID NO 3):
tcaccttcaacatgcaggctcgacattggc (4211759-4211788)

MetAR (SEQ ID NO 4):
ataaaaaaggcacccgaaggtgcctgaggt (4212857-4212828).
```

In three clones point mutations were detected which led to amino acid substitutions. In clone metA11 CAG was exchanged for a GAG leading to the replacement of Q by E. In metA*13 TTG was exchanged for a TTT leading to the replacement of L by F. In metA*14 GCG was exchanged for GTG leading to the replacement of A by V (see FIG. 2).

As can be seen from the alignment shown in FIG. 3 all three amino acid that are replaced are highly conserved in MetA proteins from various species.

The Mutated Homoserine Transsuccinylase Enzymes Show Decreased Feedback-Sensitivity Towards Methionine and S-adenosylmethionine.

The activity of homoserine transsuccinylase was determined in vitro *E. coli* strains carrying either wild-type or mutant-enzymes were cultured in rich medium with 2.5 g/l glucose and harvested at late log phase. Cells were resuspended in cold potassium phosphate buffer and sonicated on ice (Branson sonifier, 70W). After centrifugation, proteins contained in the supernatants were quantified (Bradford, 1976).

Ten µl of the extracts were incubated for 30 minutes at 25° C. with 30 mM homoserine and 4 mM succinyl-CoA. Methionine and/or S-adenosylmethionine were added as indicated. The succinylhomoserine produced by homoserine transsuccinylase enzymes was quantified by GC-MS after derivatization with tert-butyldimethylsilyltrifluoroacetamide (TBDMSTFA). L-Serine[1-13C] was included as an internal standard.

Results of homoserine transsuccinylase activities are reported in table 1 below:

TABLE 1

Specific activities of wild-type and mutant homoserine transsuccinylase enzymes upon the addition of inhibitors L-methionine and S-adenosyl methionine.

| Strain | Methionine mM | S-adenosylmethionine mM | Specific activity mUI/mg proteins |
|---|---|---|---|
| metA | 0 | 0 | 36.7 (100%) |
|  | 0 | 0.1 | 27.9 (76%) |
|  | 0 | 1 | 4.7 (12.8%) |
|  | 10 | 0 | 0.4 (1.1%) |
|  | 10 | 0.1 | 0.2 (0.5%) |
|  | 10 | 1 | 0.1 (0.3%) |
| metA*11 | 0 | 0 | 19.2 (100%) |
|  | 0 | 0.1 | 21.7 (113%) |
|  | 0 | 1 | 18.5 (96%) |
|  | 10 | 0 | 18.7 (97%) |
|  | 10 | 0.1 | 16.9 (88%) |
|  | 10 | 1 | 2.7 (14.1%) |
| metA*13 | 0 | 0 | 10.9 (100%) |
|  | 0 | 1 | 12.7 (117%) |
|  | 10 | 0 | 13.7 (126%) |
|  | 10 | 1 | 1.0 (9.2%) |
| metA*14 | 0 | 0 | 18.0 (100%) |
|  | 0 | 1 | 15.1 (83.9%) |
|  | 10 | 0 | 20.8 (116%) |
|  | 10 | 1 | 2.0 (11.1%) |

The mutated homoserine transsuccinylase enzymes thus show decreased feedback-sensitivity towards methionine and S-adenosylmethionine.

Example 2

Isolation of *E. Coli* Mutants Containing S-adenosylmethionine Synthetase Enzymes with Reduced Activity Isolation of *E. Coli* Strains Growing on Norleucine Norleucine is a growth-inhibitory analogue of methionine. At higher concentrations (50 mg/l) only mutant strains are able to grow in a medium containing the analogue. Most of these mutations map to the metK and metJ loci.

*E. coli* was routinely grown aerobically at 37° C. in LB supplemented when needed with the appropriate antibiotic. The medium used for the norleucine analogue resistant was a minimal medium containing (per liter): $K_2HPO_4$ 8 g, $Na_2HPO_4$ 2 g, $(NH_4)_2SO_4$ 0.75 g, $(NH_4)_2HPO_4$ 8 g, $NH_4Cl$ 0.13 g, citric acid 6.55 g, $MgSO_4$ 2.05 g, $CaCl_2$ 40 mg, $FeSO_4$ 40 mg, $MnSO_4$ 20 mg, $CoCl_2$ 8 mg, $ZnSO_4$ 4 mg, $(NH_4)_2Mo_2O_7$ 2.8 mg, $CuCl_2$ 2 mg, $H_3BO_3$ 1 mg. The pH was adjusted to 6.7 and the medium sterilized. Before use, glucose 10 g/l and thiamine 10 mg/l were added.

$1*10^8$ cells/ml from an overnight culture in minimal medium of the wild type strain (MG1655) were spread onto plates with minimal medium and norleucine (50 to 200 g/l) after 4 washing steps in sterile water. The plates were incubated at 37° C. until colonies appeared.

Evidence of Mutations in the Coding Sequence of the metK Gene Coding for the S-Adenosylmethionine Synthetase Enzyme Genomic DNA was prepared from cultures grown in LB liquid medium. The cell pellet was washed once with sterile water and resuspended in 30 μl of sterile water. Cells were broken by heating 5 minutes at 95° C. and the debris was extracted.

DNA was PCR-amplified with Taq polymerase using the following primers:

MetKpF:
(SEQ ID NO 05)
cccggctggaagtggcaacacg (3084372-3084393)

MetKR:
(SEQ ID NO 06)
gccggatgcggcgtgaacgcctatcc (3085956-3085931).

The metK gene was sequenced. In 10 clones point mutations were detected which led to amino acid substitutions. In clone metK*59/105 AGC was exchanged for AAC leading to the replacement of S by N (position 59) and GGC was exchanged for AGC leading to the replacement of G by S (position 105). In clone metK*105 GGC was exchanged for AGC leading to the replacement of G by S. In metK*115 GGC was exchanged for AGC leading to the replacement of G by S. In metK*137 CCT was replaced by CTT leading to the replacement of P by L. In metK*143 CAC was replaced by TAC leading to the replacement of H by Y. In metK*161/235 CGC was replaced by TGC leading to the replacement of R by C and CCA was replaced by TCA leading to the replacement of P by S. In metK*189 CAC was replaced by TAC leading to the replacement of H by Y. In metK*227 ACC was replaced by ATC leading to the replacement of T by I. In metK*253 GGC was replaced by GAC leading to the replacement of G by D. In metK*273 TCC was replaced by TTC leading to the replacement of S by F (see FIG. 5).

As can be seen from the alignment shown in FIG. 4 all amino acids that are replaced are conserved in MetK proteins from various species.

Recombinant S-adenosylmethionine Synthetase Enzymes with Decreased Activity

The activity of S-adenosylmethionine synthetase was determined in vitro. *E. coli* strains carrying either wild-type or mutant enzymes were cultured in minimal medium with 5 g/l glucose and harvested at late log phase. Cells were resuspended in cold potassium phosphate buffer and sonicated on ice (Branson sonifier, 70W). After centrifugation, proteins contained in the supernatants were quantified (Bradford, 1976).

One hundred μL of the extracts were incubated for 30 minutes at 37° C. with 10 mM methionine and 10 mM ATP. Potassium chloride was included to activate the enzymes. The adenosylmethionine produced by methionine adenosyltransferase enzymes was quantified by FIA-MS/MS.

Results of S-adenosylmethionine synthetase activities are reported in Table 2 below:

TABLE 2

S-adenosylmethionine synthetase activities (MAT) of WT and MetK* mutants.

| Strain | Mutations | MAT mUI/mg prot |
|---|---|---|
| WT | — | 7.5 |
| MetK* | H189Y | 0.6 |
| MetK* | S273F | 2.2 |
| MetK* | T227I | 4.9 |
| MetK* | G115S | 0.4 |
| MetK* | G105S | 2.8 |
| MetK* | H143T | 2.5 |
| MetK* | R161C + P235S | 0.7 |
| MetK* | S59N + G105S | 2.9 |

TABLE 2-continued

S-adenosylmethionine synthetase activities
(MAT) of WT and MetK* mutants.

| Strain | Mutations | MAT mUI/mg prot |
|---|---|---|
| MetK* | P137L | 1.2 |
| MetK* | G253D | 0.2 |

Example 3

Construction of *E. Coli* Strains for the Production of O-succinylhomoserine or Methionine by Overexpressing Altered Homoserine Transsuccinylase and Other Enzymes of the Methionine Biosynthesis Pathway For the construction of *E. coli* strains that allow the production of O-succinylhomoserine, a plasmid overexpressing the metL gene, coding for homoserine dehydrogenase and aspartokinase was introduced into strains harboring different alleles of metA. The plasmid overexpressing metL was constructed as follows:

The following two oligonucleotides were used:

```
MetLF with 32 bases (SEQ ID NO 7):
TATTCatgagtgtgattgcgcaggcaggggcg
``` with a region (lower case) homologous to the sequence (4127415 to 4127441) of the gene metL (sequence 4127415 to 4129847, reference sequence on the website http://genolist.pasteur.fr/Colibri/), a region (upper case) that together with the sequence pertaining to metL forms a restriction site for the enzyme BspHI (underlined),

```
MetBLAR with 38 bases (SEQ ID NO 8):
TATAAGCTTccataaacccgaaaacatgagtaccgggc
``` with a region (lower case) homologous to the sequence (4129894 to 4129866) of the gene metL a region (upper case) that harbors the restriction site HindIII.

The gene metL was amplified by PCR using the oligonucleotides MetLF and MetBLAR and the restriction sites BspHI and HindIII were introduced at the N- and C-terminus of the metL gene, respectively. The resulting PCR fragment was restricted by BspHI and HindIII and cloned into the vector pTRC99A (Stratagene) previously cut by NcoI and HindIII.

Plasmid preparations were examined for the presence of inserts of the correct size. The DNA sequence of metL was verified and the resulting plasmid pTRCmetL transformed into the strains harboring the alleles metA*11 and metA*13.

The activity of Homoserine dehydrogenase II (HDH) was determined in vitro. *E. coli* strains were cultured in minimal medium with 10 g·l$^{-1}$ glucose and harvested at late log phase. Cells were resuspended in cold potassium phosphate buffer and sonicated on ice (Branson sonifier, 70W). After centrifugation, proteins contained in the supernatants were quantified (Bradford, 1976).

Thirty µl of the extracts were incubated at 30° C. in a spectrophotometer, with 25 mM homoserine and 1 mM NADP$^+$. Potassium chloride was included to activate the enzyme. Since *E. coli* harbors a second gene encoding a homoserine dehydrogenase activity (thrA), threonine was added which inhibits this activity. The appearance of NADPH was monitored for 30 minutes at 340 nm.

Expression of metL from the Ptrc promoter increases drastically the HDH activity when compared to a similar strain with the plasmid.

TABLE 3

Homoserine dehydrogenase activities of the MetL protein in the MG1655 *E. coli* strain harbouring the metA*11 mutation with or without overexpressing metL from the Ptrc promoter.

| Strain | HDH in mUI/mg protein |
|---|---|
| MG1655 metA*11 | 11 |
| MG1655 metA*11 pTRCmetL | 117 |

In another application the methionine regulatory gene metJ was deleted in the strains harboring the metA*11, metA*13 and metA*14 alleles. To inactivate the metJ gene the homologous recombination strategy described by Datsenko & Wanner (2000) was used. This strategy allows the insertion of a chloramphenicol resistance cassette, while deleting most of the gene concerned. For this purpose 2 oligonucleotides were used:

```
DmetJF with 100 bases (SEQ ID NO 9):
Caggcaccagagtaaacattgtgttaatggacgicaatacatctggacat ctaaacttctttgcgtatagattgagcaaaCATATGAATATCCTCCTTAG
``` with a region (lower case) homologous to the sequence (4126216 to 4126137) of the gene metJ (sequence 4125658 to 4125975, reference sequence on the website http://genolist.pasteur.fr/Colibri/), a region (upper case) for the amplification of the chloramphenicol resistance cassette (reference sequence in Datsenko, K. A. & Wanner, B. L., 2000, PNAS, 97: 6640-6645),

```
DmetJR with 100 bases (SEQ ID NO 10):
tgacgtaggcctgataagcgtagcgcatcaggcgattccactccgcgccg ctcttttttgctttagtattcccacgtctcTGTAGGCTGGAGCTGCTTCG
``` with a region (lower case) homologous to the sequence (4125596 to 4125675) of the gene merJ a region (upper case) for the amplification of the chloramphenicol resistance cassette.

The oligonucleotides DmetJR and DmctJF were used to amplify the chloramphenicol resistance cassette from the plasmid pKD3. The PCR product obtained was then introduced by electroporation into the strain MG1655 (pKD46) in which the Red recombinase enzyme expressed permitted the homologous recombination. The chloramphenicol resistant transformants were then selected and the insertion of the resistance cassette was verified by a PCR analysis with the oligonucleotides MetJR and MetJF defined below. The strain retained is designated MG1655 (ΔmetJ::Cm) metA*.

MetJR (SEQ ID NO 11):
ggtacagaaaccagcaggctgaggatcagc (homologous to the sequence from 4125431 to 4125460).

MetBR (SEQ ID NO 12):
ttcgtcgtcatttaacccgctacgcactgc (homologous to the sequence from 4126305 to 4126276).

The chloramphenicol resistance cassette was then eliminated. The plasmid pCP20 carrying recombinase FLP acting at the FRT sites of the chloramphenicol resistance cassette was introduced into the recombinant strains by electroporation. After a series of cultures at 42° C., the loss of the chloramphenicol resistance cassette was verified by a PCR analysis with the same oligonucleotides as those used previously. The strains retained were designated MG1655 (ΔmetJ) metA*.

Subsequently the plasmid pTRCmetL harbouring the metL gene was introduced into these strains giving rise to ΔmetJ metA*11 pTRCmetL, ΔmetJ metA*13 pTRCmetL and ΔmetJ metA*14 pTRCmetL.

Example 4

Construction of Homoserine Succinyltransferase Alleles Expressing Enzymes with Further Reduced Feed-Back Sensitivity To further reduce the sensitivity of homoserine transsuccinylase to its feed-back inhibitors methionine and SAM other metA mutants were constructed by site directed mutagenesis.

Initially the metA and metA*11 allele were cloned into the vector pTRC99A (Stratagene). The following two oligonucleotides were used:

MetA-NcoI with 49 bases (SEQ ID NO 13):
TATTAAATTA<u>CCatgg</u>caccgattcgtgtgccggacgagctacccgccg with a region (lower case) homologous to the sequence (4211862 to 4211892) of the gene metA (sequence 4211859 to 4212788, reference sequence on the website http://genolist.pasteur.fr/Colibri/), a region (upper case) that together with the sequence pertaining to metA forms a restriction site for the enzyme NcoI (underlined), MetA-EcoRJ with 47 bases (SEQ ID NO 14):
TATTAAATTA<u>Gaattc</u>cgactatcacagaagattaatccagcgttgg with a region (lower case) homologous to the sequence (4212804 to 42127774) of the gene metA a region (upper case) that harbors the restriction site EcoRI.

The alleles metA and metA*11 were amplified by PCR using oligonucleotides MctAF and MetAR and the restriction sites NcoI and EcoRJ were introduced at the N- and C-terminus of the metA gene, respectively. The resulting PCR fragments were restricted by NcoI and EcoRI and cloned into the vector pTRC99A (Stratagene) previously cut by NcoI and EcoRI.

Plasmid preparations were examined for the presence of inserts of the correct size and the DNA sequences of metA and metA*11 were verified by sequencing.

Enzymatic analysis of the clones expressing metA and metA*11 gave vary low MetA activity. We presumed that introducing an alanine between amino acid 1M and 2P, which was required for cloning of metA into the vector pTRC99A, caused this loss of activity. Therefore using site directed mutagenesis (Stratagene) the alanine was eliminated using the oligonucleotides:

metA-alaF (AflIII) (SEQ ID NO 15): cacacaggaaacagac-catgccgatacgtgtgccggacgagctaccc metA-alaR (AflIII) (SEQ ID NO 16): gggtagctcgtccggca-cacgtatcggcatggtctgtttcctgtgtg Subsequently the mutants metA*15 (A27V+Q64E), metA*16 (Q64D) and metA*17 (A27V+Q64D) were constructed by site directed mutagenesis (Stratagene) using the corrected metA sequence as matrix. For the construction of pTRCmetA*15 (A27V+Q64E) the following oligonucleotides were used:

MetAA28VF (XbaI) (SEQ ID NO 17):
Gtgatgacaacttctagagtgtctggtcaggaaattcgtcc

MetAA28VR (XbaI) (SEQ ID NO 18):
Ggacgaatttcctgaccagacactctagaagttgtcatcac and pTRCmetA*11 as matrix.

For the construction of pTRCmetA*16 (Q64D) the following oligonucleotides were used:

MetAQ64DF (EcoRV) (SEQ ID NO 19):
Gctttcaaactcacctttggatgtcgatatccagctgttgc

MetAQ64DR (EcoRV)
                                    (SEQ ID NO 20)
gcaacagctggatatcgacatccaaaggtgagtttgaaagc and pTRCmetA as matrix.

For the construction of pTRCmetA*17 (A27V+Q64D) the following oligonucleotides were used: MetAA28VF (XbaI) (SEQ ID NO. 17) and MetAA28VR (XbaI) (SEQ ID NO 18); and pTRCmetA*16 as matrix.

Plasmids were verified by sequencing.

To transfer the alleles metA*15, metA*16 and metA*17 onto the metA locus on the chromosome, a metA deletion was constructed in the ΔmetJ background applying the same strategy used for the metJ deletion. The following oligonucleotides were used for deleting metA:

DmetAF (4211866-4211945)
                                    (SEQ ID NO 21)
ttcgtgtgccggacgagctacccgccgtcaatttcttgcgtgaagaaaac gtctttgtgatgacaacttctcgtgcgtctTGTAGGCTGGAGCTGCTTCG DmetAR (4212785-4212706)
                                    (SEQ ID NO 22)
Atccagcguggattcatgtgccgtagatcgtatggcgtgatctggtagac gtaatagttgagccagttggtaaacagtaCATATGAATATCCTCCTTAG The region indicated in lower case corresponds to the sequence between metA and yjaB. The region in upper case is used to amplify the kanamycin resistance cassette (Datsenko & Wanner, 2000). (Numbers in parentheses correspond to the reference sequence on the website http://genolist.pasteur.fr/Colibri/).

The resulting deletion was verified using the following oligonucleotides. (Numbers in parentheses correspond to the reference sequence on the website http://genolist.pasteur.fr/Colibri/).

MetAF (SEQ ID NO 3) and MetAR (SEQ ID NO 4).

The resulting strain DmetJ DmetA was used to introduce the alleles metA*15, metA*16 and metA*17 onto the chromosome. For this purpose the plasmid pKD46 was introduced into the strain DmetJ DmetA (Datsenko and Wanner, 2000). The alleles were amplified from the vectors pTRCmetA*15, pTRCmetA*16 and pTRCmetA*17 using the following oligonucleotides:

MetArcF (4211786-4211884)
(SEQ ID NO 23)
Ggcaaattttctggttatcttcagctatctggatgtctaaacgtataagc gtatgtagtgaggtaatcaggttatgccgattcgtgtgccggacgagc

MetArcR (4212862-4212764)
(SEQ iD NO 24)
Cggaaataaaaaaggcacccgaaggtgcctgaggtaaggtgctgaatcgc ttaacgatcgactatcacagaagattaatccagcgtggattcatgtgc

The sequence in bold is homologous to the sequence of the gene metA; the rest of the sequence is adjacent to metA.

For verification by PCR the following oligonucleotides were used: MetAF (SEQ ID NO 3) and MetAR (SEQ ID NO 4).

As described above, the resulting strains were cultivated in minimal medium, crude extracts were prepared and the activity of MetA was determined. As can be seen from Tab. 4 the newly constructed alleles are less sensitive to the inhibition by methionine and SAM than the alleles described above. Especially interesting is the allele metA*15 with high intrinsic activity that cannot be inhibited by SAM and methionine.

TABLE 4

Homoserinetranssuccinylase activities of MetA mutants in absence and presence of 100 mM methionine and 1 mM SAM. Percentages values in parentheses indicate the amount of remaining activity upon inhibition.

| Strain | Methionine mM | S-adenosyl-methionine mM | Specific activity mUI/mg proteins |
|---|---|---|---|
| metA*11 ΔmetJ | 0 | 0 | 492 (100%) |
|  | 100 | 1 | 14 (2.8%) |
| metA*11rc ΔmetJ | 0 | 0 | 531 (100%) |
|  | 100 | 1 | 18 (3.4%) |
| metA*15rc ΔmetJ | 0 | 0 | 610 (100%) |
|  | 100 | 1 | 733 (100%) |
| metA*16rc ΔmetJ | 0 | 0 | 294 (100%) |
|  | 100 | 1 | 143 (48.6%) |
| metA*17rc ΔmetJ | 0 | 0 | 436 (100%) |
|  | 100 | 1 | 305 (70%) |

Example 5

Construction of E. coli Strains for the Production of O-Succinyl Homoserine or Methionine by Combining Feed-Back Resistant MetA Alleles with MetK Alleles with Decreased Activity In order to transfer the recombinant metK alleles into strains harboring feedback resistant metA alleles, a kanamycin resistance cassette was introduced between the metK and galP gene.

To introduce the cassette the homologous recombination strategy described by Datsenko & Wanner (2000) is used. This strategy allows the insertion of a kanamycin resistance cassette, while deleting most of the gene concerned. For this purpose 2 oligonucleotides are used:

DMetKFscr with 100 bases (SEQ ID NO 25):
ccgcccgcacaataacatcattcttcctgatcacgtttcaccgcagatta tcatcacaactgaaaccgattacaccaaccTGTAGGCTGGAGCTGCTTCG with
a region (lower case) homologous to the sequence of the region, between metK and galP (sequence 3085964 to 3086043, reference sequence on the website http://genolist.pasteur.fr/Colibri/),
a region (upper case) for the amplification of the kanamycin resistance cassette (reference sequence in Datsenko, K. A. & Wanner, B. L., 2000, PNAS, 97: 6640-6645), DmetKRscr with 100 bases (SEQ ID NO 26):
gagttatatcatcatagattaaacgctgttatctgcaattaagactttac tgaaaagaaatgtaacaactgtgaaaaccgCATATGAATATCCTCCTTAG with
a region (lower case) homologous to the region between, the gene metK and galP (3086162 to 3086083)
a region (upper case) for the amplification of the kanamycin resistance cassette.

The oligonucleotides DMetKFscr and DmetKRscr are used to amplify the kanamycin resistance cassette from the plasmid pKD4. The PCR product obtained is then introduced by electroporation into the strain MG1655 (pKD46) in which the expressed Red recombinase enzyme allows the homologous recombination. The kanamnycin resistant transformants are then selected and the insertion of the resistance cassette is verified by a PCR analysis with the oligonucleotides MetKFscr and MetKRscr defined below. The strain retained is designated MG1655 (metK, Kin).

MetKFscr (SEQ ID NO 27): gcgcccatacggtctgattcagatgctgg (homologous to the sequence from 3085732 to 3085760).

MctKRscr (SEQ ID NO 28): gcgccagcaattacaccgatatccaggcc (homologous to the sequence from 3086418 to 3086390).

To transfer the metK-alleles, the method of phage P1 transduction is used. The protocol followed is implemented in 2 steps with the preparation of the phage lysate of the strain MG1655 (metK, Km) and then transduction into strain MG1655 ΔmetJ metA*11 pTRCmetL.

The construction of the strain (metK, Kin) is described above.

Preparation of Phage Lysate P1:
Inoculation with 100 μl of an overnight culture of the strain MG1655 (metK, Km) of 10 ml of LB+Km 50 μg/ml+ glucose 0.2%+CaCl$_2$ 5 mM
Incubation for 30 min at 37° C. with shaking
Addition of 100 μl of phage lysate P1 prepared on the wild strain MG1655 (about 1·10$^9$ phase/ml)
Shaking at 37° C. for 3 hours until all the cells were lysed
Addition of 200 μl chloroform and vortexing
Centrifugation for 10 min at 4500 g to eliminate cell debris
Transfer of supernatant to a sterile tube and addition of 200 μl chloroform
Storage of lysate at 4° C.
Transduction
Centrifuging for 10 min at 1500 g of 5 ml of an overnight culture of the strain MG1655 ΔmetJ metA*11 pTRC-metL in LB medium
Suspension of the cell pellet in 2.5 ml of 10 mM MgSO$_4$, 5 mM CaCl$_2$
Control tubes: 100 μl cells
100 μl phages P1 of strain MG1655 (ΔmetK, Km)

Test tube: 100 µl of cells+100 µl of phages P1 of the strain MG1655 (ΔmetK, Km)
Incubation for 30 min at 30° C. without shaking
Addition of 100 µl of 1 M sodium citrate in each tube and vortexing
Addition of 1 ml of LB
Incubation for 1 hour at 37° C. with shaking
Spreading on dishes LB+Km 50 µg/ml after centrifuging of tubes for 3 min at 7000 rpm
Incubation at 37° C. overnight.
Verification of the Strain The kanamycin resistant transformants are then selected and the insertion of the region containing (metK, Km) is verified by a PCR analysis with the oligonucleotides MetKFscr and MetKRscr. The strain retained is designated MG1655 ΔmetJ metA*11 pTRCmetL metK*.

The kanamycin resistance cassette can then be eliminated. The plasmid pCP20 carrying FLP recombinase acting at the FRT sites of the kanamycin resistance cassette is then introduced into the recombinant sites by electroporation. After a series of cultures at 42° C., the loss of the kanamycin resistance-cassette is verified by a PCR analysis with the same oligonucleotides as used previously (MetKFscr and MetKRscr).

Example 6

Fermentation of E. Coli Production Strains and Analysis of Yield

Production strains were initially analyzed in small Erlenmeyer flask cultures using modified M9 medium (Anderson, 1946, Proc. Natl. Acad. Sci. USA 32:120-128) that was supplemented with 5 g/l MOPS and 5 g/l glucose. Carbenicillin was added if necessary at a concentration of 100 mg/l. An overnight culture was used to inoculate a 30 ml culture to an OD600 of 0.2. After the culture had reached an OD600 of 4.5 to 5, 1.25 ml of a 50% glucose solution and 0.75 ml of a 2M MOPS (pH 6.9) were added and culture was agitated for 1 hour. Subsequently IPTG was added if necessary.

Extracellular metabolites were analyzed during the batch: phase. Amino acids were quantified by HPLC after OPA/Fmoc derivatization and other relevant metabolites were analysed using GC-MS after silylation.

The following results were obtained for the strains MG1655, MG1655 pTRCmetL MG1655 metA*11 pTRCmetL, MG1655 metA*13 pTRCmetL, MG1655 metA*11 ΔmetJ pTRCmetL, MG1655 metA*11 ΔmetJ pTRCmetL metK*H143Y.

To further boost the production of homoserine the aspartokinase/homoserine a thrA* allele with reduced feed-back resistance to threonine is expressed from the plasmid pCL1920 (Lerner & Inouyc, 1990, NAR 18, 15 p 4631) using the promoter Ptrc. For the construction of plasmid pME 107 thrA was PCR amplified from genomic DNA using the following oligonucleotides:

```
BspH1thrA (SEQ ID NO 29):
ttaTCATGAgagtgttgaagttcggcggtacatcagtggc

SmaIthrA (SEQ ID NO 30):
ttaCCCGGGccgccgccccgagcacatcaaacccgacgc
```

The PCR amplified fragment is cut with the restriction enzymes BspHI and SmaI and cloned into the NcoI/SmaI sites of the vector pTRC99A (Stratagene). For the expression from a low copy vector the plasmid pME101 is constructed as follows. The plasmid pCL1920 is PCR amplified using the oligonucleotides PME101F and PME101R and the BstZ171-XmnI fragment from the vector pTRC99A harboring the lacI gene and the Ptrc promoter is inserted into the amplified vector. The resulting vector and the vector harboring the thrA gene are restricted by ApaI and SmaI and the thrA containing fragment is cloned into the vector pME101. To relieve ThrA from feed-back inhibition the mutation F318S is introduced by site-directed mutagenesis (Stratagene) using the oligonucleotides ThrAF F318S for and ThrAR F318S, resulting in the vector pME107. The vector pME107 was introduced into the ΔmetJ metA*11 strains with differing metK* alleles.

```
PME101F (SEQ ID NO 31):
Ccgacagtaagacgggtaagcctg

PME101R (SEQ ID NO 32):
Agcttagtaaagccctcgctag

ThrAF F318S (SmaI) (SEQ ID NO 33):
Ccaatctgaaaacatggcaatgtccagcgtttctggcccggg

ThrAR F318S (SmaI) (SEQ ID NO 34):
Cccgggccagaaacgctggacattgccatgttattcagattgg
```

Strains that produced substantial amounts of metabolites of interest were subsequently tested under production conditions in 300 ml fermentors (DASGIP) using a fed batch protocol.

For this purpose the fermentor was filled with 145 ml of modified minimal medium and inoculated with 5 ml of preculture to an optical density (OD600 nm) between 0.5 and 1.2.

TABLE 5

Specific concentrations of extracellular metabolites (mmol/g dry weight) after batch (Erlenmeyer flask) fermentation.

| Product (mmol/g) Strain | MG1655 | MG1655 metA*11 | MG1655 pTRCmetL | MG1655 metA*11 pTRCmetL | MG1655 metA*13 pTRCmetL | MG1655 metA*11 pTRCmetL | MG1655 metA*11 metJ pTRCmetL | MG1655 metA*11 metJ pTRCmetL metK* H143Y |
|---|---|---|---|---|---|---|---|---|
| O-succinyl homoserine | >0.01 | 0.02 | 0.05 | 0.31 | 0.27 | 0.03 | 0.03 | 0.39 |
| homoserine | 0.01 | ND | 0.17 | 0.07 | 0.09 | 0.01 | ND | 0.01 |
| threonine | >0.01 | ND | 0.37 | 0.6 | 0.59 | 0.01 | 0.02 | 0.13 |
| methionine | >0.01 | >0.01 | >0.01 | 0.06 | 0.03 | 0.2 | 0.26 | 0.31 |
| isoleucine | ND | ND | 0.01 | 0.01 | 0.02 | 0.14 | 0.22 | 0.49 |

ND not detected.

The temperature of the culture was maintained constant at 37° C. and the pH was permanently adjusted to values between 6.5 and 8 using an NH₄OH solution. The agitation rate was maintained between 200 and 300 rpm during the batch phase and was increased to up to 1000 rpm at the end of the fed-batch phase. The concentration of dissolved oxygen was maintained at values between 30 and 40% saturation by using a gas controller. When the optical density reached a value between three and five the fed-batch was started with an initial flow rate between 0.3 and 0.5 ml/h and a progressive increase up to flow rate values between 2.5 and 3.5 ml/h. At this point the flow rate was maintained constant for 24-o 48 hours. The media of the fed was based on minimal media containing glucose at concentrations between 300 and 500 g/l.

Tab. 6 shows methionine concentrations for the strains ΔmetJ metA*11 pME107 metK*H143Y and ΔmetJ metA*11 pME107 metK*T227I compared to the reference strain ΔmetJ metA*11 pME107 after about 75 h of operation. Both strains harboring the metK* alleles attain an increased methionine concentration when compared to the reference strain. Thus the metK mutations confer an industrial advantage on methionine production by increasing the productivity of the strains.

TABLE 6

Methionine production of the reference strain ΔmetJ metA*11 pME107 and two strains harboring the metK* mutations after indicated time of operation including batch and fed-batch.

| Strain | Time of operation | Methionine produced |
|---|---|---|
| ΔmetJ metA*11 pME107 | 77 h | 75.5 mM |
| ΔmetJ metA*11 pME107 metK*H143Y | 74.8 h | 87.3 mM |
| ΔmetJ metA*11 pME107 metK*T227I | 75 h | 95.0 mM |

What is claimed is:

1. A method for the preparation of methionine, its precursors or products derived thereof, in a fermentative process with a microorganism where L-homoserine is converted into O-succinylhomoserine with a homoserine transsuccinylase comprising the step of culturing the microorganism on an appropriate culture medium and recovering methionine, its precursors or products derived thereof once produced, wherein the homoserine transsuccinylase is a mutated homoserine transsuccinylase with reduced sensitivity for the feedback inhibitors S-adenosylmethionine and methionine, wherein the homoserine transsuccinylase has the sequence as shown in SEQ ID NO:1 and wherein the conserved amino acid Q at position 64 is replaced with a glutamic acid (E) or an aspartic acid (D).

2. The method as claimed in claim 1, wherein the microorganisms comprise a S-adenosylmethionine synthetase enzyme having the sequence show in SEQ ID NO: 2 with reduced S-adenosylmethionine synthetase enzymatic activity, and wherein the conserved amino acid H at position 143 is replaced with a tyrosine (Y).

3. The method as claimed in claim 1, wherein the microorganism is selected from the group consisting of prokaryotes and eukaryotes.

4. The method as claimed in claim 3 wherein the prokaryotic microorganism is *Escherichia coli* or *Coryneybacterium glutamicum*.

5. The method of claim 2, wherein the S-adenosylmethionine synthetase comprises the amino acid sequence of SEQ ID NO: 2 having a substitution at His 143.

* * * * *

SEQUENCE LISTING

<160> NUMBER OF SEQ ID NOS: 138

<210> SEQ ID NO 1
<211> LENGTH: 309
<212> TYPE: PRT
<213> ORGANISM: Escherichia coli

<400> SEQUENCE: 1

Met Pro Ile Arg Val Pro Asp Glu Leu Pro Ala Val Asn Phe Leu Arg
1               5                   10                  15

Glu Glu Asn Val Phe Val Met Thr Thr Ser Arg Ala Ser Gly Gln Glu
            20                  25                  30

Ile Arg Pro Leu Lys Val Leu Ile Leu Asn Leu Met Pro Lys Lys Ile
        35                  40                  45

Glu Thr Glu Asn Gln Phe Leu Arg Leu Leu Ser Asn Ser Pro Leu Gln
    50                  55                  60

Val Asp Ile Gln Leu Leu Arg Ile Asp Ser Arg Glu Ser Arg Asn Thr
65                  70                  75                  80

Pro Ala Glu His Leu Asn Asn Phe Tyr Cys Asn Phe Glu Asp Ile Gln
                85                  90                  95

Asp Gln Asn Phe Asp Gly Leu Ile Val Thr Gly Ala Pro Leu Gly Leu
            100                 105                 110

Val Glu Phe Asn Asp Val Ala Tyr Trp Pro Gln Ile Lys Gln Val Leu
        115                 120                 125

Glu Trp Ser Lys Asp His Val Thr Ser Thr Leu Phe Val Cys Trp Ala
    130                 135                 140

Val Gln Ala Ala Leu Asn Ile Leu Tyr Gly Ile Pro Lys Gln Thr Arg
145                 150                 155                 160

Thr Glu Lys Leu Ser Gly Val Tyr Glu His His Ile Leu His Pro His
                165                 170                 175

Ala Leu Leu Thr Arg Gly Phe Asp Asp Ser Phe Leu Ala Pro His Ser
            180                 185                 190

Arg Tyr Ala Asp Phe Pro Ala Ala Leu Ile Arg Asp Tyr Thr Asp Leu
        195                 200                 205

Glu Ile Leu Ala Glu Thr Glu Glu Gly Asp Ala Tyr Leu Phe Ala Ser
    210                 215                 220

Lys Asp Lys Arg Ile Ala Phe Val Thr Gly His Pro Glu Tyr Asp Ala
225                 230                 235                 240

```
Gln Thr Leu Ala Gln Glu Phe Arg Asp Val Glu Ala Gly Leu Asp
                245                 250                 255

Pro Asp Val Pro Tyr Asn Tyr Phe Pro His Asn Asp Pro Gln Asn Thr
            260                 265                 270

Pro Arg Ala Ser Trp Arg Ser His Gly Asn Leu Leu Phe Thr Asn Trp
        275                 280                 285

Leu Asn Tyr Tyr Val Tyr Gln Ile Thr Pro Tyr Asp Leu Arg His Met
290                 295                 300

Asn Pro Thr Leu Asp
305

<210> SEQ ID NO 2
<211> LENGTH: 384
<212> TYPE: PRT
<213> ORGANISM: Escherichia coli

<400> SEQUENCE: 2

Met Ala Lys His Leu Phe Thr Ser Glu Ser Val Ser Glu Gly His Pro
1               5                   10                  15

Asp Lys Ile Ala Asp Gln Ile Ser Asp Ala Val Leu Asp Ala Ile Leu
            20                  25                  30

Glu Gln Asp Pro Lys Ala Arg Val Ala Cys Glu Thr Tyr Val Lys Thr
        35                  40                  45

Gly Met Val Leu Val Gly Gly Glu Ile Thr Thr Ser Ala Trp Val Asp
    50                  55                  60

Ile Glu Glu Ile Thr Arg Asn Thr Val Arg Glu Ile Gly Tyr Val His
65                  70                  75                  80

Ser Asp Met Gly Phe Asp Ala Asn Ser Cys Ala Val Leu Ser Ala Ile
                85                  90                  95

Gly Lys Gln Ser Pro Asp Ile Asn Gln Gly Val Asp Arg Ala Asp Pro
            100                 105                 110

Leu Glu Gln Gly Ala Gly Asp Gln Gly Leu Met Phe Gly Tyr Ala Thr
        115                 120                 125

Asn Glu Thr Asp Val Leu Met Pro Ala Pro Ile Thr Tyr Ala His Arg
    130                 135                 140

Leu Val Gln Arg Gln Ala Glu Val Arg Lys Asn Gly Thr Leu Pro Trp
145                 150                 155                 160

Leu Arg Pro Asp Ala Lys Ser Gln Val Thr Phe Gln Tyr Asp Asp Gly
                165                 170                 175

Lys Ile Val Gly Ile Asp Ala Val Val Leu Ser Thr Gln His Ser Glu
            180                 185                 190

Glu Ile Asp Gln Lys Ser Leu Gln Glu Ala Val Met Glu Glu Ile Ile
        195                 200                 205

Lys Pro Ile Leu Pro Ala Glu Trp Leu Thr Ser Ala Thr Lys Phe Phe
    210                 215                 220

Ile Asn Pro Thr Gly Arg Phe Val Ile Gly Gly Pro Met Gly Asp Cys
225                 230                 235                 240

Gly Leu Thr Gly Arg Lys Ile Ile Val Asp Thr Tyr Gly Gly Met Ala
                245                 250                 255

Arg His Gly Gly Gly Ala Phe Ser Gly Lys Asp Pro Ser Lys Val Asp
            260                 265                 270

Arg Ser Ala Ala Tyr Ala Ala Arg Tyr Val Ala Lys Asn Ile Val Ala
        275                 280                 285

Ala Gly Leu Ala Asp Arg Cys Glu Ile Gln Val Ser Tyr Ala Ile Gly
```

|  |  |  |  |  |  |  |  |  |  |  |  |  |  |  |
|---|---|---|---|---|---|---|---|---|---|---|---|---|---|---|
|  |  |  | 290 |  |  |  | 295 |  |  |  | 300 |  |  |  |

Val Ala Glu Pro Thr Ser Ile Met Val Glu Thr Phe Gly Thr Glu Lys
305                 310                 315                 320

Val Pro Ser Glu Gln Leu Thr Leu Leu Val Arg Glu Phe Phe Asp Leu
             325                 330                 335

Arg Pro Tyr Gly Leu Ile Gln Met Leu Asp Leu Leu His Pro Ile Tyr
             340                 345                 350

Lys Glu Thr Ala Ala Tyr Gly His Phe Gly Arg Glu His Phe Pro Trp
         355                 360                 365

Glu Lys Thr Asp Lys Ala Gln Leu Leu Arg Asp Ala Ala Gly Leu Lys
     370                 375                 380

```
<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
tcaccttcaa catgcaggct cgacattggc                                    30

<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ataaaaaagg cacccgaagg tgcctgaggt                                    30

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
cccggctgga agtggcaaca cg                                            22

<210> SEQ ID NO 6
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gccggatgcg gcgtgaacgc ctatcc                                        26

<210> SEQ ID NO 7
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
```
tattcatgag tgtgattgcg caggcagggg cg                                    32

<210> SEQ ID NO 8
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
tataagcttc cataaacccg aaaacatgag taccgggc                              38

<210> SEQ ID NO 9
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9
caggcaccag agtaaacatt gtgttaatgg acgtcaatac atctggacat ctaaacttct      60
ttgcgtatag attgagcaaa catatgaata tcctccttag                           100

<210> SEQ ID NO 10
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10
tgacgtaggc ctgataagcg tagcgcatca ggcgattcca ctccgcgccg ctcttttttg      60
ctttagtatt cccacgtctc tgtaggctgg agctgcttcg                           100

<210> SEQ ID NO 11
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
ggtacagaaa ccagcaggct gaggatcagc                                      30

<210> SEQ ID NO 12
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
ttcgtcgtca tttaacccgc tacgcactgc                                      30

<210> SEQ ID NO 13
<211> LENGTH: 49
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 13
tattaaatta ccatggcacc gattcgtgtg ccggacgagc tacccgccg         49

<210> SEQ ID NO 14
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
tattaaatta gaattccgac tatcacagaa gattaatcca gcgttgg           47

<210> SEQ ID NO 15
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
cacacaggaa acagaccatg ccgatacgtg tgccggacga gctaccc           47

<210> SEQ ID NO 16
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
gggtagctcg tccggcacac gtatcggcat ggtctgtttc ctgtgtg           47

<210> SEQ ID NO 17
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
gtgatgacaa cttctagagt gtctggtcag gaaattcgtc c                 41

<210> SEQ ID NO 18
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
ggacgaattt cctgaccaga cactctagaa gttgtcatca c                 41

<210> SEQ ID NO 19
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
gctttcaaac tcacctttgg atgtcgatat ccagctgttg c         41

<210> SEQ ID NO 20
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
gcaacagctg gatatcgaca tccaaaggtg agtttgaaag c         41

<210> SEQ ID NO 21
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 21
ttcgtgtgcc ggacgagcta cccgccgtca atttcttgcg tgaagaaaac gtctttgtga    60
tgacaacttc tcgtgcgtct tgtaggctgg agctgcttcg                         100

<210> SEQ ID NO 22
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 22
atccagcgtt ggattcatgt gccgtagatc gtatggcgtg atctggtaga cgtaatagtt    60
gagccagttg gtaaacagta catatgaata tcctccttag                         100

<210> SEQ ID NO 23
<211> LENGTH: 98
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
ggcaaatttt ctggttatct tcagctatct ggatgtctaa acgtataagc gtatgtagtg    60
aggtaatcag gttatgccga ttcgtgtgcc ggacgagc                            98

<210> SEQ ID NO 24
<211> LENGTH: 99
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
cggaaataaa aaaggcaccc gaaggtgcct gaggtaaggt gctgaatcgc ttaacgatcg    60
actatcacag aagattaatc cagcgttgga ttcatgtgc                           99

<210> SEQ ID NO 25
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 25
ccgcccgcac aataacatca ttcttcctga tcacgtttca ccgcagatta tcatcacaac      60
tgaaaccgat tacaccaacc tgtaggctgg agctgcttcg                          100

<210> SEQ ID NO 26
<211> LENGTH: 100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 26
gagttatatc atcatagatt aaacgctgtt atctgcaatt aagactttac tgaaaagaaa      60
tgtaacaact gtgaaaaccg catatgaata tcctccttag                          100

<210> SEQ ID NO 27
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
gcgcccatac ggtctgattc agatgctgg                                       29

<210> SEQ ID NO 28
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
gcgccagcaa ttacaccgat atccaggcc                                       29

<210> SEQ ID NO 29
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
ttatcatgag agtgttgaag ttcggcggta catcagtggc                           40

<210> SEQ ID NO 30
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
ttacccgggc cgccgccccg agcacatcaa acccgacgc            39

<210> SEQ ID NO 31
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
ccgacagtaa gacgggtaag cctg            24

<210> SEQ ID NO 32
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
agcttagtaa agccctcgct ag            22

<210> SEQ ID NO 33
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
ccaatctgaa taacatggca atgtccagcg tttctggccc ggg            43

<210> SEQ ID NO 34
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
cccgggccag aaacgctgga cattgccatg ttattcagat tgg            43

<210> SEQ ID NO 35
<211> LENGTH: 7
<212> TYPE: PRT
<213> ORGANISM: Escherichia coli
<220> FEATURE:
<221> NAME/KEY: MOD_RES
<222> LOCATION: (1)..(1)
<223> OTHER INFORMATION: Glu, Asp, Thr, Ser or Leu
<220> FEATURE:
<221> NAME/KEY: MOD_RES
<222> LOCATION: (2)..(2)
<223> OTHER INFORMATION: Asp, Ser, Lys, Gln, Glu, Ala or Arg
<220> FEATURE:
<221> NAME/KEY: MOD_RES
<222> LOCATION: (3)..(3)
<223> OTHER INFORMATION: Arg, Glu or Asp
<220> FEATURE:
<221> NAME/KEY: MOD_RES
<222> LOCATION: (5)..(5)
<223> OTHER INFORMATION: Tyr, Ile, Phe, Ala, Lys, Ser or Val
<220> FEATURE:
<221> NAME/KEY: MOD_RES
<222> LOCATION: (6)..(6)
<223> OTHER INFORMATION: His, Ser, Asn, Gly, Thr or Arg

```
<400> SEQUENCE: 35

Xaa Xaa Xaa Ala Xaa Xaa Gln
1               5

<210> SEQ ID NO 36
<211> LENGTH: 7
<212> TYPE: PRT
<213> ORGANISM: Escherichia coli

<400> SEQUENCE: 36

Thr Ser Arg Ala Ser Gly Gln
1               5

<210> SEQ ID NO 37
<211> LENGTH: 8
<212> TYPE: PRT
<213> ORGANISM: Escherichia coli
<220> FEATURE:
<221> NAME/KEY: MOD_RES
<222> LOCATION: (1)..(1)
<223> OTHER INFORMATION: Gly, Ala or Ser
<220> FEATURE:
<221> NAME/KEY: MOD_RES
<222> LOCATION: (2)..(2)
<223> OTHER INFORMATION: Asn or Ala
<220> FEATURE:
<221> NAME/KEY: MOD_RES
<222> LOCATION: (3)..(3)
<223> OTHER INFORMATION: Ser or Thr
<220> FEATURE:
<221> NAME/KEY: MOD_RES
<222> LOCATION: (7)..(7)
<223> OTHER INFORMATION: Val, Leu or Ile
<220> FEATURE:
<221> NAME/KEY: MOD_RES
<222> LOCATION: (8)..(8)
<223> OTHER INFORMATION: Asn, Glu, His or Asp

<400> SEQUENCE: 37

Xaa Xaa Xaa Pro Leu Gln Xaa Xaa
1               5

<210> SEQ ID NO 38
<211> LENGTH: 8
<212> TYPE: PRT
<213> ORGANISM: Escherichia coli

<400> SEQUENCE: 38

Ser Asn Ser Pro Leu Gln Val Asp
1               5

<210> SEQ ID NO 39
<211> LENGTH: 7
<212> TYPE: PRT
<213> ORGANISM: Escherichia coli
<220> FEATURE:
<221> NAME/KEY: MOD_RES
<222> LOCATION: (1)..(1)
<223> OTHER INFORMATION: Val, Ile or Met
<220> FEATURE:
<221> NAME/KEY: MOD_RES
<222> LOCATION: (4)..(4)
<223> OTHER INFORMATION: Glu, Lys, Gly, Ile, Gln, Thr or Ser
<220> FEATURE:
<221> NAME/KEY: MOD_RES
<222> LOCATION: (7)..(7)
<223> OTHER INFORMATION: Phe or Tyr

<400> SEQUENCE: 39
```

```
Xaa Tyr Gln Xaa Thr Pro Xaa
1               5

<210> SEQ ID NO 40
<211> LENGTH: 7
<212> TYPE: PRT
<213> ORGANISM: Escherichia coli

<400> SEQUENCE: 40

Val Tyr Gln Ile Thr Pro Tyr
1               5

<210> SEQ ID NO 41
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Thr Ser Arg Val Ser Gly Gln
1               5

<210> SEQ ID NO 42
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Ser Asn Ser Pro Leu Glu Val Asp
1               5

<210> SEQ ID NO 43
<211> LENGTH: 6
<212> TYPE: PRT
<213> ORGANISM: Escherichia coli
<220> FEATURE:
<221> NAME/KEY: MOD_RES
<222> LOCATION: (3)..(3)
<223> OTHER INFORMATION: Ile, Val, Leu or Thr
<220> FEATURE:
<221> NAME/KEY: MOD_RES
<222> LOCATION: (4)..(4)
<223> OTHER INFORMATION: Thr, Lys, Ser or Arg
<220> FEATURE:
<221> NAME/KEY: MOD_RES
<222> LOCATION: (5)..(5)
<223> OTHER INFORMATION: Thr, Ser or Gly
<220> FEATURE:
<221> NAME/KEY: MOD_RES
<222> LOCATION: (6)..(6)
<223> OTHER INFORMATION: Ser, Asn, Thr, Lys, Glu, Arg, Pro, Asn or Ala

<400> SEQUENCE: 43

Gly Glu Xaa Xaa Xaa Xaa
1               5

<210> SEQ ID NO 44
<211> LENGTH: 6
<212> TYPE: PRT
<213> ORGANISM: Escherichia coli

<400> SEQUENCE: 44

Gly Glu Ile Thr Thr Ser
1               5
```

```
<210> SEQ ID NO 45
<211> LENGTH: 10
<212> TYPE: PRT
<213> ORGANISM: Escherichia coli
<220> FEATURE:
<221> NAME/KEY: MOD_RES
<222> LOCATION: (3)..(3)
<223> OTHER INFORMATION: Pro, Gln, Ala or Ser
<220> FEATURE:
<221> NAME/KEY: MOD_RES
<222> LOCATION: (6)..(6)
<223> OTHER INFORMATION: Ala, Asn, Gln, Ser or Phe
<220> FEATURE:
<221> NAME/KEY: MOD_RES
<222> LOCATION: (7)..(7)
<223> OTHER INFORMATION: Val, Gln, Tyr, Arg, Met or Asn
<220> FEATURE:
<221> NAME/KEY: MOD_RES
<222> LOCATION: (10)..(10)
<223> OTHER INFORMATION: Lys, Asp, Asn, Thr, Ser, Ala or Glu

<400> SEQUENCE: 45

Gln Ser Xaa Asp Ile Xaa Xaa Gly Val Xaa
1               5                   10

<210> SEQ ID NO 46
<211> LENGTH: 10
<212> TYPE: PRT
<213> ORGANISM: Escherichia coli

<400> SEQUENCE: 46

Gln Ser Pro Asp Ile Asn Gln Gly Val Asp
1               5                   10

<210> SEQ ID NO 47
<211> LENGTH: 8
<212> TYPE: PRT
<213> ORGANISM: Escherichia coli
<220> FEATURE:
<221> NAME/KEY: MOD_RES
<222> LOCATION: (1)..(1)
<223> OTHER INFORMATION: Gln, Ala, Ile, Val, Glu or Thr
<220> FEATURE:
<221> NAME/KEY: MOD_RES
<222> LOCATION: (8)..(8)
<223> OTHER INFORMATION: Leu, Ile, Ser, Val or Met

<400> SEQUENCE: 47

Xaa Gly Ala Gly Asp Gln Gly Xaa
1               5

<210> SEQ ID NO 48
<211> LENGTH: 8
<212> TYPE: PRT
<213> ORGANISM: Escherichia coli

<400> SEQUENCE: 48

Gln Gly Ala Gly Asp Gln Gly Leu
1               5

<210> SEQ ID NO 49
<211> LENGTH: 8
<212> TYPE: PRT
<213> ORGANISM: Escherichia coli
<220> FEATURE:
<221> NAME/KEY: MOD_RES
<222> LOCATION: (1)..(1)
<223> OTHER INFORMATION: Ser, Pro, Thr or Ala
<220> FEATURE:
```

```
<221> NAME/KEY: MOD_RES
<222> LOCATION: (3)..(3)
<223> OTHER INFORMATION: Ala, Thr, Trp, Tyr, Phe, Ser or Asn
<220> FEATURE:
<221> NAME/KEY: MOD_RES
<222> LOCATION: (4)..(4)
<223> OTHER INFORMATION: Met, Tyr, Leu or Val
<220> FEATURE:
<221> NAME/KEY: MOD_RES
<222> LOCATION: (5)..(5)
<223> OTHER INFORMATION: Ser or Ala
<220> FEATURE:
<221> NAME/KEY: MOD_RES
<222> LOCATION: (7)..(7)
<223> OTHER INFORMATION: Lys, Arg, Glu or Asp
<220> FEATURE:
<221> NAME/KEY: MOD_RES
<222> LOCATION: (8)..(8)
<223> OTHER INFORMATION: Leu or Ile

<400> SEQUENCE: 49

Xaa Ile Xaa Xaa Xaa His Xaa Xaa
1               5

<210> SEQ ID NO 50
<211> LENGTH: 8
<212> TYPE: PRT
<213> ORGANISM: Escherichia coli

<400> SEQUENCE: 50

Pro Ile Thr Tyr Ala His Arg Leu
1               5

<210> SEQ ID NO 51
<211> LENGTH: 5
<212> TYPE: PRT
<213> ORGANISM: Escherichia coli
<220> FEATURE:
<221> NAME/KEY: MOD_RES
<222> LOCATION: (1)..(1)
<223> OTHER INFORMATION: Trp, Phe, Tyr, Val or Glu
<220> FEATURE:
<221> NAME/KEY: MOD_RES
<222> LOCATION: (3)..(3)
<223> OTHER INFORMATION: Arg, Gly, Leu or Lys
<220> FEATURE:
<221> NAME/KEY: MOD_RES
<222> LOCATION: (4)..(4)
<223> OTHER INFORMATION: Pro, Leu, His or Val

<400> SEQUENCE: 51

Xaa Leu Xaa Xaa Asp
1               5

<210> SEQ ID NO 52
<211> LENGTH: 5
<212> TYPE: PRT
<213> ORGANISM: Escherichia coli

<400> SEQUENCE: 52

Trp Leu Arg Pro Asp
1               5

<210> SEQ ID NO 53
<211> LENGTH: 7
<212> TYPE: PRT
<213> ORGANISM: Escherichia coli
<220> FEATURE:
<221> NAME/KEY: MOD_RES
<222> LOCATION: (1)..(1)
<223> OTHER INFORMATION: Val or Ile
```

```
<220> FEATURE:
<221> NAME/KEY: MOD_RES
<222> LOCATION: (2)..(2)
<223> OTHER INFORMATION: Val, Leu or Ile
<220> FEATURE:
<221> NAME/KEY: MOD_RES
<222> LOCATION: (3)..(3)
<223> OTHER INFORMATION: Val, Leu, Ile or Met
<220> FEATURE:
<221> NAME/KEY: MOD_RES
<222> LOCATION: (5)..(5)
<223> OTHER INFORMATION: Thr, Val, Ala, Ser or His

<400> SEQUENCE: 53

Xaa Xaa Xaa Ser Xaa Gln His
1               5

<210> SEQ ID NO 54
<211> LENGTH: 7
<212> TYPE: PRT
<213> ORGANISM: Escherichia coli

<400> SEQUENCE: 54

Val Val Leu Ser Thr Gln His
1               5

<210> SEQ ID NO 55
<211> LENGTH: 7
<212> TYPE: PRT
<213> ORGANISM: Escherichia coli
<220> FEATURE:
<221> NAME/KEY: MOD_RES
<222> LOCATION: (1)..(1)
<223> OTHER INFORMATION: Ile or Val
<220> FEATURE:
<221> NAME/KEY: MOD_RES
<222> LOCATION: (4)..(4)
<223> OTHER INFORMATION: Thr, Gly or Ser
<220> FEATURE:
<221> NAME/KEY: MOD_RES
<222> LOCATION: (6)..(6)
<223> OTHER INFORMATION: Arg, Thr, Gln, Lys or Ser

<400> SEQUENCE: 55

Xaa Asn Pro Xaa Gly Xaa Phe
1               5

<210> SEQ ID NO 56
<211> LENGTH: 7
<212> TYPE: PRT
<213> ORGANISM: Escherichia coli

<400> SEQUENCE: 56

Ile Asn Pro Thr Gly Arg Phe
1               5

<210> SEQ ID NO 57
<211> LENGTH: 7
<212> TYPE: PRT
<213> ORGANISM: Escherichia coli
<220> FEATURE:
<221> NAME/KEY: MOD_RES
<222> LOCATION: (1)..(1)
<223> OTHER INFORMATION: Thr, Val, Ile, Tyr or Glu
<220> FEATURE:
<221> NAME/KEY: MOD_RES
<222> LOCATION: (2)..(2)
<223> OTHER INFORMATION: Val, Ile, Leu or Asn
<220> FEATURE:
<221> NAME/KEY: MOD_RES
<222> LOCATION: (4)..(4)
```

```
<223> OTHER INFORMATION: Gly or Ser
<220> FEATURE:
<221> NAME/KEY: MOD_RES
<222> LOCATION: (6)..(6)
<223> OTHER INFORMATION: Met, Ile, Gln, Ala, His or Asp
<220> FEATURE:
<221> NAME/KEY: MOD_RES
<222> LOCATION: (7)..(7)
<223> OTHER INFORMATION: Gly, Ser, Ala or His

<400> SEQUENCE: 57

Xaa Xaa Gly Xaa Pro Xaa Xaa
1               5

<210> SEQ ID NO 58
<211> LENGTH: 7
<212> TYPE: PRT
<213> ORGANISM: Escherichia coli

<400> SEQUENCE: 58

Val Ile Gly Gly Pro Met Gly
1               5

<210> SEQ ID NO 59
<211> LENGTH: 7
<212> TYPE: PRT
<213> ORGANISM: Escherichia coli
<220> FEATURE:
<221> NAME/KEY: MOD_RES
<222> LOCATION: (1)..(1)
<223> OTHER INFORMATION: Met or Ile
<220> FEATURE:
<221> NAME/KEY: MOD_RES
<222> LOCATION: (2)..(2)
<223> OTHER INFORMATION: Val or Ile

<400> SEQUENCE: 59

Xaa Xaa Asp Thr Tyr Gly Gly
1               5

<210> SEQ ID NO 60
<211> LENGTH: 7
<212> TYPE: PRT
<213> ORGANISM: Escherichia coli

<400> SEQUENCE: 60

Ile Val Asp Thr Tyr Gly Gly
1               5

<210> SEQ ID NO 61
<211> LENGTH: 7
<212> TYPE: PRT
<213> ORGANISM: Escherichia coli
<220> FEATURE:
<221> NAME/KEY: MOD_RES
<222> LOCATION: (6)..(6)
<223> OTHER INFORMATION: Ala or Gly
<220> FEATURE:
<221> NAME/KEY: MOD_RES
<222> LOCATION: (7)..(7)
<223> OTHER INFORMATION: Ala, Ser or Leu

<400> SEQUENCE: 61

Lys Val Asp Arg Ser Xaa Xaa
1               5

<210> SEQ ID NO 62
<211> LENGTH: 7
<212> TYPE: PRT
```

```
<213> ORGANISM: Escherichia coli

<400> SEQUENCE: 62

Lys Val Asp Arg Ser Ala Ala
1               5

<210> SEQ ID NO 63
<211> LENGTH: 11
<212> TYPE: PRT
<213> ORGANISM: Escherichia coli
<220> FEATURE:
<221> NAME/KEY: MOD_RES
<222> LOCATION: (1)..(1)
<223> OTHER INFORMATION: Leu, Glu, Ile, Gln or Thr
<220> FEATURE:
<221> NAME/KEY: MOD_RES
<222> LOCATION: (2)..(2)
<223> OTHER INFORMATION: Val, Ile or Leu
<220> FEATURE:
<221> NAME/KEY: MOD_RES
<222> LOCATION: (4)..(4)
<223> OTHER INFORMATION: Val, Leu or Ile
<220> FEATURE:
<221> NAME/KEY: MOD_RES
<222> LOCATION: (5)..(5)
<223> OTHER INFORMATION: Ala or Ser
<220> FEATURE:
<221> NAME/KEY: MOD_RES
<222> LOCATION: (10)..(10)
<223> OTHER INFORMATION: Val, Ile, Arg, Lys or Ala
<220> FEATURE:
<221> NAME/KEY: MOD_RES
<222> LOCATION: (11)..(11)
<223> OTHER INFORMATION: Ala, Val, Thr or Ser

<400> SEQUENCE: 63

Xaa Xaa Gln Xaa Xaa Tyr Ala Ile Gly Xaa Xaa
1               5                   10

<210> SEQ ID NO 64
<211> LENGTH: 11
<212> TYPE: PRT
<213> ORGANISM: Escherichia coli

<400> SEQUENCE: 64

Glu Ile Gln Val Ser Tyr Ala Ile Gly Val Ala
1               5                   10

<210> SEQ ID NO 65
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Gly Glu Ile Thr Thr Asn
1               5

<210> SEQ ID NO 66
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Gln Ser Pro Asp Ile Asn Gln Ser Val Asp
```

```
1               5                   10
```

<210> SEQ ID NO 67
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Gln Ser Ala Gly Asp Gln Gly Leu
1               5

<210> SEQ ID NO 68
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Pro Ile Thr Tyr Ala Tyr Arg Leu
1               5

<210> SEQ ID NO 69
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Leu Ile Thr Tyr Ala His Arg Leu
1               5

<210> SEQ ID NO 70
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Leu Ile Thr Tyr Ala Tyr Arg Leu
1               5

<210> SEQ ID NO 71
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Trp Leu Cys Pro Asp
1               5

<210> SEQ ID NO 72
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 72

Val Val Leu Ser Thr Gln Tyr
1               5

<210> SEQ ID NO 73
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Val Asp Leu Ser Thr Gln His
1               5

<210> SEQ ID NO 74
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Val Asp Leu Ser Thr Gln Tyr
1               5

<210> SEQ ID NO 75
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Ile Asn Pro Ile Gly Arg Phe
1               5

<210> SEQ ID NO 76
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Val Ile Gly Gly Ser Met Gly
1               5

<210> SEQ ID NO 77
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Ile Val Asp Thr Tyr Gly Asp
1               5

<210> SEQ ID NO 78

```
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Lys Val Asp Arg Phe Ala Ala
1               5

<210> SEQ ID NO 79
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Glu Ile Gln Val Ser Tyr Ala Leu Gly Val Ala
1               5                   10

<210> SEQ ID NO 80
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Ser Asn Ser Pro Phe Gln Val Asp
1               5

<210> SEQ ID NO 81
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Ser Asn Ser Pro Phe Glu Val Asp
1               5

<210> SEQ ID NO 82
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Ser Asn Ser Pro Phe Asp Val Asp Asp
1               5

<210> SEQ ID NO 83
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83
```

Ser Asn Ser Pro Leu Asp Val Asp
1               5

<210> SEQ ID NO 84
<211> LENGTH: 309
<212> TYPE: PRT
<213> ORGANISM: Escherichia coli

<400> SEQUENCE: 84

Met Pro Ile Arg Val Pro Asp Glu Leu Pro Ala Val Asn Phe Leu Arg
1               5                   10                  15

Glu Glu Asn Val Phe Val Met Thr Thr Ser Arg Ala Ser Gly Gln Glu
            20                  25                  30

Ile Arg Pro Leu Lys Val Leu Ile Leu Asn Leu Met Pro Lys Lys Ile
        35                  40                  45

Glu Thr Glu Asn Gln Phe Leu Arg Leu Leu Ser Asn Ser Pro Leu Gln
    50                  55                  60

Val Asp Ile Gln Leu Leu Arg Ile Asp Ser Arg Glu Ser Arg Asn Thr
65                  70                  75                  80

Pro Ala Glu His Leu Asn Asn Phe Tyr Cys Asn Phe Glu Asp Ile Gln
                85                  90                  95

Asp Gln Asn Phe Asp Gly Leu Ile Val Thr Gly Ala Pro Leu Gly Leu
            100                 105                 110

Val Glu Phe Asn Asp Val Ala Tyr Trp Pro Gln Ile Lys Gln Val Leu
        115                 120                 125

Glu Trp Ser Lys Asp His Val Thr Ser Thr Leu Phe Val Cys Trp Ala
    130                 135                 140

Val Gln Ala Ala Leu Asn Ile Leu Tyr Gly Ile Pro Lys Gln Thr Arg
145                 150                 155                 160

Thr Glu Lys Leu Ser Gly Val Tyr Glu His His Ile Leu His Pro His
                165                 170                 175

Ala Leu Leu Thr Arg Gly Phe Asp Asp Ser Phe Leu Ala Pro His Ser
            180                 185                 190

Arg Tyr Ala Asp Phe Pro Ala Ala Leu Ile Arg Asp Tyr Thr Asp Leu
        195                 200                 205

Glu Ile Leu Ala Glu Thr Glu Glu Gly Asp Ala Tyr Leu Phe Ala Ser
    210                 215                 220

Lys Asp Lys Arg Ile Ala Phe Val Thr Gly His Pro Glu Tyr Asp Ala
225                 230                 235                 240

Gln Thr Leu Ala Gln Glu Phe Phe Arg Asp Val Glu Ala Gly Leu Asp
                245                 250                 255

Pro Asp Val Pro Tyr Asn Tyr Phe Pro His Asn Asp Pro Gln Asn Thr
            260                 265                 270

Pro Arg Ala Ser Trp Arg Ser His Gly Asn Leu Leu Phe Thr Asn Trp
        275                 280                 285

Leu Asn Tyr Tyr Val Tyr Gln Ile Thr Pro Tyr Asp Leu Arg His Met
    290                 295                 300

Asn Pro Thr Leu Asp
305

<210> SEQ ID NO 85
<211> LENGTH: 309
<212> TYPE: PRT
<213> ORGANISM: Escherichia coli

<400> SEQUENCE: 85

Met Pro Ile Arg Val Pro Asp Glu Leu Pro Ala Val Asn Phe Leu Arg
1               5                   10                  15

Glu Glu Asn Val Phe Val Met Thr Thr Ser Arg Ala Ser Gly Gln Glu
            20                  25                  30

Ile Arg Pro Leu Lys Val Leu Ile Leu Asn Leu Met Pro Lys Lys Ile
            35                  40                  45

Glu Thr Glu Asn Gln Phe Leu Arg Leu Leu Ser Asn Ser Pro Leu Glu
50                  55                  60

Val Asp Ile Gln Leu Leu Arg Ile Asp Ser Arg Glu Ser Arg Asn Thr
65                  70                  75                  80

Pro Ala Glu His Leu Asn Asn Phe Tyr Cys Asn Phe Glu Asp Ile Gln
                85                  90                  95

Asp Gln Asn Phe Asp Gly Leu Ile Val Thr Gly Ala Pro Leu Gly Leu
            100                 105                 110

Val Glu Phe Asn Asp Val Ala Tyr Trp Pro Gln Ile Lys Gln Val Leu
            115                 120                 125

Glu Trp Ser Lys Asp His Val Thr Ser Thr Leu Phe Val Cys Trp Ala
            130                 135                 140

Val Gln Ala Ala Leu Asn Ile Leu Tyr Gly Ile Pro Lys Gln Thr Arg
145                 150                 155                 160

Thr Glu Lys Leu Ser Gly Val Tyr Glu His His Ile Leu His Pro His
                165                 170                 175

Ala Leu Leu Thr Arg Gly Phe Asp Asp Ser Phe Leu Ala Pro His Ser
            180                 185                 190

Arg Tyr Ala Asp Phe Pro Ala Ala Leu Ile Arg Asp Tyr Thr Asp Leu
            195                 200                 205

Glu Ile Leu Ala Glu Thr Glu Glu Gly Asp Ala Tyr Leu Phe Ala Ser
210                 215                 220

Lys Asp Lys Arg Ile Ala Phe Val Thr Gly His Pro Glu Tyr Asp Ala
225                 230                 235                 240

Gln Thr Leu Ala Gln Glu Phe Phe Arg Asp Val Glu Ala Gly Leu Asp
            245                 250                 255

Pro Asp Val Pro Tyr Asn Tyr Phe Pro His Asn Asp Pro Gln Asn Thr
            260                 265                 270

Pro Arg Ala Ser Trp Arg Ser His Gly Asn Leu Leu Phe Thr Asn Trp
            275                 280                 285

Leu Asn Tyr Tyr Val Tyr Gln Ile Thr Pro Tyr Asp Leu Arg His Met
            290                 295                 300

Asn Pro Thr Leu Asp
305

<210> SEQ ID NO 86
<211> LENGTH: 309
<212> TYPE: PRT
<213> ORGANISM: Escherichia coli

<400> SEQUENCE: 86

Met Pro Ile Arg Val Pro Asp Glu Leu Pro Ala Val Asn Phe Leu Arg
1               5                   10                  15

Glu Glu Asn Val Phe Val Met Thr Thr Ser Arg Ala Ser Gly Gln Glu
            20                  25                  30

Ile Arg Pro Leu Lys Val Leu Ile Leu Asn Leu Met Pro Lys Lys Ile
            35                  40                  45

Glu Thr Glu Asn Gln Phe Leu Arg Leu Leu Ser Asn Ser Pro Phe Gln
50                  55                  60

Val Asp Ile Gln Leu Leu Arg Ile Asp Ser Arg Glu Ser Arg Asn Thr
65                  70                  75                  80

Pro Ala Glu His Leu Asn Asn Phe Tyr Cys Asn Phe Glu Asp Ile Gln
                85                  90                  95

Asp Gln Asn Phe Asp Gly Leu Ile Val Thr Gly Ala Pro Leu Gly Leu
            100                 105                 110

Val Glu Phe Asn Asp Val Ala Tyr Trp Pro Gln Ile Lys Gln Val Leu
        115                 120                 125

Glu Trp Ser Lys Asp His Val Thr Ser Thr Leu Phe Val Cys Trp Ala
130                 135                 140

Val Gln Ala Ala Leu Asn Ile Leu Tyr Gly Ile Pro Lys Gln Thr Arg
145                 150                 155                 160

Thr Glu Lys Leu Ser Gly Val Tyr Glu His His Ile Leu His Pro His
                165                 170                 175

Ala Leu Leu Thr Arg Gly Phe Asp Asp Ser Phe Leu Ala Pro His Ser
            180                 185                 190

Arg Tyr Ala Asp Phe Pro Ala Ala Leu Ile Arg Asp Tyr Thr Asp Leu
        195                 200                 205

Glu Ile Leu Ala Glu Thr Glu Glu Gly Asp Ala Tyr Leu Phe Ala Ser
210                 215                 220

Lys Asp Lys Arg Ile Ala Phe Val Thr Gly His Pro Glu Tyr Asp Ala
225                 230                 235                 240

Gln Thr Leu Ala Gln Glu Phe Phe Arg Asp Val Glu Ala Gly Leu Asp
                245                 250                 255

Pro Asp Val Pro Tyr Asn Tyr Phe Pro His Asn Asp Pro Gln Asn Thr
            260                 265                 270

Pro Arg Ala Ser Trp Arg Ser His Gly Asn Leu Leu Phe Thr Asn Trp
        275                 280                 285

Leu Asn Tyr Tyr Val Tyr Gln Ile Thr Pro Tyr Asp Leu Arg His Met
290                 295                 300

Asn Pro Thr Leu Asp
305

<210> SEQ ID NO 87
<211> LENGTH: 309
<212> TYPE: PRT
<213> ORGANISM: Escherichia coli

<400> SEQUENCE: 87

Met Pro Ile Arg Val Pro Asp Glu Leu Pro Ala Val Asn Phe Leu Arg
1               5                   10                  15

Glu Glu Asn Val Phe Val Met Thr Thr Ser Arg Val Ser Gly Gln Glu
            20                  25                  30

Ile Arg Pro Leu Lys Val Leu Ile Leu Asn Leu Met Pro Lys Lys Ile
        35                  40                  45

Glu Thr Glu Asn Gln Phe Leu Arg Leu Leu Ser Asn Ser Pro Leu Gln
    50                  55                  60

Val Asp Ile Gln Leu Leu Arg Ile Asp Ser Arg Glu Ser Arg Asn Thr
65                  70                  75                  80

Pro Ala Glu His Leu Asn Asn Phe Tyr Cys Asn Phe Glu Asp Ile Gln
                85                  90                  95

Asp Gln Asn Phe Asp Gly Leu Ile Val Thr Gly Ala Pro Leu Gly Leu
            100                 105                 110

Val Glu Phe Asn Asp Val Ala Tyr Trp Pro Gln Ile Lys Gln Val Leu

```
                    115                 120                 125
Glu Trp Ser Lys Asp His Val Thr Ser Thr Leu Phe Val Cys Trp Ala
130                 135                 140

Val Gln Ala Ala Leu Asn Ile Leu Tyr Gly Ile Pro Lys Gln Thr Arg
145                 150                 155                 160

Thr Glu Lys Leu Ser Gly Val Tyr Glu His Ile Leu His Pro His
                165                 170                 175

Ala Leu Leu Thr Arg Gly Phe Asp Asp Ser Phe Leu Ala Pro His Ser
                180                 185                 190

Arg Tyr Ala Asp Phe Pro Ala Ala Leu Ile Arg Asp Tyr Thr Asp Leu
                195                 200                 205

Glu Ile Leu Ala Glu Thr Glu Glu Gly Asp Ala Tyr Leu Phe Ala Ser
210                 215                 220

Lys Asp Lys Arg Ile Ala Phe Val Thr Gly His Pro Glu Tyr Asp Ala
225                 230                 235                 240

Gln Thr Leu Ala Gln Glu Phe Phe Arg Asp Val Glu Ala Gly Leu Asp
                245                 250                 255

Pro Asp Val Pro Tyr Asn Tyr Phe Pro His Asn Asp Pro Gln Asn Thr
                260                 265                 270

Pro Arg Ala Ser Trp Arg Ser His Gly Asn Leu Leu Phe Thr Asn Trp
                275                 280                 285

Leu Asn Tyr Tyr Val Tyr Gln Ile Thr Pro Tyr Asp Leu Arg His Met
                290                 295                 300

Asn Pro Thr Leu Asp
305

<210> SEQ ID NO 88
<211> LENGTH: 309
<212> TYPE: PRT
<213> ORGANISM: Artificial Sequence
<220> FEATURE:
<223> OTHER INFORMATION: Description of Artificial Sequence: Synthetic
      consensus polypeptide

<400> SEQUENCE: 88

Met Pro Ile Arg Val Pro Asp Glu Leu Pro Ala Val Asn Phe Leu Arg
1               5                   10                  15

Glu Glu Asn Val Phe Val Met Thr Thr Ser Arg Ala Ser Gly Gln Glu
                20                  25                  30

Ile Arg Pro Leu Lys Val Leu Ile Leu Asn Leu Met Pro Lys Lys Ile
            35                  40                  45

Glu Thr Glu Asn Gln Phe Leu Arg Leu Leu Ser Asn Ser Pro Leu Gln
50                  55                  60

Val Asp Ile Gln Leu Leu Arg Ile Asp Ser Arg Glu Ser Arg Asn Thr
65                  70                  75                  80

Pro Ala Glu His Leu Asn Asn Phe Tyr Cys Asn Phe Glu Asp Ile Gln
                85                  90                  95

Asp Gln Asn Phe Asp Gly Leu Ile Val Thr Gly Ala Pro Leu Gly Leu
                100                 105                 110

Val Glu Phe Asn Asp Val Ala Tyr Trp Pro Gln Ile Lys Gln Val Leu
                115                 120                 125

Glu Trp Ser Lys Asp His Val Thr Ser Thr Leu Phe Val Cys Trp Ala
130                 135                 140

Val Gln Ala Ala Leu Asn Ile Leu Tyr Gly Ile Pro Lys Gln Thr Arg
145                 150                 155                 160
```

```
Thr Glu Lys Leu Ser Gly Val Tyr Glu His His Ile Leu His Pro His
            165                 170                 175
Ala Leu Leu Thr Arg Gly Phe Asp Asp Ser Phe Leu Ala Pro His Ser
        180                 185                 190
Arg Tyr Ala Asp Phe Pro Ala Ala Leu Ile Arg Asp Tyr Thr Asp Leu
    195                 200                 205
Glu Ile Leu Ala Glu Thr Glu Gly Asp Ala Tyr Leu Phe Ala Ser
    210                 215                 220
Lys Asp Lys Arg Ile Ala Phe Val Thr Gly His Pro Glu Tyr Asp Ala
225                 230                 235                 240
Gln Thr Leu Ala Gln Glu Phe Phe Arg Asp Val Glu Ala Gly Leu Asp
            245                 250                 255
Pro Asp Val Pro Tyr Asn Tyr Phe Pro His Asn Asp Pro Gln Asn Thr
        260                 265                 270
Pro Arg Ala Ser Trp Arg Ser His Gly Asn Leu Leu Phe Thr Asn Trp
    275                 280                 285
Leu Asn Tyr Tyr Val Tyr Gln Ile Thr Pro Tyr Asp Leu Arg His Met
    290                 295                 300
Asn Pro Thr Leu Asp
305

<210> SEQ ID NO 89
<211> LENGTH: 301
<212> TYPE: PRT
<213> ORGANISM: Clostridium acetobutylicum

<400> SEQUENCE: 89

Met Pro Ile Lys Ile Pro Asp Asn Leu Pro Ala Ala Lys Thr Leu Asn
1               5                   10                  15
Glu Glu Asn Ile Phe Phe Met Asp Glu Asp Arg Ala Tyr His Gln Asp
            20                  25                  30
Ile Arg Pro Leu Asn Ile Val Ile Val Asn Leu Met Pro Thr Lys Ile
        35                  40                  45
Val Thr Glu Thr Gln Ile Leu Arg Leu Ile Gly Asn Ser Pro Leu Gln
    50                  55                  60
Val Asn Pro Thr Phe Ile His Thr Gln Thr His Lys Ser Gln Asn Thr
65                  70                  75                  80
Ser Lys Glu His Leu Ile Lys Pro Tyr Glu Thr Phe Glu Glu Ile Lys
            85                  90                  95
Asn Asn Lys Phe Asp Gly Met Ile Val Thr Gly Ala Pro Val Glu Thr
        100                 105                 110
Leu Ser Phe Glu Asn Val Asp Tyr Trp Glu Glu Leu Cys Arg Ile Phe
    115                 120                 125
Asp Trp Ser Val Thr Asn Val Thr Ser Thr Ile His Ile Cys Trp Gly
    130                 135                 140
Ala Gln Ala Gly Leu Tyr His His Tyr Gly Ile Pro Lys Tyr Glu Leu
145                 150                 155                 160
His Glu Lys Leu Phe Gly Val Phe Lys His Asn Leu Thr Glu Arg Asn
            165                 170                 175
Ile Lys Leu Thr Arg Gly Phe Asp Asp Glu Phe Tyr Ala Pro His Ser
        180                 185                 190
Arg His Thr Tyr Val Lys Arg Glu Asp Ile Lys Lys Asn Pro Ser Leu
    195                 200                 205
Lys Ile Leu Ala Glu Ser Asp Glu Ala Gly Ala Tyr Ile Val Ala Ser
    210                 215                 220
```

Glu Asn Gly Lys Asn Ile Phe Val Met Gly His Ala Glu Tyr Asp Gly
225                 230                 235                 240

Asp Thr Leu Asn Leu Glu Tyr Ile Arg Asp Lys Asn Gln Gly Met Asn
            245                 250                 255

Ile Lys Ile Pro Lys Asn Tyr Phe Lys Asp Asn Asp Pro Glu Lys Gly
            260                 265                 270

Pro Met Val Thr Trp Arg Gly His Ala Asn Leu Leu Phe Ser Asn Trp
            275                 280                 285

Leu Asn Tyr Tyr Val Tyr Gln Glu Thr Pro Phe Glu Leu
            290                 295                 300

<210> SEQ ID NO 90
<211> LENGTH: 303
<212> TYPE: PRT
<213> ORGANISM: Bacillus halodurans

<400> SEQUENCE: 90

Met Pro Ile Lys Ile Pro Asp Asn Leu Pro Ala Lys Glu Ile Leu Thr
1               5                   10                  15

Lys Glu Asn Ile Phe Val Met Ala Glu Ser Arg Ala Tyr Ser Gln Asp
            20                  25                  30

Ile Arg Pro Leu Lys Ile Val Ile Leu Asn Leu Met Pro Ile Lys Gln
            35                  40                  45

Thr Thr Glu Thr Gln Leu Leu Arg Leu Leu Gly Asn Thr Pro Leu Gln
    50                  55                  60

Val Glu Val Ser Phe Met Tyr Thr Asp Thr His Ile Ser Lys Asn Thr
65              70                  75                  80

Ser Tyr Asp His Leu Gln Thr Phe Tyr Gln Thr Ile Asp Glu Val Lys
                85                  90                  95

Gln Lys Lys Phe Asp Gly Met Ile Ile Thr Gly Ala Pro Ile Glu Thr
            100                 105                 110

Leu Pro Tyr Asp Glu Val Asp Tyr Trp Asn Glu Leu Lys Gln Ile Met
            115                 120                 125

Glu Trp Ser Lys Thr Asn Val Thr Ser Thr Leu His Ile Cys Trp Gly
130                 135                 140

Ala Gln Ala Gly Leu Phe Tyr His Tyr Gly Val Glu Lys Val Pro Leu
145                 150                 155                 160

Pro Glu Lys Gln Phe Gly Val Tyr Pro His Lys Ile Asn Val Pro Asn
            165                 170                 175

Val Lys Leu Leu Arg Gly Phe Asp Asp Glu Phe Tyr Val Pro His Ser
            180                 185                 190

Arg His Thr Asp Ile Asn Lys Ala Gln Ile Glu Ala His Pro Asp Leu
            195                 200                 205

Glu Ile Leu Ser Glu Ser Glu Gln Ala Gly Val Tyr Ile Val Ala Ser
    210                 215                 220

Lys Asp Gly Lys Gln Ile Phe Val Thr Gly His Ser Glu Tyr Asp Ala
225                 230                 235                 240

Cys Thr Leu Gln Gln Glu Tyr Glu Arg Asp Arg Ala Arg Gly Leu Asn
            245                 250                 255

Ile Gln Val Pro Glu Asn Tyr Phe Pro Asn Asp Asp Ala Thr Arg Lys
            260                 265                 270

Pro Leu Leu Arg Trp Arg Ala His Ser Tyr Leu Leu Phe Ser Asn Trp
            275                 280                 285

Leu Asn Tyr Tyr Val Tyr Gln Glu Thr Pro Tyr Asp Leu Ser Arg

<210> SEQ ID NO 91
<211> LENGTH: 304
<212> TYPE: PRT
<213> ORGANISM: Thermotoga maritima

<400> SEQUENCE: 91

Met Pro Ile Asn Val Pro Ser Gly Leu Pro Ala Val Lys Val Leu Ala
1               5                   10                  15

Lys Glu Gly Ile Phe Val Met Thr Glu Lys Arg Ala Ile His Gln Asp
            20                  25                  30

Ile Arg Pro Leu Glu Ile Leu Leu Asn Leu Met Pro Asp Lys Ile
        35                  40                  45

Lys Thr Glu Ile Gln Leu Leu Arg Leu Leu Gly Asn Thr Pro Leu Gln
    50                  55                  60

Val Asn Val Thr Leu Leu Tyr Thr Glu Thr His Lys Pro Lys His Thr
65                  70                  75                  80

Pro Ile Glu His Ile Leu Lys Phe Tyr Thr Thr Phe Ser Ala Val Lys
                85                  90                  95

Asp Arg Lys Phe Asp Gly Phe Ile Ile Thr Gly Ala Pro Val Glu Leu
            100                 105                 110

Leu Pro Phe Glu Glu Val Asp Tyr Trp Glu Leu Thr Glu Ile Met
        115                 120                 125

Glu Trp Ser Arg His Asn Val Tyr Ser Thr Met Phe Ile Cys Trp Ala
130                 135                 140

Ala Gln Ala Gly Leu Tyr Tyr Phe Tyr Gly Ile Pro Lys Tyr Glu Leu
145                 150                 155                 160

Pro Gln Lys Leu Ser Gly Val Tyr Lys His Arg Val Ala Lys Asp Ser
                165                 170                 175

Val Leu Phe Arg Gly His Asp Asp Phe Phe Trp Ala Pro His Ser Arg
            180                 185                 190

Tyr Thr Glu Val Lys Lys Glu Asp Ile Asp Lys Val Pro Glu Leu Glu
        195                 200                 205

Ile Leu Ala Glu Ser Asp Glu Ala Gly Val Tyr Val Val Ala Asn Lys
    210                 215                 220

Ser Glu Arg Gln Ile Phe Val Thr Gly His Pro Glu Tyr Asp Arg Tyr
225                 230                 235                 240

Thr Leu Arg Asp Glu Tyr Tyr Arg Asp Ile Gly Arg Asn Leu Lys Val
                245                 250                 255

Pro Ile Pro Ala Asn Tyr Phe Pro Asn Asp Asp Pro Thr Lys Thr Pro
            260                 265                 270

Ile Leu Thr Trp Trp Ser His Ala His Leu Phe Phe Ser Asn Trp Leu
        275                 280                 285

Asn Tyr Cys Ile Tyr Gln Lys Thr Pro Tyr Arg Leu Glu Asp Ile His
    290                 295                 300

<210> SEQ ID NO 92
<211> LENGTH: 302
<212> TYPE: PRT
<213> ORGANISM: Bacillus subtilis

<400> SEQUENCE: 92

Met Pro Ile Asn Ile Pro Thr His Leu Pro Ala Lys Gln Val Leu Glu
1               5                   10                  15

Ser Glu His Ile Phe Val Met Asp Glu Ser Arg Ala Phe His Gln Asp

```
            20                  25                  30
Ile Arg Pro Gln Lys Ile Ile Ile Leu Asn Leu Met Pro Lys Lys Ile
        35                  40                  45
Gln Thr Glu Thr Gln Leu Leu Arg Leu Leu Gly Asn Ser Pro Leu Gln
 50                  55                  60
Val His Phe Thr Phe Leu Ile Pro Ser Thr His Thr Pro Lys Asn Thr
 65                  70                  75                  80
Ala Arg Glu His Leu Asp Glu Phe Tyr Thr Thr Phe Ser Asn Ile Arg
                 85                  90                  95
His Lys Arg Phe Asp Gly Met Ile Ile Thr Gly Ala Pro Ile Glu His
                100                 105                 110
Leu Ala Phe Glu Glu Val Ser Tyr Trp Glu Leu Lys Glu Ile Met
            115                 120                 125
Glu Trp Ser Lys Thr Asn Val Thr Ser Thr Leu His Ile Cys Trp Gly
        130                 135                 140
Ala Gln Ala Gly Leu Tyr Tyr His Tyr Gly Val Glu Lys Ile Gln Met
145                 150                 155                 160
Pro Lys Lys Ile Phe Gly Val Phe Glu His Thr Val Leu Ser Lys His
                165                 170                 175
Glu Arg Leu Val Arg Gly Phe Asp Glu Leu Tyr Tyr Val Pro His Ser
                180                 185                 190
Arg His Thr Asp Ile Asn Met Glu Gln Leu Gln Ala Val Pro Glu Leu
            195                 200                 205
Asn Ile Leu Thr Ala Ser Lys Glu Ala Gly Gly Leu Leu Leu Ile Val
        210                 215                 220
Ser Lys Asp Glu Lys Gln Val Phe Leu Thr Gly His Pro Glu Tyr Asp
225                 230                 235                 240
Thr Asn Thr Leu Leu Gln Glu Tyr Glu Arg Asp Leu Glu Arg Asn Leu
                245                 250                 255
Ser Thr Val Glu Ala Pro Lys His Tyr Phe Ala Lys Gly Ser Asn Glu
                260                 265                 270
Pro Val Asn Arg Trp Lys Ala His Ala Thr Leu Leu Phe Met Asn Trp
            275                 280                 285
Leu Asn Tyr Tyr Val Tyr Gln Glu Thr Pro Tyr Glu Trp Asp
        290                 295                 300

<210> SEQ ID NO 93
<211> LENGTH: 314
<212> TYPE: PRT
<213> ORGANISM: Streptococcus pneumoniae

<400> SEQUENCE: 93

Met Pro Ile Arg Ile Asp Lys Lys Leu Pro Ala Val Glu Ile Leu Arg
1               5                   10                  15
Thr Glu Asn Ile Phe Val Met Asp Asp Gln Arg Ala Ala His Gln Asp
            20                  25                  30
Ile Arg Pro Leu Lys Ile Leu Ile Leu Asn Leu Met Pro Gln Lys Met
        35                  40                  45
Val Thr Glu Thr Gln Leu Leu Arg His Leu Ala Asn Thr Pro Leu Gln
 50                  55                  60
Leu Asp Ile Asp Phe Leu Tyr Met Glu Ser His Arg Ser Lys Thr Thr
 65                  70                  75                  80
Arg Ser Glu His Met Glu Thr Phe Tyr Lys Thr Phe Pro Glu Val Lys
                 85                  90                  95
```

```
Asp Glu Tyr Phe Asp Gly Met Ile Ile Thr Gly Ala Pro Val Glu His
            100                 105                 110

Leu Pro Phe Glu Glu Val Asp Tyr Trp Glu Phe Arg Gln Met Leu
        115                 120                 125

Glu Trp Ser Lys Thr His Val Tyr Ser Thr Leu His Ile Cys Trp Gly
130                 135                 140

Ala Gln Ala Gly Leu Tyr Leu Arg Tyr Gly Val Glu Lys Tyr Gln Met
145                 150                 155                 160

Asp Ser Lys Leu Ser Gly Ile Tyr Pro Gln Asp Thr Leu Lys Glu Gly
                165                 170                 175

His Leu Leu Phe Arg Gly Phe Asp Asp Ser Tyr Val Ser Pro His Ser
            180                 185                 190

Arg His Thr Glu Ile Ser Lys Glu Glu Val Leu Asn Lys Thr Asn Leu
        195                 200                 205

Glu Ile Leu Ser Glu Gly Pro Gln Val Gly Val Ser Ile Leu Ala Ser
    210                 215                 220

Arg Asp Leu Arg Glu Ile Tyr Ser Phe Gly His Leu Glu Tyr Asp Arg
225                 230                 235                 240

Asp Thr Leu Ala Lys Glu Tyr Phe Arg Asp Arg Asp Ala Gly Phe Asp
                245                 250                 255

Pro His Ile Pro Glu Asn Tyr Phe Lys Asp Asp Val Asn Gln Val
            260                 265                 270

Pro Cys Leu Cys Trp Ser Ser Ala Ala Leu Phe Phe Ser Asn Trp
        275                 280                 285

Val Asp His Ala Val Tyr Gln Glu Thr Pro Phe Asp Trp Arg Lys Ile
    290                 295                 300

Glu Asp Asp Ala Ser Ala Tyr Gly Tyr Leu
305                 310

<210> SEQ ID NO 94
<211> LENGTH: 321
<212> TYPE: PRT
<213> ORGANISM: Lactococcus lactis

<400> SEQUENCE: 94

Met Pro Val Lys Val Ile Glu Gly Leu Pro Ala Ile Asp Asp Leu Arg
1               5                   10                  15

Ala Asp Asn Ile Phe Val Met Asn Asp Glu Arg Ala Lys Asn Gln Asn
            20                  25                  30

Ile Arg Pro Leu Asn Leu Leu Val Asn Leu Met Pro Arg Lys Leu
        35                  40                  45

Ile Thr Glu Arg Gln Ile Leu Arg Leu Leu Ser Asn Thr Pro Leu Gln
50                  55                  60

Ile Asn Val Glu Phe Leu Tyr Met Thr Ser His Asp Phe Lys Asn Thr
65                  70                  75                  80

Lys Gln Gly His Leu Asp Ser Phe Tyr Lys Ser Phe Ser Glu Ile Lys
                85                  90                  95

Ser Gln Tyr Tyr Asp Gly Leu Ile Val Thr Gly Ala Pro Val Glu Gln
            100                 105                 110

Leu Asn Phe Glu Glu Val Asp Tyr Trp Ser Glu Leu Leu Lys Ile Ile
        115                 120                 125

Asp Trp Ser Lys Ser His Val Tyr Ser Ser Leu His Ile Cys Trp Gly
130                 135                 140

Ala Gln Ala Ala Leu Tyr Ala Arg Tyr Gly Val Thr Lys Glu Asn Leu
145                 150                 155                 160
```

```
Pro Gln Lys Leu Cys Gly Ile Tyr Lys Ser Ser Val Glu Gln Pro Lys
            165                 170                 175

Asn Pro Leu Phe Arg Gly Phe Asp Asp Phe Asn Tyr Pro Gln Ser
        180                 185                 190

Arg Tyr Thr Gln Ser Asn Pro Ser Glu Ile Lys Lys Val Pro Asp Leu
            195                 200                 205

Glu Val Leu Ser Ser Ser Lys Glu Thr Gly Phe Ser Ile Leu Ala Lys
210                 215                 220

Lys Asn Leu Arg Glu Ile Tyr Leu Phe Gly His Leu Glu Tyr Asp Arg
225                 230                 235                 240

Glu Thr Leu Ala Trp Glu Tyr Glu Arg Asp Lys Glu Glu Gly Leu Lys
                245                 250                 255

Pro Asn Leu Pro Gln Asn Tyr Phe Pro Glu Asn Asp Asp Lys Asn Lys
            260                 265                 270

Pro Lys Ser Thr Trp Ala Ser Ala Ala Ser Leu Phe Phe Ser Asn Trp
        275                 280                 285

Leu Asn Tyr Ala Val Tyr Gln Gly Thr Pro Tyr Leu Gly Glu Arg Leu
    290                 295                 300

Ser Gln His Leu Asn Glu Glu Asn Tyr Asp Phe Asn Gln Lys Glu Gln
305                 310                 315                 320

Lys

<210> SEQ ID NO 95
<211> LENGTH: 309
<212> TYPE: PRT
<213> ORGANISM: Salmonella typhimurium

<400> SEQUENCE: 95

Met Pro Ile Arg Val Leu Asp Glu Leu Pro Ala Val Asn Phe Leu Arg
1               5                   10                  15

Glu Glu Asn Val Phe Val Met Thr Thr Ser Arg Ala Ser Gly Gln Glu
            20                  25                  30

Ile Arg Pro Leu Lys Val Leu Ile Leu Asn Leu Met Pro Lys Lys Ile
        35                  40                  45

Glu Thr Glu Asn Gln Phe Leu Arg Leu Leu Ser Asn Ser Pro Leu Gln
    50                  55                  60

Val Asp Ile Gln Leu Leu Arg Ile Asp Ala Arg Glu Ser Arg Asn Thr
65                  70                  75                  80

Pro Ala Glu His Leu Asn Asn Phe Tyr Cys Asn Phe Asp Asp Ile Cys
                85                  90                  95

Asp Gln Asn Phe Asp Gly Leu Ile Val Thr Gly Ala Pro Leu Gly Leu
            100                 105                 110

Val Glu Phe Asn Asp Val Ala Tyr Trp Pro Gln Ile Arg Gln Val Leu
        115                 120                 125

Glu Trp Ala Lys Asp His Val Thr Ser Thr Leu Phe Val Cys Trp Ala
    130                 135                 140

Val Gln Ala Ala Leu Asn Ile Leu Tyr Gly Ile Pro Lys Gln Thr Arg
145                 150                 155                 160

Thr Asp Lys Leu Ser Gly Val Tyr Glu His His Ile Leu His Pro His
                165                 170                 175

Ala Leu Leu Thr Arg Gly Phe Asp Asp Ser Phe Leu Ala Pro His Ser
            180                 185                 190

Arg Tyr Ala Asp Phe Pro Ala Ala Leu Ile Arg Asp Tyr Thr Asp Leu
        195                 200                 205
```

```
Glu Ile Leu Ala Glu Thr Glu Gly Asp Ala Tyr Leu Phe Ala Ser
    210                 215                 220

Lys Asp Lys Arg Ile Ala Phe Val Thr Gly His Pro Glu Tyr Asp Ala
225                 230                 235                 240

His Thr Leu Ala Gly Glu Tyr Phe Arg Asp Val Glu Ala Gly Leu Asn
                245                 250                 255

Pro Glu Val Pro Tyr Asn Tyr Phe Pro Lys Asn Asp Pro Gln Asn Ile
                260                 265                 270

Pro Arg Ala Thr Trp Arg Ser His Gly Asn Leu Leu Phe Thr Asn Trp
                275                 280                 285

Leu Asn Tyr Tyr Val Tyr Gln Ile Thr Pro Tyr Asp Leu Arg His Met
    290                 295                 300

Asn Pro Thr Leu Asp
305

<210> SEQ ID NO 96
<211> LENGTH: 309
<212> TYPE: PRT
<213> ORGANISM: Salmonella typhi

<400> SEQUENCE: 96

Met Pro Ile Arg Val Leu Asp Glu Leu Pro Ala Val Asn Phe Leu Arg
1               5                   10                  15

Glu Glu Asn Val Phe Val Met Thr Thr Ser Arg Ala Ser Gly Gln Glu
                20                  25                  30

Ile Arg Pro Leu Lys Val Leu Ile Leu Asn Leu Met Pro Lys Lys Ile
            35                  40                  45

Glu Thr Glu Asn Gln Phe Leu Arg Leu Ser Asn Ser Pro Leu Gln
    50                  55                  60

Val Asp Ile Gln Leu Leu Arg Ile Asp Ala Arg Glu Ser Arg Asn Thr
65                  70                  75                  80

Pro Ala Glu His Leu Asn Asn Phe Tyr Cys Asn Phe Asp Asp Ile Cys
                85                  90                  95

Asp Gln Asn Phe Asp Gly Leu Ile Val Thr Gly Ala Pro Leu Gly Leu
                100                 105                 110

Val Glu Phe Asn Asp Val Ala Tyr Trp Pro Gln Ile Arg Gln Val Leu
            115                 120                 125

Glu Trp Ala Lys Asp His Val Thr Ser Thr Leu Phe Val Cys Trp Ala
    130                 135                 140

Val Gln Ala Ala Leu Asn Ile Leu Tyr Gly Ile Pro Lys Gln Thr Arg
145                 150                 155                 160

Thr Asp Lys Leu Ser Gly Val Tyr Glu His His Ile Leu His Pro His
                165                 170                 175

Ala Leu Leu Thr Arg Gly Phe Asp Asp Ser Phe Leu Ala Pro His Ser
                180                 185                 190

Arg Tyr Ala Asp Phe Pro Ala Ala Leu Ile Arg Asp Tyr Thr Asp Leu
            195                 200                 205

Glu Ile Leu Ala Glu Thr Glu Gly Asp Ala Tyr Leu Phe Ala Ser
    210                 215                 220

Lys Asp Lys Arg Ile Ala Phe Val Thr Gly His Pro Glu Tyr Asp Ala
225                 230                 235                 240

His Thr Leu Ala Gly Glu Tyr Phe Arg Asp Val Glu Ala Gly Leu Asn
                245                 250                 255

Pro Glu Ile Pro Tyr Asn Tyr Phe Pro Lys Asn Asp Pro Gln Ser Ile
```

```
                    260                 265                 270
Pro Arg Thr Thr Trp Arg Ser His Gly Asn Leu Leu Phe Thr Asn Trp
            275                 280                 285

Leu Asn Tyr Tyr Val Tyr Gln Ile Thr Pro Tyr Asp Leu Arg His Met
            290                 295                 300

Asn Pro Thr Leu Asp
305

<210> SEQ ID NO 97
<211> LENGTH: 309
<212> TYPE: PRT
<213> ORGANISM: Escherichia coli

<400> SEQUENCE: 97

Met Pro Ile Arg Val Pro Asp Glu Leu Pro Ala Val Asn Phe Leu Arg
1               5                   10                  15

Glu Glu Asn Val Phe Val Met Thr Thr Ser Arg Ala Ser Gly Gln Glu
            20                  25                  30

Ile Arg Pro Leu Lys Val Leu Ile Leu Asn Leu Met Pro Lys Lys Ile
            35                  40                  45

Glu Thr Glu Asn Gln Phe Leu Arg Leu Leu Ser Asn Ser Pro Leu Gln
        50                  55                  60

Val Asp Ile Gln Leu Leu Arg Ile Asp Ser Arg Glu Ser Arg Asn Thr
65                  70                  75                  80

Pro Ala Glu His Leu Asn Asn Phe Tyr Cys Asn Phe Glu Asp Ile Gln
            85                  90                  95

Glu Gln Asn Phe Asp Gly Leu Ile Val Thr Gly Ala Pro Leu Gly Leu
            100                 105                 110

Val Glu Phe Asn Asp Val Ala Tyr Trp Pro Gln Ile Lys Gln Val Leu
            115                 120                 125

Glu Trp Ser Lys Asp His Val Thr Ser Thr Leu Phe Val Cys Trp Ala
        130                 135                 140

Val Gln Ala Ala Leu Asn Ile Leu Tyr Gly Ile Pro Lys Gln Thr Arg
145                 150                 155                 160

Thr Asp Lys Leu Ser Gly Val Tyr Glu His His Ile Leu His Pro His
            165                 170                 175

Ala Leu Leu Thr Arg Gly Phe Asp Asp Ser Phe Leu Ala Pro His Ser
            180                 185                 190

Arg Tyr Ala Asp Phe Pro Ala Ala Leu Ile Arg Asp Tyr Thr Asp Leu
            195                 200                 205

Glu Ile Leu Ala Glu Thr Glu Glu Gly Asp Ala Tyr Leu Phe Ala Ser
        210                 215                 220

Lys Asp Lys Arg Ile Ala Phe Val Thr Gly His Pro Glu Tyr Asp Ala
225                 230                 235                 240

Gln Thr Leu Ala Gln Glu Tyr Phe Arg Asp Val Glu Ala Gly Leu Asp
            245                 250                 255

Pro Glu Val Pro Tyr Asn Tyr Phe Pro His Asn Asp Pro Gln Asn Lys
            260                 265                 270

Pro Arg Ala Ser Trp Arg Ser His Gly Asn Leu Leu Phe Thr Asn Trp
            275                 280                 285

Leu Asn Tyr Tyr Val Tyr Gln Ile Thr Pro Tyr Asp Leu Arg His Met
            290                 295                 300

Asn Pro Thr Leu Asp
305
```

<210> SEQ ID NO 98
<211> LENGTH: 309
<212> TYPE: PRT
<213> ORGANISM: Escherichia coli

<400> SEQUENCE: 98

```
Met Pro Ile Arg Val Pro Asp Glu Leu Pro Ala Val Asn Phe Leu Arg
1               5                   10                  15

Glu Glu Asn Val Phe Val Met Thr Thr Ser Arg Ala Ser Gly Gln Glu
            20                  25                  30

Ile Arg Pro Leu Lys Val Leu Ile Leu Asn Leu Met Pro Lys Lys Ile
        35                  40                  45

Glu Thr Glu Asn Gln Phe Leu Arg Leu Leu Ser Asn Ser Pro Leu Gln
    50                  55                  60

Val Asp Ile Gln Leu Leu Arg Ile Asp Ser Arg Glu Ser Arg Asn Thr
65                  70                  75                  80

Pro Ala Glu His Leu Asn Asn Phe Tyr Cys Asn Phe Glu Asp Ile Gln
                85                  90                  95

Asp Gln Asn Phe Asp Gly Leu Ile Val Thr Gly Ala Pro Leu Gly Leu
            100                 105                 110

Val Glu Phe Asn Asp Val Ala Tyr Trp Pro Gln Ile Lys Gln Val Leu
        115                 120                 125

Glu Trp Ser Lys Asp His Val Thr Ser Thr Leu Phe Val Cys Trp Ala
    130                 135                 140

Val Gln Ala Ala Leu Asn Ile Leu Tyr Gly Ile Pro Lys Gln Thr Arg
145                 150                 155                 160

Thr Glu Lys Leu Ser Gly Val Tyr Glu His His Ile Leu His Pro His
                165                 170                 175

Ala Leu Leu Thr Arg Gly Phe Asp Asp Ser Phe Leu Ala Pro His Ser
            180                 185                 190

Arg Tyr Ala Asp Phe Pro Ala Ala Leu Ile Arg Asp Tyr Thr Asp Leu
        195                 200                 205

Glu Ile Leu Ala Glu Thr Glu Glu Gly Asp Ala Tyr Leu Phe Ala Ser
    210                 215                 220

Lys Asp Lys Arg Ile Ala Phe Val Thr Gly His Pro Glu Tyr Asp Ala
225                 230                 235                 240

Gln Thr Leu Ala Gln Glu Phe Phe Arg Asp Val Glu Ala Gly Leu Asp
                245                 250                 255

Pro Asp Val Pro Tyr Asn Tyr Phe Pro His Asn Asp Pro Gln Asn Thr
            260                 265                 270

Pro Arg Ala Ser Trp Arg Ser His Gly Asn Leu Leu Phe Thr Asn Trp
        275                 280                 285

Leu Asn Tyr Tyr Val Tyr Gln Ile Thr Pro Tyr Asp Leu Arg His Met
    290                 295                 300

Asn Pro Thr Leu Asp
305
```

<210> SEQ ID NO 99
<211> LENGTH: 309
<212> TYPE: PRT
<213> ORGANISM: Yersinia pestis

<400> SEQUENCE: 99

```
Met Pro Ile Arg Val Pro Asp Glu Leu Pro Ala Val Ser Phe Leu Arg
1               5                   10                  15
```

Asn Glu Asn Val Phe Val Met Ala Ser Ser Arg Ala Lys Thr Gln Glu
            20                  25                  30

Ile Arg Pro Leu Lys Val Leu Ile Leu Asn Leu Met Pro Lys Lys Ile
        35                  40                  45

Glu Thr Glu Asn Gln Phe Leu Arg Leu Leu Ser Asn Ser Pro Leu Gln
 50                  55                  60

Val Asp Ile Gln Leu Leu Arg Val Asp Ser Arg Glu Ser Lys Asn Thr
65                  70                  75                  80

Pro Thr Glu His Leu Asn Asn Phe Tyr Cys Asp Phe Glu Asp Ile Gln
                85                  90                  95

Asp Gln Asn Phe Asp Gly Leu Ile Val Thr Gly Ala Pro Leu Gly Leu
            100                 105                 110

Val Asp Phe Cys Asp Val Ala Tyr Trp Pro Gln Ile Glu Arg Ile Ile
        115                 120                 125

Ala Trp Ala Lys Glu His Val Thr Ser Thr Leu Phe Val Cys Trp Ala
130                 135                 140

Val Gln Ala Ala Leu Asn Ile Leu Tyr Gly Ile Pro Lys Met Thr Arg
145                 150                 155                 160

Glu Val Lys Leu Ser Gly Ile Tyr Gln His Gln Thr Leu Glu Pro Leu
                165                 170                 175

Ala Leu Leu Thr Arg Gly Phe Asp Glu Thr Phe Leu Ala Pro His Ser
            180                 185                 190

Arg Tyr Ala Asp Phe Pro Val Glu Val Leu Gln Gln Tyr Thr Asp Leu
        195                 200                 205

Asp Ile Leu Val Ser Ser Glu Glu Ala Gly Ala Tyr Leu Phe Ala Ser
210                 215                 220

Lys Asp Lys Arg Val Ala Phe Val Thr Gly His Pro Glu Tyr Asp Val
225                 230                 235                 240

Asp Thr Leu Ala Gly Glu Tyr Gln Arg Asp Leu Ala Ala Gly Leu Asn
                245                 250                 255

Pro Gln Val Pro Leu Asn Tyr Phe Pro Ser Asp Ala Ser Leu Arg
            260                 265                 270

Pro Lys Ala Ser Trp Arg Ser His Gly His Leu Leu Phe Ala Asn Trp
        275                 280                 285

Leu Asn Tyr Tyr Val Tyr Gln Ile Thr Pro Phe Asp Leu Arg His Met
290                 295                 300

Asn Pro Thr Leu Asp
305

<210> SEQ ID NO 100
<211> LENGTH: 313
<212> TYPE: PRT
<213> ORGANISM: Vibrio cholerae

<400> SEQUENCE: 100

Met Pro Ile Arg Ile Pro Asp Gln Leu Pro Ala Ser Asp Val Leu Arg
1               5                   10                  15

Asn Glu Asn Ile Phe Val Met Ser Glu Ser Arg Ala Ser Thr Gln Glu
            20                  25                  30

Ile Arg Pro Leu Lys Val Leu Leu Asn Leu Met Pro Lys Lys Ile
        35                  40                  45

Glu Thr Glu Thr Gln Phe Leu Arg Leu Leu Ser Asn Ser Pro Leu Gln
 50                  55                  60

Val Asp Ile Glu Leu Leu Arg Ile Asp Asp Arg Pro Ser Lys Asn Thr
65                  70                  75                  80

Pro Glu Glu His Leu Asn Thr Phe Tyr Arg Gln Phe Glu Leu Val Lys
                85                  90                  95

Asn Arg Asn Phe Asp Gly Leu Ile Ile Thr Gly Ala Pro Leu Gly Leu
                100                 105                 110

Val Gln Phe Glu Asp Val Ala Tyr Trp Gln His Leu Gln Asn Ile Met
                115                 120                 125

Ala Trp Ala Lys Ala His Val Thr Ser Thr Leu Tyr Ile Cys Trp Ala
130                 135                 140

Ala Gln Ala Gly Leu Lys Leu Leu Tyr Asn Leu Pro Lys Arg Thr Arg
145                 150                 155                 160

Glu Glu Lys Leu Ser Gly Val Tyr Tyr His Asp Ile His Lys Pro Phe
                165                 170                 175

His Pro Leu Leu Arg Gly Phe Asp Asp Arg Phe Leu Ala Pro His Ser
                180                 185                 190

Arg Tyr Ala Asp Phe Asp Ala Glu Phe Leu Ala Glu His Thr Asp Leu
                195                 200                 205

Asp Ile Leu Ala Thr Ser Asp Val Ala Gly Val Tyr Leu Ala Ala Thr
                210                 215                 220

Lys Asp Lys Arg Asn Val Phe Val Thr Gly His Pro Glu Tyr Asp Ala
225                 230                 235                 240

Tyr Thr Leu His Gly Glu Tyr Val Arg Asp Leu Gly Glu Gly Leu Asn
                245                 250                 255

Pro Ala Ile Pro Val Asn Tyr Tyr Pro Asn Asp Asn Pro Asp Asn Lys
                260                 265                 270

Pro Cys Ala Ser Trp Arg Ser His Gly His Leu Leu Phe Ala Asn Trp
                275                 280                 285

Leu Asn Tyr Cys Val Tyr Gln Gln Thr Pro Tyr Asp Leu Glu Lys Phe
                290                 295                 300

Ser Glu Ala Asn Phe Thr Lys Asp Glu
305                 310

<210> SEQ ID NO 101
<211> LENGTH: 313
<212> TYPE: PRT
<213> ORGANISM: Vibrio vulnificus

<400> SEQUENCE: 101

Met Pro Ile Arg Ile Pro Asp Gln Leu Pro Ala Ala Asp Val Leu Arg
1               5                   10                  15

Thr Glu Asn Ile Phe Val Met Ser Glu Thr Arg Ala Ala Ser Gln Glu
                20                  25                  30

Ile Arg Pro Leu Arg Val Leu Ile Leu Asn Leu Met Pro Lys Lys Ile
                35                  40                  45

Glu Thr Glu Thr Gln Phe Leu Arg Leu Leu Ser Asn Ser Pro Leu Gln
        50                  55                  60

Val Asn Val Glu Leu Leu Arg Ile Asp Asp Arg Pro Ser Lys Asn Thr
65                  70                  75                  80

Pro Thr Glu His Leu Asp Asn Phe Tyr Arg Gln Phe Glu Met Val Lys
                85                  90                  95

Asn Arg Asn Phe Asp Gly Leu Ile Ile Thr Gly Ala Pro Leu Gly Leu
                100                 105                 110

Val Gln Phe Glu Asp Val Ile Tyr Trp Asp His Leu Lys Thr Ile Met
                115                 120                 125

Glu Trp Ala Lys Ser His Val Thr Ser Thr Leu Tyr Val Cys Trp Ala

```
                130                 135                 140
Ala Gln Ala Gly Leu Lys Leu Leu Tyr Asp Leu Pro Lys Lys Thr Arg
145                 150                 155                 160

Lys Glu Lys Leu Ser Gly Val Tyr His His Arg Ile His Lys Pro Tyr
                165                 170                 175

His Pro Val Leu Arg Gly Phe Asp Asp Ser Phe Leu Ala Pro His Ser
            180                 185                 190

Arg Tyr Ala Asp Phe Ser Pro Glu Tyr Leu Ala Glu His Thr Asp Leu
        195                 200                 205

Asp Ile Leu Ala Thr Ser Asp Asp Ala Gly Val Tyr Leu Ala Thr Thr
    210                 215                 220

Lys Asp Lys Arg Asn Val Phe Val Thr Gly His Pro Glu Tyr Asp Pro
225                 230                 235                 240

His Thr Leu His Asn Glu Tyr Ile Arg Asp Leu Gly Glu Gly Met Glu
                245                 250                 255

Pro Ala Ile Pro Val Asn Tyr Tyr Pro Asn Asp Asn Pro Asp Asn Pro
            260                 265                 270

Pro Ile Ala Ser Trp Arg Ser His Gly His Leu Leu Phe Ser Asn Trp
        275                 280                 285

Leu Asn Tyr Cys Val Tyr Gln Gln Thr Pro Tyr Asp Leu Asp His Phe
    290                 295                 300

Ser Glu Glu Ala Phe Thr Lys Asp Glu
305                 310

<210> SEQ ID NO 102
<211> LENGTH: 313
<212> TYPE: PRT
<213> ORGANISM: Vibrio parahaemolyticus

<400> SEQUENCE: 102

Met Pro Ile Arg Ile Pro Asp Gln Leu Pro Ala Ser Asp Val Leu Arg
1               5                   10                  15

Thr Glu Asn Ile Phe Val Met Ser Glu Thr Arg Ala Ala Ser Gln Glu
                20                  25                  30

Ile Arg Pro Leu Arg Val Leu Ile Leu Asn Leu Met Pro Lys Lys Ile
            35                  40                  45

Glu Thr Glu Thr Gln Phe Leu Arg Leu Leu Ser Asn Ser Pro Leu Gln
        50                  55                  60

Val Asn Val Glu Leu Leu Arg Ile Asp Asn Arg Pro Ser Lys Asn Thr
65                  70                  75                  80

Pro Thr Glu His Leu Asp Thr Phe Tyr Arg Gln Phe Glu Met Val Lys
                85                  90                  95

Gly Lys Asn Phe Asp Gly Leu Ile Ile Thr Gly Ala Pro Leu Gly Leu
            100                 105                 110

Val Gln Phe Glu Asp Val Ile Tyr Trp Asp His Leu Lys Thr Ile Met
        115                 120                 125

Glu Trp Ala Lys Asp His Val Thr Ser Thr Leu Tyr Val Cys Trp Ala
    130                 135                 140

Ala Gln Ala Gly Leu Lys Leu Leu Tyr Asp Leu Pro Lys Lys Thr Arg
145                 150                 155                 160

Lys Glu Lys Leu Ser Gly Val Tyr His His Gln Ile His Asn Pro Phe
                165                 170                 175

His Pro Ile Leu Arg Gly Phe Asp Asp Thr Phe Leu Ala Pro His Ser
            180                 185                 190
```

```
Arg Tyr Ala Asp Phe Ser Pro His Phe Leu Glu Glu His Thr Asp Leu
            195                 200                 205

Asp Ile Leu Ala Thr Ser Asp Val Ala Gly Val Tyr Leu Ala Thr Thr
210                 215                 220

Lys Asp Lys Arg Asn Val Phe Val Thr Gly His Pro Glu Tyr Asp Ser
225                 230                 235                 240

His Thr Leu His Asn Glu Tyr Ile Arg Asp Leu Gly Glu Gly Met Glu
                245                 250                 255

Pro Ala Ile Pro Val Asn Tyr Tyr Pro Asn Asn Pro Asp Asn Pro
            260                 265                 270

Pro Ile Ala Ser Trp Arg Ser His Gly His Leu Leu Phe Leu Asn Trp
            275                 280                 285

Leu Asn Tyr Cys Val Tyr Gln Gln Thr Pro Tyr Asp Leu Asp His Phe
290                 295                 300

Ser Glu Asp Ala Phe Thr Lys Asp Asp
305                 310

<210> SEQ ID NO 103
<211> LENGTH: 308
<212> TYPE: PRT
<213> ORGANISM: Sinorhizobium meliloti

<400> SEQUENCE: 103

Met Pro Ile Lys Ile Pro Asp Thr Leu Pro Ala Phe Glu Thr Leu Val
1               5                   10                  15

His Glu Gly Val Arg Leu Met Thr Glu Thr Glu Ala Ile Arg Gln Asp
            20                  25                  30

Ile Arg Pro Leu Gln Ile Gly Leu Leu Asn Leu Met Pro Asn Lys Ile
        35                  40                  45

Lys Thr Glu Ile Gln Met Ala Arg Leu Ile Gly Ala Thr Pro Leu Gln
50                  55                  60

Val Glu Leu Thr Leu Val Arg Val Asn Gly His Arg Pro Lys Asn Thr
65                  70                  75                  80

Pro Glu Glu His Leu Leu Ala Phe Tyr Glu Thr Phe Glu Glu Val Glu
                85                  90                  95

Ala Arg Lys Phe Asp Gly Phe Ile Ile Thr Gly Ala Pro Ile Glu Thr
            100                 105                 110

Leu Glu Tyr Glu Glu Val Thr Tyr Trp Lys Glu Leu Gln Arg Ile Phe
        115                 120                 125

Asp Trp Thr Thr Thr Asn Val His Ser Thr Leu Asn Val Cys Trp Gly
130                 135                 140

Gly Met Ala Ala Val Tyr His Phe His Gly Val Pro Lys Tyr Pro Leu
145                 150                 155                 160

Lys Glu Lys Ala Phe Gly Val Tyr Arg His Gln Asn Leu Gln Pro Ser
                165                 170                 175

Ser Val Tyr Leu Asn Gly Phe Ser Asp Asp Phe Ala Val Pro Val Ser
            180                 185                 190

Arg Trp Thr Glu Val Arg Arg Ala Asp Ile Asp Arg Val Pro Asp Leu
        195                 200                 205

Glu Ile Leu Met Glu Ser Lys Glu Val Gly Val Cys Leu Val His Glu
210                 215                 220

Lys Lys Gly Asn Arg Leu Tyr Met Phe Asn His Val Glu Tyr Asp Ser
225                 230                 235                 240

Thr Ser Leu Ser Glu Glu Tyr Phe Arg Asp Val Asp Ala Gly Val Pro
                245                 250                 255
```

```
Ile Lys Leu Pro His Asp Tyr Phe Pro His Asn Asp Ser Ala Leu Pro
            260                 265                 270

Pro Gln Asn Arg Trp Arg Ser His Ala His Leu Phe Phe Gly Asn Trp
            275                 280                 285

Ile Asn Glu Ile Tyr Gln Thr Thr Pro Tyr Glu Leu Ala Lys Ile Gly
            290                 295                 300

Thr Gly Glu Arg
305

<210> SEQ ID NO 104
<211> LENGTH: 306
<212> TYPE: PRT
<213> ORGANISM: Brucella melitensis

<400> SEQUENCE: 104

Met Pro Ile Lys Ile Pro Asp Asp Leu Pro Ala Thr Ser Val Leu Glu
1               5                   10                  15

Ala Glu Gly Val Met Val Met Arg Glu Ala Asp Ala Val Arg Gln Asp
            20                  25                  30

Ile Arg Pro Leu Arg Ile Gly Leu Leu Asn Leu Met Pro Asn Lys Val
            35                  40                  45

Thr Thr Glu Thr Gln Ile Ala Arg Leu Leu Gly Ala Thr Pro Leu Gln
50                  55                  60

Val Glu Leu Thr Leu Val Arg Met Thr Asn His Val Ala Arg His Thr
65                  70                  75                  80

Pro Ala Asp His Met Leu Ser Phe Tyr Cys Pro Trp Glu Glu Val Asn
                85                  90                  95

Asp Gln Arg Phe Asp Gly Phe Val Ile Thr Gly Ala Pro Val Glu Arg
            100                 105                 110

Leu Pro Phe Glu Glu Val Thr Tyr Trp Asp Glu Met Arg Arg Val Phe
            115                 120                 125

Asp Trp Thr Gln Ser His Val His Arg Thr Leu Asn Ile Cys Trp Ala
        130                 135                 140

Ala Gln Ala Ala Val Tyr His Phe His Gly Met Lys Lys Tyr Asp Leu
145                 150                 155                 160

Pro Ala Lys Ala Ser Gly Val Phe Arg Gln Arg Ser Leu Val Leu Ala
                165                 170                 175

Ser Pro Tyr Leu Arg Gly Phe Ser Asp Asp Phe Ala Ile Pro Val Ser
            180                 185                 190

Arg Trp Thr Glu Val Arg Lys Ser Asp Ile Pro Ala Asp Ser Gly Leu
            195                 200                 205

Lys Val Leu Val Asp Ser Thr Glu Thr Gly Leu Cys Leu Leu Asp Asp
210                 215                 220

Pro Arg His Arg Ser Leu His Met Phe Asn His Val Glu Tyr Asp Thr
225                 230                 235                 240

Thr Ser Leu Ala Asp Glu Tyr Phe Arg Asp Ile Gln Val Gln Pro Glu
                245                 250                 255

Ala Lys Val Pro Val Asn Tyr Phe Pro Gly Asp Asp Ala Lys Arg Pro
            260                 265                 270

Pro Glu Asn Arg Trp Arg Ser His Ala His Leu Leu Phe Gly Asn Trp
            275                 280                 285

Ile Asn Glu Met Tyr Gln Ser Thr Pro Tyr Asp Ile Glu Arg Ile Gly
            290                 295                 300

Lys Val
```

<210> SEQ ID NO 105
<211> LENGTH: 306
<212> TYPE: PRT
<213> ORGANISM: Brucella melitensis

<400> SEQUENCE: 105

Met Pro

```
  1               5                  10                 15
Glu His Ala Phe Ile Met Gly Leu Arg Arg Ala Lys His Gln Asp Ile
              20                 25                 30

Arg Pro Gln Glu Ile Leu Ile Val Asn Leu Met Pro Lys Lys Ile Glu
              35                 40                 45

Thr Glu Asn Gln Ile Leu Ser Leu Leu Ala Asn Ser Pro Leu Gln Val
 50                  55                 60

Asn Ile Thr Leu Leu Ala Thr Thr Ser Tyr Val Gly Lys Asn Thr Pro
 65                  70                 75                 80

Phe Thr His Leu Glu Lys Phe Tyr Lys Gly Leu Glu Glu Val Lys Lys
              85                 90                 95

His Lys Phe Asp Gly Ala Ile Val Thr Gly Ala Pro Val Glu Gln Met
             100                105                110

Asp Phe Glu Lys Val Ala Tyr Trp Glu Glu Leu Glu Ile Phe Asp
             115                120                125

Phe Leu Lys Gln Asn Val Thr Ser Ser Met Tyr Ile Cys Trp Gly Ala
130                  135                140

Met Ala Ala Leu Lys Tyr Phe Tyr Gly Val Asp Lys Ile Ser Leu Asp
145                  150                155                160

Lys Lys Ile Phe Gly Val Tyr Lys His Asp Lys Val Ser Pro Asp Leu
             165                170                175

Leu Leu Thr Asn Leu Asp Glu Lys Val Leu Met Pro His Ser Arg His
             180                185                190

Ser Ser Met Asp Glu Glu Gln Ile Leu Ala Leu Gln Lys Gln Gly Lys
             195                200                205

Leu Lys Ile Leu Leu Arg Asn Lys Lys Ile Gly Ser Ala Leu Leu Arg
210                  215                220

Asp Glu Lys Asn Ile Phe Ile Leu Gly His Leu Glu Tyr Phe Lys Glu
225                  230                235                240

Thr Leu His Gln Glu Tyr Val Arg Asp Asn Phe Ile Gln Lys Ala Lys
             245                250                255

Asn Tyr Tyr Asp Lys Lys Gly Asn Ile Lys Tyr Asn Trp Arg Ser Asn
             260                265                270

Ala Asn Thr Ile Phe Ala Asn Trp Leu Asn Tyr Asp Val Tyr Gln Ser
             275                280                285

Thr Pro Phe Val Leu
             290

<210> SEQ ID NO 107
<211> LENGTH: 387
<212> TYPE: PRT
<213> ORGANISM: Bdellovibrio bacteriovorus

<400> SEQUENCE: 107

Met Lys Asn Tyr Leu Phe Thr Ser Glu Ser Val Ser Glu Gly His Pro
 1               5                  10                 15

Asp Lys Met Ala Asp Gln Ile Ser Asp Gly Ile Leu Asp Ala Ile Leu
              20                 25                 30

Ala Gln Asp Pro Lys Gly Arg Val Ala Cys Glu Thr Leu Leu Thr Thr
              35                 40                 45

Gly Leu Val Val Val Ala Gly Glu Ile Thr Thr Ser Ala Lys Val Asn
 50                  55                 60

Phe Ser Glu Val Ala Arg Asp Val Val Lys Arg Ile Gly Tyr Asp His
 65                  70                 75                 80
```

```
Ser Asp Lys Gly Phe Asp Tyr Lys Thr Cys Gly Val Met Ile Ala Val
                85                  90                  95

Gly Gln Gln Ser Pro Asp Ile Ala Val Gly Val Lys Glu Thr Leu Ser
            100                 105                 110

Asp Asn Gln Gly Ala Gly Asp Gln Gly Leu Met Phe Gly Tyr Ala Val
            115                 120                 125

Asn Glu Thr Pro Glu Leu Met Pro Leu Ser Ile Ala Met Ser His Lys
130                 135                 140

Leu Val Lys Asp Leu Ala Leu Arg Lys Ala Asn Lys Val Asp Trp
145                 150                 155                 160

Leu Arg Pro Asp Ala Lys Ser Gln Val Thr Val Gln Tyr Glu Asn Gly
                165                 170                 175

Ile Ala Lys Arg Ile Asp Ala Val Val Ile Ser Thr Gln His Ala Asp
            180                 185                 190

Ser Val Ser Asn Ser Thr Ile Gln Glu Phe Ile Thr Glu Glu Leu Ile
            195                 200                 205

Lys Lys Ser Ile Pro Gly Asn Trp Ile Asp Ser Lys Thr Lys Phe Phe
210                 215                 220

Ile Asn Pro Thr Gly Arg Phe Val Thr Gly Gly Pro Met Gly Asp Ala
225                 230                 235                 240

Gly Leu Thr Gly Arg Lys Ile Ile Val Asp Thr Tyr Gly Gly His Gly
                245                 250                 255

Ala His Gly Gly Gly Ala Phe Ser Gly Lys Asp Pro Ser Lys Val Asp
            260                 265                 270

Arg Ser Ala Ala Tyr Ala Ser Arg His Ile Ala Lys Asn Ile Val Gly
            275                 280                 285

Ala Gly Leu Ala Glu Arg Cys Leu Val Gln Val Ala Tyr Ala Ile Gly
290                 295                 300

Val Ala Glu Pro Val Ser Ile Thr Val Asn Asp Tyr Gly Thr Ser Lys
305                 310                 315                 320

Val Gly Pro Glu Val Leu Glu Lys Ala Val Arg Gln Val Phe Asp Leu
                325                 330                 335

Arg Pro Ala Arg Ile Thr Lys Asp Leu Asp Leu Leu Arg Pro Ile Tyr
            340                 345                 350

Ser Pro Thr Ala Ala Tyr Gly His Phe Gly Arg Asn Glu Glu Ser Phe
            355                 360                 365

Thr Trp Glu Arg Leu Asn Lys Val Asp Gln Leu Lys Asp Ala Val Lys
370                 375                 380

Thr Leu Ala
385

<210> SEQ ID NO 108
<211> LENGTH: 384
<212> TYPE: PRT
<213> ORGANISM: Escherichia coli

<400> SEQUENCE: 108

Met Ala Lys His Leu Phe Thr Ser Glu Ser Val Ser Glu Gly His Pro
1               5                   10                  15

Asp Lys Ile Ala Asp Gln Ile Ser Asp Ala Val Leu Asp Ala Ile Leu
            20                  25                  30

Glu Gln Asp Pro Lys Ala Arg Val Ala Cys Glu Thr Tyr Val Lys Thr
        35                  40                  45

Gly Met Val Leu Val Gly Gly Glu Ile Thr Thr Ser Ala Trp Val Asp
    50                  55                  60
```

Ile Glu Glu Ile Thr Arg Asn Thr Val Arg Glu Ile Gly Tyr Val His
65                  70                  75                  80

Ser Asp Met Gly Phe Asp Ala Asn Ser Cys Ala Val Leu Ser Ala Ile
                85                  90                  95

Gly Lys Gln Ser Pro Asp Ile Asn Gln Gly Val Asp Arg Ala Asp Pro
            100                 105                 110

Leu Glu Gln Gly Ala Gly Asp Gln Gly Leu Met Phe Gly Tyr Ala Thr
        115                 120                 125

Asn Glu Thr Asp Val Leu Met Pro Ala Pro Ile Thr Tyr Ala His Arg
    130                 135                 140

Leu Val Gln Arg Gln Ala Glu Val Arg Lys Asn Gly Thr Leu Pro Trp
145                 150                 155                 160

Leu Arg Pro Asp Ala Lys Ser Gln Val Thr Phe Gln Tyr Asp Asp Gly
                165                 170                 175

Lys Ile Val Gly Ile Asp Ala Val Val Leu Ser Thr Gln His Ser Glu
            180                 185                 190

Glu Ile Asp Gln Lys Ser Leu Gln Glu Ala Val Met Glu Glu Ile Ile
        195                 200                 205

Lys Pro Ile Leu Pro Ala Glu Trp Leu Thr Ser Ala Thr Lys Phe Phe
210                 215                 220

Ile Asn Pro Thr Gly Arg Phe Val Ile Gly Gly Pro Met Gly Asp Cys
225                 230                 235                 240

Gly Leu Thr Gly Arg Lys Ile Ile Val Asp Thr Tyr Gly Gly Met Ala
                245                 250                 255

Arg His Gly Gly Gly Ala Phe Ser Gly Lys Asp Pro Ser Lys Val Asp
            260                 265                 270

Arg Ser Ala Ala Tyr Ala Ala Arg Tyr Val Ala Lys Asn Ile Val Ala
        275                 280                 285

Ala Gly Leu Ala Asp Arg Cys Glu Ile Gln Val Ser Tyr Ala Ile Gly
    290                 295                 300

Val Ala Glu Pro Thr Ser Ile Met Val Glu Thr Phe Gly Thr Glu Lys
305                 310                 315                 320

Val Pro Ser Glu Gln Leu Thr Leu Leu Val Arg Glu Phe Phe Asp Leu
                325                 330                 335

Arg Pro Tyr Gly Leu Ile Gln Met Leu Asp Leu Leu His Pro Ile Tyr
            340                 345                 350

Lys Glu Thr Ala Ala Tyr Gly His Phe Gly Arg Glu His Phe Pro Trp
        355                 360                 365

Glu Lys Thr Asp Lys Ala Gln Leu Leu Arg Asp Ala Ala Gly Leu Lys
    370                 375                 380

<210> SEQ ID NO 109
<211> LENGTH: 384
<212> TYPE: PRT
<213> ORGANISM: Salmonella typhimurium

<400> SEQUENCE: 109

Met Ala Lys His Leu Phe Thr Ser Glu Ser Val Ser Glu Gly His Pro
1               5                   10                  15

Asp Lys Ile Ala Asp Gln Ile Ser Asp Ala Val Leu Asp Ala Ile Leu
            20                  25                  30

Gln Gln Asp Pro Lys Ala Arg Val Ala Cys Glu Thr Tyr Val Lys Thr
        35                  40                  45

Gly Met Val Leu Val Gly Gly Glu Ile Thr Thr Ser Ala Trp Val Asp

```
            50                  55                  60
Ile Glu Glu Ile Thr Arg Asn Thr Val Arg Glu Ile Gly Tyr Val His
 65                  70                  75                  80

Ser Asp Met Gly Phe Asp Ala Asn Ser Cys Ala Val Leu Ser Ala Ile
                 85                  90                  95

Gly Lys Gln Ser Pro Asp Ile Asn Gln Gly Val Asp Arg Ala Asp Pro
                100                 105                 110

Leu Glu Gln Gly Ala Gly Asp Gln Gly Leu Met Phe Gly Tyr Ala Thr
            115                 120                 125

Asn Glu Thr Asp Val Leu Met Pro Ala Pro Ile Thr Tyr Ala His Arg
            130                 135                 140

Leu Val Gln Arg Gln Ala Glu Val Arg Lys Asn Gly Thr Leu Pro Trp
145                 150                 155                 160

Leu Arg Pro Asp Ala Lys Ser Gln Val Thr Phe Gln Tyr Asp Asp Gly
                165                 170                 175

Lys Ile Val Gly Ile Asp Ala Val Val Leu Ser Thr Gln His Ala Glu
                180                 185                 190

Asp Ile Asp Gln Lys Ser Leu Gln Glu Ala Val Met Glu Glu Ile Ile
            195                 200                 205

Lys Pro Ile Leu Pro Ser Glu Trp Leu Asn Thr Ser Thr Lys Phe Phe
210                 215                 220

Ile Asn Pro Thr Gly Arg Phe Val Ile Gly Gly Pro Met Gly Asp Cys
225                 230                 235                 240

Gly Leu Thr Gly Arg Lys Ile Ile Val Asp Thr Tyr Gly Gly Met Ala
                245                 250                 255

Arg His Gly Gly Gly Ala Phe Ser Gly Lys Asp Pro Ser Lys Val Asp
                260                 265                 270

Arg Ser Ala Ala Tyr Ala Ala Arg Tyr Val Ala Lys Asn Ile Val Ala
            275                 280                 285

Ala Gly Leu Ala Asp Arg Cys Glu Ile Gln Val Ser Tyr Ala Ile Gly
            290                 295                 300

Val Ala Glu Pro Thr Ser Ile Met Val Glu Thr Phe Gly Thr Glu Lys
305                 310                 315                 320

Val Pro Ala Glu Gln Leu Ile Leu Leu Val Arg Glu Phe Phe Asp Leu
                325                 330                 335

Arg Pro Tyr Gly Leu Ile Gln Met Leu Asp Leu Leu His Pro Ile Tyr
                340                 345                 350

Lys Glu Thr Ala Ala Tyr Gly His Phe Gly Arg Glu Asn Phe Pro Trp
            355                 360                 365

Glu Lys Thr Asp Lys Ala Gln Leu Leu Arg Asp Ala Ala Gly Leu Lys
            370                 375                 380

<210> SEQ ID NO 110
<211> LENGTH: 384
<212> TYPE: PRT
<213> ORGANISM: Yersinia pestis

<400> SEQUENCE: 110

Met Ala Lys His Leu Phe Thr Ser Glu Ser Val Ser Glu Gly His Pro
 1               5                  10                  15

Asp Lys Ile Ala Asp Gln Ile Ser Asp Ala Val Leu Asp Ala Ile Leu
                20                  25                  30

Glu Gln Asp Pro Lys Ala Arg Val Ala Cys Glu Thr Tyr Val Lys Thr
            35                  40                  45
```

Gly Met Val Leu Val Gly Gly Glu Val Thr Thr Asn Ala Trp Val Asp
    50              55                  60

Ile Glu Glu Ile Thr Arg Arg Thr Ile Arg Glu Ile Gly Tyr Val His
65              70                  75                  80

Ser Asp Met Gly Phe Asp Ala Asn Ser Cys Ala Val Leu Ser Ala Ile
                85                  90                  95

Gly Lys Gln Ser Pro Asp Ile Asn Gln Gly Val Asp Arg Glu Asn Pro
                100                 105                 110

Leu Glu Gln Gly Ala Gly Asp Gln Gly Leu Met Phe Gly Tyr Ala Thr
            115                 120                 125

Asn Glu Thr Ser Val Leu Met Pro Ala Pro Ile Thr Tyr Ala His Arg
    130                 135                 140

Leu Val Glu Arg Gln Ala Glu Val Arg Lys Asn Gly Ala Leu Pro Trp
145                 150                 155                 160

Leu Arg Pro Asp Ala Lys Ser Gln Val Thr Phe Gln Tyr Asp Asp Gly
                165                 170                 175

Lys Ile Val Gly Ile Asp Ala Val Val Leu Ser Thr Gln His Ser Glu
                180                 185                 190

Asp Ile Asn Gln Lys Asp Leu His Glu Ala Val Met Glu Glu Ile Ile
    195                 200                 205

Lys Pro Val Leu Pro Ala Glu Trp Ile Thr Ala His Thr Lys Tyr Phe
210                 215                 220

Ile Asn Pro Thr Gly Arg Phe Val Ile Gly Pro Met Gly Asp Cys
225                 230                 235                 240

Gly Leu Thr Gly Arg Lys Ile Ile Val Asp Thr Tyr Gly Gly Met Ala
                245                 250                 255

Arg His Gly Gly Gly Ala Phe Ser Gly Lys Asp Pro Ser Lys Val Asp
                260                 265                 270

Arg Ser Ala Ala Tyr Ala Ala Arg Tyr Val Ala Lys Asn Ile Val Ala
            275                 280                 285

Ala Gly Leu Ala Asp Arg Cys Glu Ile Gln Val Ser Tyr Ala Ile Gly
    290                 295                 300

Val Ala Glu Pro Thr Ser Ile Met Val Glu Ala Phe Gly Thr Glu Lys
305                 310                 315                 320

Ile Pro Ala Asp Gln Leu Thr Leu Leu Val Arg Glu Phe Phe Asp Leu
                325                 330                 335

Arg Pro Tyr Gly Leu Ile Lys Met Leu Asp Leu Leu His Pro Ile Tyr
                340                 345                 350

Arg Glu Thr Ala Ala Tyr Gly His Phe Gly Arg Glu His Phe Pro Trp
            355                 360                 365

Glu Lys Thr Asp Lys Ala Ala Leu Leu Arg Asp Ala Ala Gly Leu Lys
    370                 375                 380

<210> SEQ ID NO 111
<211> LENGTH: 390
<212> TYPE: PRT
<213> ORGANISM: Photorhabdus luminescens

<400> SEQUENCE: 111

Met Thr Thr Tyr Leu Phe Thr Ser Glu Ser Val Ser Glu Gly His Pro
1               5                   10                  15

Asp Lys Ile Ala Asp Gln Ile Ser Asp Ala Val Leu Asp Ala Ile Leu
            20                  25                  30

Glu Gln Asp Pro Lys Ala Arg Val Ala Cys Glu Thr Tyr Val Lys Thr
        35                  40                  45

Gly Met Val Met Gly Gly Glu Ile Thr Thr Ser Ala Trp Val Asp
    50                  55                  60

Ile Glu Glu Ile Thr Arg Gln Thr Val Arg Glu Ile Gly Tyr Val Asn
65                  70                  75                  80

Ser Glu Met Gly Phe Asp Ala Asn Ser Cys Ala Val Leu Ser Ala Ile
                85                  90                  95

Gly Lys Gln Ser Pro Asp Ile Asn Gln Gly Val Asp Arg Glu Asp Pro
            100                 105                 110

Leu Gln Gln Gly Ala Gly Asp Gln Gly Leu Met Phe Gly Tyr Ala Thr
        115                 120                 125

Asn Glu Thr Asp Val Leu Met Pro Ala Pro Ile Thr Tyr Ala His Arg
    130                 135                 140

Leu Val Gln Arg Gln Ala Glu Val Arg Lys Asn Gly Val Leu Pro Trp
145                 150                 155                 160

Leu Arg Pro Asp Ala Lys Ser Gln Val Thr Phe Gln Tyr Asn Asn Asp
                165                 170                 175

Lys Ile Val Gly Val Asp Ala Val Val Leu Ser Thr Gln His Ala Glu
            180                 185                 190

Asn Ile Ser Gln Lys Asp Leu Gln Glu Ala Val Met Glu Glu Ile Ile
        195                 200                 205

Lys Pro Val Leu Pro Ala Glu Trp Leu Asn Pro Thr Thr Lys Tyr Phe
    210                 215                 220

Ile Asn Pro Thr Gly Arg Phe Val Ile Gly Gly Pro Met Gly Asp Cys
225                 230                 235                 240

Gly Leu Thr Gly Arg Lys Ile Ile Val Asp Thr Tyr Gly Gly Met Ala
                245                 250                 255

Arg His Gly Gly Gly Ala Phe Ser Gly Lys Asp Pro Ser Lys Val Asp
            260                 265                 270

Arg Ser Ala Ala Tyr Ala Ala Arg Tyr Val Ala Lys Asn Ile Val Ala
        275                 280                 285

Ala Gly Leu Ala Asp Arg Cys Glu Ile Gln Val Ser Tyr Ala Ile Gly
    290                 295                 300

Val Ala Glu Pro Thr Ser Ile Met Val Glu Thr Phe Gly Thr Glu Lys
305                 310                 315                 320

Val Ser Thr Ala Thr Leu Thr Leu Leu Val Arg Glu Phe Phe Asp Leu
                325                 330                 335

Arg Pro His Gly Leu Ile Gln Met Leu Asp Leu Leu His Pro Ile Tyr
            340                 345                 350

Arg Asp Thr Ala Ala Tyr Gly His Phe Gly Arg Pro Gln Phe Pro Trp
        355                 360                 365

Glu Ala Thr Asp Lys Ala Glu Ala Leu Arg Asp Ala Ala Gly Leu Lys
    370                 375                 380

Leu Ser Ala Met Asn Met
385                 390

<210> SEQ ID NO 112
<211> LENGTH: 384
<212> TYPE: PRT
<213> ORGANISM: Vibrio vulnificus

<400> SEQUENCE: 112

Met Ala Lys His Leu Phe Thr Ser Glu Ser Val Ser Glu Gly His Pro
1               5                   10                  15

Asp Lys Ile Ala Asp Gln Ile Ser Asp Ala Val Leu Asp Ala Ile Leu

```
            20                  25                  30
Glu Gln Asp Pro Lys Ala Arg Val Ala Cys Glu Thr Tyr Val Lys Thr
        35                  40                  45

Gly Met Val Met Val Gly Gly Glu Ile Thr Thr Ser Ala Trp Val Asp
    50                  55                  60

Ile Glu Glu Leu Thr Arg Glu Thr Val Arg Glu Ile Gly Tyr Val His
65                  70                  75                  80

Ser Asp Met Gly Phe Asp Ala Asn Ser Cys Ala Val Leu Asn Thr Ile
                85                  90                  95

Gly Lys Gln Ser Pro Asp Ile Asn Gln Gly Val Asp Lys Ala Asp Pro
            100                 105                 110

Lys Glu Gln Gly Ala Gly Asp Gln Gly Ile Met Phe Gly Tyr Ala Cys
        115                 120                 125

Asn Glu Thr Glu Val Leu Met Pro Ala Pro Ile Thr Tyr Ala His Arg
    130                 135                 140

Leu Met Glu Arg Gln Ala Lys Val Arg Lys Asp Gly Thr Leu Pro Trp
145                 150                 155                 160

Leu Arg Pro Asp Ala Lys Ser Gln Val Thr Phe Gln Tyr Glu Gln Gly
                165                 170                 175

Lys Ile Val Gly Ile Asp Ala Val Val Leu Ser Thr Gln His Cys Asp
            180                 185                 190

Ser Ile Ser Thr Pro Asp Leu Arg Glu Ala Val Met Glu Glu Ile Ile
        195                 200                 205

Lys Pro Val Leu Pro Ser Glu Trp Leu Asn Lys Glu Thr Lys Tyr Phe
    210                 215                 220

Ile Asn Pro Thr Gly Arg Phe Val Ile Gly Gly Pro Met Gly Asp Cys
225                 230                 235                 240

Gly Leu Thr Gly Arg Lys Ile Ile Val Asp Thr Tyr Gly Gly Ala Ala
                245                 250                 255

Arg His Gly Gly Gly Ala Phe Ser Gly Lys Asp Pro Ser Lys Val Asp
            260                 265                 270

Arg Ser Ala Ala Tyr Ala Ala Arg Tyr Val Ala Lys Asn Ile Val Ala
        275                 280                 285

Ala Gly Met Ala Asp Arg Cys Glu Ile Gln Leu Ser Tyr Ala Ile Gly
    290                 295                 300

Val Ala Asp Pro Thr Ser Ile Met Val Glu Thr Phe Gly Thr Glu Lys
305                 310                 315                 320

Val Ser His Asp Ile Ile Ile Glu Ala Val Arg Gln Phe Phe Asp Leu
                325                 330                 335

Arg Pro Tyr Gly Leu Gln Glu Met Leu Asn Leu Gln Pro Ile Tyr
            340                 345                 350

Lys Lys Thr Ala Ala Tyr Gly His Phe Gly Arg Glu Glu Phe Pro Trp
        355                 360                 365

Glu Ala Thr Asp Lys Ala Ala Leu Leu Arg Glu Phe Ala Gly Ile Lys
    370                 375                 380

<210> SEQ ID NO 113
<211> LENGTH: 386
<212> TYPE: PRT
<213> ORGANISM: Haemophilus ducreyi

<400> SEQUENCE: 113

Met Arg Leu Asn Ser Met Ala Ile Asn Leu Phe Thr Ser Glu Ser Val
1               5                   10                  15
```

```
Ser Glu Gly His Pro Asp Lys Ile Ala Asp Gln Ile Ser Asp Ala Val
            20                  25                  30

Leu Asp Glu Ile Leu Lys Gln Asp Pro Lys Ala Arg Val Ala Cys Glu
        35                  40                  45

Thr Tyr Val Lys Thr Gly Met Ala Leu Val Gly Gly Glu Ile Thr Thr
    50                  55                  60

Ser Ala Trp Val Asp Ile Glu Asn Leu Thr Arg Gln Val Ile Tyr Asp
65                  70                  75                  80

Ile Gly Tyr Ser His Ser Asp Met Gly Phe Asp Ala His Ser Cys Ala
                85                  90                  95

Val Leu Asn Ala Ile Gly Lys Gln Ser Pro Asp Ile Asn Gln Gly Val
            100                 105                 110

Asp Arg Glu Asp Pro Leu Ala Gln Gly Ala Gly Asp Gln Gly Ile Met
        115                 120                 125

Phe Gly Tyr Ala Thr Asn Glu Thr Asp Val Leu Met Pro Ala Pro Ile
130                 135                 140

Thr Tyr Ala His Arg Leu Met Gln Arg Gln Ala Glu Val Arg Lys Ser
145                 150                 155                 160

Gly Lys Leu Ala Trp Leu Arg Pro Asp Ala Lys Ser Gln Leu Thr Phe
                165                 170                 175

Ala Tyr Glu Asn Asn Gln Ile Ile Gly Ile Asp Ala Val Val Leu Ser
            180                 185                 190

Thr Gln His Ala Glu Glu Val Lys Gln Lys Leu Ile Glu Gly Val
        195                 200                 205

Met Glu Glu Ile Ile Lys Pro Thr Leu Pro Ser Lys Trp Leu Asn Gln
210                 215                 220

His Thr Lys Tyr Phe Ile Asn Pro Thr Gly Arg Phe Val Ile Gly Gly
225                 230                 235                 240

Pro Met Gly Asp Cys Gly Leu Thr Gly Arg Lys Ile Ile Val Asp Thr
                245                 250                 255

Tyr Gly Gly Ala Ala Arg His Gly Gly Gly Ala Phe Ser Gly Lys Asp
            260                 265                 270

Pro Ser Lys Val Asp Arg Ser Ala Ala Tyr Ala Ala Arg Tyr Val Ala
        275                 280                 285

Lys Ser Ile Val Ala Gly Leu Ala Asp Arg Cys Glu Ile Gln Leu
290                 295                 300

Ser Tyr Ala Ile Gly Val Ala Asp Pro Thr Ser Ile Met Val Glu Thr
305                 310                 315                 320

Phe Gly Thr Gly Lys Val Ser Asn Asp Thr Leu Val Lys Leu Ile Tyr
                325                 330                 335

Gln Asn Phe Asp Leu Arg Pro Tyr Gly Leu Ile Lys Met Leu Asp Leu
            340                 345                 350

Ile Gln Pro Ile Tyr Arg Glu Thr Ala Ala Tyr Gly His Phe Gly Arg
        355                 360                 365

Glu Gln Phe Pro Trp Glu Arg Thr Asp Lys Ala Glu Ala Leu Arg Leu
370                 375                 380

Ala Leu
385

<210> SEQ ID NO 114
<211> LENGTH: 385
<212> TYPE: PRT
<213> ORGANISM: Blochmannia floridanus

<400> SEQUENCE: 114
```

```
Met Thr Arg Phe Leu Phe Thr Ser Glu Ser Val Ser Ala Gly His Pro
1               5                   10                  15

Asp Lys Ile Ala Asp Gln Ile Ser Asp Ser Ile Leu Asp Ser Ile Leu
            20                  25                  30

Glu Gln Asp Pro Lys Ala Arg Val Ala Cys Glu Thr Tyr Ile Lys Thr
        35                  40                  45

Gly Ile Val Leu Ile Gly Gly Glu Ile Thr Thr Ala Ser Val Asn
    50                  55                  60

Ile Glu Lys Ile Ala Arg Asn Thr Ile Gln Glu Ile Gly Tyr Thr His
65                  70                  75                  80

Pro Lys Met Gly Leu Asp Ala Asn Ser Cys Val Ile Leu Ser Val Ile
                85                  90                  95

Asn Gln Gln Ser Pro Glu Ile Gln Tyr Ser Ile Asn His Asp Ser Asp
                100                 105                 110

Arg Thr Gln Gln Gly Ala Gly Asp Gln Gly Ser Met Phe Gly Tyr Ala
                115                 120                 125

Thr Asn Glu Thr Asp Val Leu Met Pro Ala Pro Ile Thr Tyr Ala His
    130                 135                 140

Arg Leu Ile Gln Arg Lys Ser Lys Leu Arg Lys Asn Gly Thr Leu Pro
145                 150                 155                 160

Trp Leu Gly Leu Asp Ala Lys Ser Gln Ile Thr Phe Ala Tyr Asp Glu
                165                 170                 175

Asn Asn Lys Ile Ile His Ile Thr Ala Val Val Leu Ser Val Gln His
                180                 185                 190

Asn Lys Asn Ile Pro Leu Glu Ala Leu Arg Glu Ala Thr Met Glu Glu
            195                 200                 205

Ile Ile Lys Pro Val Leu Pro Gln Lys Trp Leu Ser Lys Gln Thr Lys
210                 215                 220

Phe Phe Ile Asn Ser Gly Gly Thr Phe Thr Ile Gly Ser Pro Ile Ser
225                 230                 235                 240

Asp Cys Gly Leu Thr Gly Arg Lys Ile Ile Val Asp Thr Tyr Gly Gly
                245                 250                 255

Met Ala Arg His Gly Gly Gly Ser Phe Ser Gly Lys Asp Pro Ser Lys
                260                 265                 270

Val Asp Arg Ser Ala Ala Tyr Ala Ala Arg Tyr Ala Ala Lys Asn Ile
    275                 280                 285

Val Ala Ala Gly Leu Ala Glu Arg Cys Glu Ile Gln Leu Ala Tyr Ala
    290                 295                 300

Ile Gly Ile Ala Asn Pro Ile Ala Val Asn Ile Glu Thr Phe Gly Thr
305                 310                 315                 320

Glu Lys Val Leu His Ser Thr Leu Val Thr Leu Ile Asn Asn Phe Phe
                325                 330                 335

Asp Phe Ser Pro His Gly Val Ile Lys Met Leu Asn Leu Ala Arg Pro
                340                 345                 350

Ile Tyr Lys Asp Thr Ala Val Tyr Gly His Phe Gly Arg Glu Gln Phe
            355                 360                 365

Pro Trp Glu Lys Ile Asp Lys Val Asp Leu Leu Arg Asn Ser Ala Lys
370                 375                 380

Ile
385

<210> SEQ ID NO 115
<211> LENGTH: 387
```

```
<212> TYPE: PRT
<213> ORGANISM: Borrelia burgdorferi

<400> SEQUENCE: 115

Met Ala Asn Asn Asp Phe Leu Phe Thr Ser Glu Ser Val Ser Glu Gly
1               5                   10                  15

His Pro Asp Lys Val Ala Asp Gln Ile Ser Asp Ala Ile Leu Asp Ala
            20                  25                  30

Ile Phe Thr Gln Asp Pro Asn Ala Arg Val Ala Glu Thr Leu Cys
        35                  40                  45

Asn Thr Gly Leu Val Val Leu Ala Gly Glu Ile Thr Thr Thr Ala Asn
    50                  55                  60

Val Asp Tyr Ile Gln Val Ala Arg Asp Thr Ile Arg His Ile Gly Tyr
65                  70                  75                  80

Asp Asn Thr Glu Tyr Gly Ile Asp Tyr Lys Gly Cys Ala Val Leu Val
                85                  90                  95

Ala Tyr Asp Lys Gln Ser Pro Asp Ile Ala Gln Gly Val Asp Arg Ser
            100                 105                 110

Ser Glu Asp Tyr Leu Asn Gln Gly Ala Gly Asp Gln Gly Leu Met Phe
        115                 120                 125

Gly Tyr Ala Cys Asp Glu Thr Pro Asp Leu Met Pro Ala Pro Ile Trp
130                 135                 140

Tyr Ala His Arg Leu Val Gln Arg Gln Ser Glu Leu Arg Lys Asp Gly
145                 150                 155                 160

Arg Leu Pro Trp Leu Arg Pro Asp Ala Lys Ser Gln Val Thr Phe Arg
                165                 170                 175

Tyr Val Asp Gly Arg Pro Ala Glu Val Asp Thr Val Val Leu Ser Thr
            180                 185                 190

Gln His Ser Pro Glu Ile Ser Gln Ala Ser Ile Arg Glu Ala Val Ile
        195                 200                 205

Glu Asp Ile Ile Lys Pro Ser Phe Pro Glu Gly Leu Ile Thr Pro Lys
    210                 215                 220

Thr Lys Phe Leu Val Asn Pro Thr Gly Arg Phe Val Ile Gly Gly Pro
225                 230                 235                 240

Gln Gly Asp Cys Gly Leu Thr Gly Arg Lys Ile Ile Val Asp Thr Tyr
                245                 250                 255

Gly Gly Ala Cys Pro His Gly Gly Ala Phe Ser Gly Lys Asp Pro
            260                 265                 270

Ser Lys Val Asp Arg Ser Ala Ala Tyr Ala Ala Arg Tyr Val Ala Lys
        275                 280                 285

Asn Val Val Ala Ala Gly Leu Ala Arg Gln Cys Gln Val Gln Val Ser
    290                 295                 300

Tyr Ala Ile Gly Val Ala Glu Pro Ile Asn Ile Thr Val Tyr Thr Glu
305                 310                 315                 320

Gly Thr Gly Val Ile Pro Asp Glu Gln Ile Ala Lys Leu Val Arg Glu
                325                 330                 335

His Phe Asp Leu Arg Pro Lys Gly Ile Val Asn Met Leu Asp Leu Leu
            340                 345                 350

Arg Pro Ile Tyr Thr Lys Thr Ala Ala Tyr Gly His Phe Gly Arg Ser
        355                 360                 365

Glu Pro Glu Phe Ser Trp Glu Ala Thr Asp Lys Ala Ala Ala Leu Lys
    370                 375                 380

Gln Gly Ala
385
```

<210> SEQ ID NO 116
<211> LENGTH: 387
<212> TYPE: PRT
<213> ORGANISM: Bordetella parapertussis

<400> SEQUENCE: 116

```
Met Ala Asn Asn Asp Phe Leu Phe Thr Ser Glu Ser Val Ser Glu Gly
1               5                   10                  15

His Pro Asp Lys Val Ala Asp Gln Ile Ser Asp Ala Ile Leu Asp Ala
            20                  25                  30

Ile Phe Thr Gln Asp Pro Asn Ala Arg Val Ala Glu Thr Leu Cys
        35                  40                  45

Asn Thr Gly Leu Val Val Leu Ala Gly Glu Ile Thr Thr Thr Ala Asn
    50                  55                  60

Val Asp Tyr Ile Gln Val Ala Arg Asp Thr Ile Arg His Ile Gly Tyr
65                  70                  75                  80

Asp Asn Thr Glu Tyr Gly Ile Asp Tyr Lys Gly Cys Ala Val Leu Val
                85                  90                  95

Ala Tyr Asp Lys Gln Ser Pro Asp Ile Ala Gln Gly Val Asp Arg Ser
            100                 105                 110

Ser Glu Asp Tyr Leu Asn Gln Gly Ala Gly Asp Gln Gly Leu Met Phe
        115                 120                 125

Gly Tyr Ala Cys Asp Glu Thr Pro Asp Leu Met Pro Ala Pro Ile Trp
    130                 135                 140

Tyr Ala His Arg Leu Val Gln Arg Gln Ser Glu Leu Arg Lys Asp Gly
145                 150                 155                 160

Arg Leu Pro Trp Leu Arg Pro Asp Ala Lys Ser Gln Val Thr Phe Arg
                165                 170                 175

Tyr Val Asp Gly Arg Pro Ala Glu Val Asp Thr Val Val Leu Ser Thr
            180                 185                 190

Gln His Ser Pro Glu Ile Ser Gln Ala Ser Ile Arg Glu Ala Val Ile
        195                 200                 205

Glu Asp Ile Ile Lys Pro Ser Phe Pro Glu Gly Leu Ile Thr Pro Lys
    210                 215                 220

Thr Lys Phe Leu Val Asn Pro Thr Gly Arg Phe Val Ile Gly Gly Pro
225                 230                 235                 240

Gln Gly Asp Cys Gly Leu Thr Gly Arg Lys Ile Ile Val Asp Thr Tyr
                245                 250                 255

Gly Gly Ala Cys Pro His Gly Gly Ala Phe Ser Gly Lys Asp Pro
            260                 265                 270

Ser Lys Val Asp Arg Ser Ala Ala Tyr Ala Ala Arg Tyr Val Ala Lys
        275                 280                 285

Asn Val Val Ala Ala Gly Leu Ala Arg Gln Cys Gln Val Gln Val Ser
    290                 295                 300

Tyr Ala Ile Gly Val Ala Glu Pro Ile Asn Ile Thr Val Tyr Thr Glu
305                 310                 315                 320

Gly Thr Gly Val Ile Pro Asp Glu Gln Ile Ala Lys Leu Val Arg Glu
                325                 330                 335

His Phe Asp Leu Arg Pro Lys Gly Ile Val Asn Met Leu Asp Leu Leu
            340                 345                 350

Arg Pro Ile Tyr Thr Lys Thr Ala Ala Tyr Gly His Phe Gly Arg Ser
        355                 360                 365

Glu Pro Glu Phe Ser Trp Glu Ala Thr Asp Lys Ala Ala Ala Leu Lys
```

370                 375                 380

Gln Gly Ala
385

<210> SEQ ID NO 117
<211> LENGTH: 387
<212> TYPE: PRT
<213> ORGANISM: Bordetella pertussis

<400> SEQUENCE: 117

Met Ala Asn Asn Asp Phe Leu Phe Thr Ser Glu Ser Val Ser Glu Gly
1               5                   10                  15

His Pro Asp Lys Val Ala Asp Gln Ile Ser Asp Ala Ile Leu Asp Ala
            20                  25                  30

Ile Phe Thr Gln Asp Pro Asn Ala Arg Val Ala Ala Glu Thr Leu Cys
        35                  40                  45

Asn Thr Gly Leu Val Val Leu Ala Gly Glu Ile Thr Thr Thr Ala Asn
    50                  55                  60

Val Asp Tyr Ile Gln Val Ala Arg Asp Thr Ile Arg His Ile Gly Tyr
65                  70                  75                  80

Asp Asn Thr Glu Tyr Gly Ile Asp Tyr Lys Gly Cys Ala Val Leu Val
                85                  90                  95

Ala Tyr Asp Lys Gln Ser Pro Asp Ile Ala Gln Gly Val Asp Arg Ser
            100                 105                 110

Ser Glu Asp Tyr Leu Asn Gln Gly Ala Gly Asp Gln Gly Leu Met Phe
        115                 120                 125

Gly Tyr Ala Cys Asp Glu Thr Pro Asp Leu Met Pro Ala Pro Ile Trp
130                 135                 140

Tyr Ala His Arg Leu Val Gln Arg Gln Ser Glu Leu Arg Lys Asp Gly
145                 150                 155                 160

Arg Leu Pro Trp Leu Arg Pro Asp Ala Lys Ser Gln Val Thr Phe Arg
                165                 170                 175

Tyr Val Asp Gly Arg Pro Ala Glu Val Asp Thr Val Val Leu Ser Thr
            180                 185                 190

Gln His Ser Pro Glu Ile Ser Gln Ala Ser Ile Arg Glu Ala Val Ile
        195                 200                 205

Glu Asp Ile Ile Lys Pro Ser Phe Pro Glu Gly Leu Ile Thr Pro Lys
    210                 215                 220

Thr Lys Phe Leu Val Asn Pro Thr Gly Arg Phe Val Ile Gly Gly Pro
225                 230                 235                 240

Gln Gly Asp Cys Gly Leu Thr Gly Arg Lys Ile Ile Val Asp Thr Tyr
                245                 250                 255

Gly Gly Ala Cys Pro His Gly Gly Ala Phe Ser Gly Lys Asp Pro
            260                 265                 270

Ser Lys Val Asp Arg Ser Ala Ala Tyr Ala Ala Arg Tyr Val Ala Lys
        275                 280                 285

Asn Val Val Ala Ala Gly Leu Ala Arg Gln Cys Gln Val Gln Val Ser
    290                 295                 300

Tyr Ala Ile Gly Val Ala Glu Pro Ile Asn Ile Thr Val Tyr Thr Glu
305                 310                 315                 320

Gly Thr Gly Val Ile Pro Asp Glu Gln Ile Ala Lys Leu Val Arg Glu
                325                 330                 335

His Phe Asp Leu Arg Pro Lys Gly Ile Val Asn Met Leu Asp Leu Leu
            340                 345                 350

```
Arg Pro Ile Tyr Thr Lys Thr Ala Ala Tyr Gly His Phe Gly Arg Ser
        355                 360                 365

Glu Pro Glu Phe Ser Trp Glu Ala Thr Asp Lys Ala Ala Ala Leu Lys
370                 375                 380

Gln Gly Ala
385

<210> SEQ ID NO 118
<211> LENGTH: 432
<212> TYPE: PRT
<213> ORGANISM: Bordetella parapertussis

<400> SEQUENCE: 118

Met Ala Leu Val Arg Gln Val Arg Ala Lys Ser Ala Lys Ala Ser Arg
1               5                   10                  15

Pro Asp Leu Pro Tyr Ile Ala Ile Pro Gly Cys Ser Ala Pro Arg Asn
            20                  25                  30

Leu Cys Ala Gly Phe Arg Pro Val Arg Glu Glu Val Ser Val Ala Asn
        35                  40                  45

Asn Asp Phe Leu Phe Thr Ser Glu Ser Val Ser Glu Gly His Pro Asp
    50                  55                  60

Lys Val Ala Asp Gln Ile Ser Asp Ala Ile Leu Asp Ala Ile Phe Thr
65                  70                  75                  80

Gln Asp Pro Asn Ala Arg Val Ala Ala Glu Thr Leu Cys Asn Thr Gly
                85                  90                  95

Leu Val Val Leu Ala Gly Glu Ile Thr Thr Thr Ala Asn Val Asp Tyr
            100                 105                 110

Ile Gln Val Ala Arg Asp Thr Ile Arg His Ile Gly Tyr Asp Asn Thr
        115                 120                 125

Glu Tyr Gly Ile Asp Tyr Lys Gly Cys Ala Val Leu Val Ala Tyr Asp
    130                 135                 140

Lys Gln Ser Pro Asp Ile Ala Gln Gly Val Asp Arg Ser Ser Glu Asp
145                 150                 155                 160

Tyr Leu Asn Gln Gly Ala Gly Asp Gln Gly Leu Met Phe Gly Tyr Ala
                165                 170                 175

Cys Asp Glu Thr Pro Asp Leu Met Pro Ala Pro Ile Trp Tyr Ala His
            180                 185                 190

Arg Leu Val Gln Arg Gln Ser Glu Leu Arg Lys Asp Gly Arg Leu Pro
        195                 200                 205

Trp Leu Arg Pro Asp Ala Lys Ser Gln Val Thr Phe Arg Tyr Val Asp
    210                 215                 220

Gly Arg Pro Ala Glu Val Asp Thr Val Val Leu Ser Thr Gln His Ser
225                 230                 235                 240

Pro Glu Ile Ser Gln Ala Ser Ile Arg Glu Ala Val Ile Glu Asp Ile
                245                 250                 255

Ile Lys Pro Ser Phe Pro Glu Gly Leu Ile Thr Pro Lys Thr Lys Phe
            260                 265                 270

Leu Val Asn Pro Thr Gly Arg Phe Val Ile Gly Gly Pro Gln Gly Asp
        275                 280                 285

Cys Gly Leu Thr Gly Arg Lys Ile Ile Val Asp Thr Tyr Gly Gly Ala
    290                 295                 300

Cys Pro His Gly Gly Gly Ala Phe Ser Gly Lys Asp Pro Ser Lys Val
305                 310                 315                 320

Asp Arg Ser Ala Ala Tyr Ala Ala Arg Tyr Val Ala Lys Asn Val Val
                325                 330                 335
```

```
Ala Ala Gly Leu Ala Arg Gln Cys Gln Val Gln Val Ser Tyr Ala Ile
            340                 345                 350

Gly Val Ala Glu Pro Ile Asn Ile Thr Val Tyr Thr Glu Gly Thr Gly
            355                 360                 365

Val Ile Pro Asp Glu Gln Ile Ala Lys Leu Val Arg Glu His Phe Asp
370                 375                 380

Leu Arg Pro Lys Gly Ile Val Asn Met Leu Asp Leu Leu Arg Pro Ile
385                 390                 395                 400

Tyr Thr Lys Thr Ala Ala Tyr Gly His Phe Gly Arg Ser Glu Pro Glu
            405                 410                 415

Phe Ser Trp Glu Ala Thr Asp Lys Ala Ala Leu Lys Gln Gly Ala
            420                 425                 430

<210> SEQ ID NO 119
<211> LENGTH: 386
<212> TYPE: PRT
<213> ORGANISM: Helicobacter hepaticus

<400> SEQUENCE: 119

Met Lys Lys Ser Phe Leu Phe Thr Ser Glu Ser Val Thr Glu Gly His
1               5                   10                  15

Pro Asp Lys Met Ala Asp Gln Ile Ser Asp Ala Val Leu Asp Tyr Ile
            20                  25                  30

Ile Glu Arg Asp Lys Lys Ala Arg Val Ala Cys Glu Thr Leu Val Ser
            35                  40                  45

Asn Gly Phe Cys Val Ile Ala Gly Glu Leu Lys Thr Ser Val Tyr Ala
        50                  55                  60

Pro Met Gln Glu Ile Ala Arg Lys Val Val Gln Glu Ile Gly Tyr Thr
65                  70                  75                  80

Asp Ala Leu Tyr Gly Phe Asp Tyr Arg Ser Ala Ala Val Leu Asn Gly
                85                  90                  95

Ile Gly Glu Gln Ser Pro Asp Ile Asn Gln Gly Val Asp Arg Glu Asp
            100                 105                 110

Gly Glu Ile Gly Ala Gly Asp Gln Gly Leu Met Phe Gly Tyr Ala Cys
        115                 120                 125

Lys Glu Thr Pro Ser Leu Met Pro Leu Pro Ile Trp Leu Ser His Arg
130                 135                 140

Leu Thr Glu Gly Leu Ala Lys Lys Arg Lys Asp Gly Thr Leu Pro Phe
145                 150                 155                 160

Leu Arg Pro Asp Gly Lys Ser Gln Val Thr Val Arg Tyr Glu Asp Gly
                165                 170                 175

Lys Pro Val Ser Ile Asp Thr Ile Val Ile Ser Thr Gln His Ser Pro
            180                 185                 190

Glu Thr Gln Gln Ser His Leu Lys Asp Ala Val Ile Glu Glu Ile Val
        195                 200                 205

Gln Lys Val Leu Pro Gln Glu Tyr Leu Asn Asp Asn Ile Arg Tyr Phe
210                 215                 220

Val Asn Pro Thr Gly Lys Phe Val Ile Gly Gly Pro Gln Gly Asp Ala
225                 230                 235                 240

Gly Leu Thr Gly Arg Lys Ile Ile Val Asp Thr Tyr Gly Gly Ser Cys
                245                 250                 255

Pro His Gly Gly Gly Ala Phe Ser Gly Lys Asp Pro Ser Lys Val Asp
            260                 265                 270

Arg Ser Ala Ala Tyr Ala Ala Arg Tyr Val Ala Lys Asn Leu Val Ala
```

```
            275                 280                 285
Ser Gly Val Cys Asp Lys Ala Ile Val Gln Val Ala Tyr Ala Ile Gly
    290                 295                 300

Val Val Glu Pro Val Ser Ile Leu Val Asp Thr Gln Gly Thr Gly Lys
305                 310                 315                 320

Val Glu Asp Ser Lys Leu Thr Glu Cys Val Lys Ala Val Phe Arg Leu
                325                 330                 335

Thr Pro Lys Gly Ile Ile Glu Ser Leu Asp Leu Leu Arg Pro Ile Tyr
            340                 345                 350

Arg Lys Thr Ala Ala Tyr Gly His Phe Gly Arg Glu Leu Asn Glu Phe
        355                 360                 365

Ser Trp Glu Lys Thr Asp Lys Val Glu Ala Ile Lys Asp Phe Cys Gly
    370                 375                 380

Ile Lys
385

<210> SEQ ID NO 120
<211> LENGTH: 422
<212> TYPE: PRT
<213> ORGANISM: Leptospira interrogans

<400> SEQUENCE: 120

Met Phe Glu Arg Asn Ile Val Trp Ile Phe Leu Thr Pro Arg Gln Ser
1               5                   10                  15

Val Gly Phe Trp Asp Gln Ser Gly Thr Ser Pro Leu Ile Phe His Leu
            20                  25                  30

Gln Glu Glu Gln Met Ser Leu Lys Asp Phe Ile Phe Thr Ser Glu Ser
        35                  40                  45

Val Gly Glu Gly His Pro Asp Lys Val Cys Asp Gln Ile Ser Asp Ala
    50                  55                  60

Val Leu Asp Ala Tyr Leu Glu Gln Asp Pro Lys Ser Arg Val Ala Cys
65                  70                  75                  80

Glu Thr Leu Val Thr Thr Asn Leu Val Val Ile Ala Gly Glu Ile Thr
                85                  90                  95

Ser Lys Gly Lys Val Asp Ala Gln Glu Ile Ala Arg Asn Val Ile Arg
            100                 105                 110

Asp Ile Gly Tyr Asn Asp Ile Thr Met Gly Phe Asp Ala Asp Phe Ala
        115                 120                 125

Val Val Ser Ala His Val His Ala Gln Ser Pro Asp Ile Ser Gln Gly
    130                 135                 140

Val Thr Glu Gly Glu Gly Leu Phe Lys Glu Gln Gly Ala Gly Asp Gln
145                 150                 155                 160

Gly Leu Met Phe Gly Phe Ala Ile Asn Glu Thr Pro Glu Leu Met Pro
                165                 170                 175

Met Pro Ile Tyr Tyr Ser His Glu Leu Val Lys His Leu Ala Gly Leu
            180                 185                 190

Arg His Gly Asn Lys Leu Lys Phe Leu Arg Pro Asp Ala Lys Ser Gln
        195                 200                 205

Val Thr Val Glu Tyr Lys Asp Gly Lys Pro Val Arg Ile Asp Thr Val
    210                 215                 220

Val Ile Ser Thr Gln His Ser Pro Asp Val Thr His Lys Gln Ile Glu
225                 230                 235                 240

Glu Ala Leu Ile Glu Glu Cys Ile Lys Lys Val Ile Pro Ala Asn Leu
                245                 250                 255
```

```
Leu Asn Asn Thr Lys Tyr Phe Ile Asn Pro Thr Gly Gln Phe Ile Ile
                260                 265                 270

Gly Gly Pro His Gly Asp Ala Gly Leu Thr Gly Arg Lys Ile Ile Val
            275                 280                 285

Asp Thr Tyr Gly Gly Tyr Gly Arg His Gly Gly Ala Phe Ser Gly
        290                 295                 300

Lys Asp Pro Ser Lys Val Asp Arg Ser Ala Ala Tyr Met Gly Arg Tyr
305                 310                 315                 320

Ile Ala Lys Asn Val Ala Ser Gly Leu Ala Asp Lys Cys Glu Val
                325                 330                 335

Gln Leu Ala Tyr Ala Ile Gly Val Ala Glu Pro Val Ser Val His Val
                340                 345                 350

Asp Thr Phe Gly Thr Gly Lys Ile Ser Glu Glu Glu Leu Val Lys Arg
            355                 360                 365

Ile Arg Ala Asn Phe Lys Leu Thr Pro Arg Gly Ile Ile Glu Ser Leu
        370                 375                 380

Lys Leu Leu Glu Lys Gly Arg Lys Tyr Arg Glu Thr Ala Ser Tyr Gly
385                 390                 395                 400

His Phe Gly Arg Lys Gly Ser Thr Phe Thr Trp Glu Glu Thr Asp Lys
                405                 410                 415

Ala Ser Ala Leu Lys Gly
            420

<210> SEQ ID NO 121
<211> LENGTH: 422
<212> TYPE: PRT
<213> ORGANISM: Leptospira interrogans

<400> SEQUENCE: 121

Met Phe Glu Arg Asn Ile Val Trp Ile Phe Leu Thr Pro Arg Gln Ser
1               5                   10                  15

Val Gly Phe Trp Asp Gln Ser Gly Thr Ser Pro Leu Ile Phe His Leu
            20                  25                  30

Gln Glu Glu Gln Met Ser Leu Lys Asp Phe Ile Phe Thr Ser Glu Ser
        35                  40                  45

Val Gly Glu Gly His Pro Asp Lys Val Cys Asp Gln Ile Ser Asp Ala
    50                  55                  60

Val Leu Asp Ala Tyr Leu Glu Gln Asp Pro Lys Ser Arg Val Ala Cys
65                  70                  75                  80

Glu Thr Leu Val Thr Thr Asn Leu Val Val Ile Ala Gly Glu Ile Thr
                85                  90                  95

Ser Lys Gly Lys Val Asp Ala Gln Glu Ile Ala Arg Asn Val Ile Arg
            100                 105                 110

Asp Ile Gly Tyr Asn Asp Ile Thr Met Gly Phe Asp Ala Asp Phe Ala
        115                 120                 125

Val Val Ser Ala His Val His Ala Gln Ser Pro Asp Ile Ser Gln Gly
    130                 135                 140

Val Thr Glu Gly Glu Gly Leu Phe Lys Glu Gln Gly Ala Gly Asp Gln
145                 150                 155                 160

Gly Leu Met Phe Gly Phe Ala Ile Asn Glu Thr Pro Glu Leu Met Pro
                165                 170                 175

Met Pro Ile Tyr Tyr Ser His Glu Leu Val Lys His Leu Ala Gly Leu
            180                 185                 190

Arg His Gly Asn Lys Leu Lys Phe Leu Arg Pro Asp Ala Lys Ser Gln
        195                 200                 205
```

```
Val Thr Val Glu Tyr Lys Asp Gly Lys Pro Val Arg Ile Asp Thr Val
    210                 215                 220
Val Ile Ser Thr Gln His Ser Pro Asp Val Thr His Lys Gln Ile Glu
225                 230                 235                 240
Glu Ala Leu Ile Glu Glu Cys Ile Lys Lys Val Ile Pro Ala Asn Leu
                245                 250                 255
Leu Asn Asn Thr Lys Tyr Phe Ile Asn Pro Thr Gly Gln Phe Ile Ile
                260                 265                 270
Gly Gly Pro His Gly Asp Ala Gly Leu Thr Gly Arg Lys Ile Ile Val
            275                 280                 285
Asp Thr Tyr Gly Gly Tyr Gly Arg His Gly Gly Ala Phe Ser Gly
            290                 295                 300
Lys Asp Pro Ser Lys Val Asp Arg Ser Ala Ala Tyr Met Gly Arg Tyr
305                 310                 315                 320
Ile Ala Lys Asn Val Val Ala Ser Gly Leu Ala Asp Lys Cys Glu Val
                325                 330                 335
Gln Leu Ala Tyr Ala Ile Gly Val Ala Glu Pro Val Ser Val His Val
            340                 345                 350
Asp Thr Phe Gly Thr Gly Lys Ile Ser Glu Glu Glu Leu Val Lys Arg
            355                 360                 365
Ile Arg Ala Asn Phe Lys Leu Thr Pro Arg Gly Ile Ile Glu Ser Leu
370                 375                 380
Lys Leu Leu Glu Lys Gly Arg Lys Tyr Arg Glu Thr Ala Ser Tyr Gly
385                 390                 395                 400
His Phe Gly Arg Lys Gly Ser Thr Phe Thr Trp Glu Gly Thr Asp Lys
                405                 410                 415
Ala Ser Ala Leu Lys Gly
            420

<210> SEQ ID NO 122
<211> LENGTH: 386
<212> TYPE: PRT
<213> ORGANISM: Leptospira interrogans

<400> SEQUENCE: 122

Met Ser Leu Lys Asp Phe Ile Phe Thr Ser Glu Ser Val Gly Glu Gly
1               5                   10                  15
His Pro Asp Lys Val Cys Asp Gln Ile Ser Asp Ala Val Leu Asp Ala
                20                  25                  30
Tyr Leu Glu Gln Asp Pro Lys Ser Arg Val Ala Cys Glu Thr Leu Val
            35                  40                  45
Thr Thr Asn Leu Val Val Ile Ala Gly Glu Ile Thr Ser Lys Gly Lys
        50                  55                  60
Val Asp Ala Gln Glu Ile Ala Arg Asn Val Ile Arg Asp Ile Gly Tyr
65                  70                  75                  80
Asn Asp Ile Thr Met Gly Phe Asp Ala Asp Phe Ala Val Val Ser Ala
                85                  90                  95
His Val His Ala Gln Ser Pro Asp Ile Ser Gln Gly Val Thr Glu Gly
            100                 105                 110
Glu Gly Leu Phe Lys Glu Gln Gly Ala Gly Asp Gln Gly Leu Met Phe
        115                 120                 125
Gly Phe Ala Ile Asn Glu Thr Pro Glu Leu Met Pro Met Pro Ile Tyr
    130                 135                 140
Tyr Ser His Glu Leu Val Lys His Leu Ala Gly Leu Arg His Gly Asn
```

```
                145                 150                 155                 160
Lys Leu Lys Phe Leu Arg Pro Asp Ala Lys Ser Gln Val Thr Val Glu
                165                 170                 175

Tyr Lys Asp Gly Lys Pro Val Arg Ile Asp Thr Val Val Ile Ser Thr
                180                 185                 190

Gln His Ser Pro Asp Val Thr His Lys Gln Ile Glu Ala Leu Ile
            195                 200                 205

Glu Glu Cys Ile Lys Lys Val Ile Pro Ala Asn Leu Leu Asn Asn Thr
        210                 215                 220

Lys Tyr Phe Ile Asn Pro Thr Gly Gln Phe Ile Ile Gly Gly Pro His
225                 230                 235                 240

Gly Asp Ala Gly Leu Thr Gly Arg Lys Ile Ile Val Asp Thr Tyr Gly
                245                 250                 255

Gly Tyr Gly Arg His Gly Gly Gly Ala Phe Ser Gly Lys Asp Pro Ser
                260                 265                 270

Lys Val Asp Arg Ser Ala Ala Tyr Met Gly Arg Tyr Ile Ala Lys Asn
            275                 280                 285

Val Val Ala Ser Gly Leu Ala Asp Lys Cys Glu Val Gln Leu Ala Tyr
        290                 295                 300

Ala Ile Gly Val Ala Glu Pro Val Ser Val His Val Asp Thr Phe Gly
305                 310                 315                 320

Thr Gly Lys Ile Ser Glu Glu Leu Val Lys Arg Ile Arg Ala Asn
                325                 330                 335

Phe Lys Leu Thr Pro Arg Gly Ile Ile Glu Ser Leu Lys Leu Leu Glu
                340                 345                 350

Lys Gly Arg Lys Tyr Arg Glu Thr Ala Ser Tyr Gly His Phe Gly Arg
            355                 360                 365

Lys Gly Ser Thr Phe Thr Trp Glu Glu Thr Asp Lys Ala Ser Ala Leu
        370                 375                 380

Lys Gly
385

<210> SEQ ID NO 123
<211> LENGTH: 395
<212> TYPE: PRT
<213> ORGANISM: Pirellula sp.

<400> SEQUENCE: 123

Met Ser Asn Glu Ser Gly Arg Phe Leu Phe Thr Ser Glu Ser Val Ser
1               5                   10                  15

Met Gly His Pro Asp Lys Leu Ala Asp Arg Ile Ser Asp Ser Ile Leu
                20                  25                  30

Asp Ala Leu Leu Ala Gln Asp Pro His Ser Arg Val Ala Cys Glu Thr
            35                  40                  45

Leu Val Thr Thr Gly Leu Ala Val Ile Ala Gly Glu Ile Ser Ser Lys
        50                  55                  60

Ala Asp Val Asp Tyr Glu Lys Ile Val Arg Asp Thr Ile Val Ala Val
65                  70                  75                  80

Gly Tyr Asp Asp Pro Asp Ile Gly Ile Asp Gly Lys Thr Cys Glu Val
                85                  90                  95

Gln Ile Arg Leu Asp Ala Gln Ser Pro Asp Ile Ala Gln Gly Val Asn
                100                 105                 110

Ser Asp Glu Ala Ser Gly Lys Asp Ile Gly Ala Gly Asp Gln Gly Leu
            115                 120                 125
```

```
Met Phe Gly Tyr Ala Cys Lys Asp Thr Pro Glu Leu Met Pro Leu Pro
            130                 135                 140

Ile Ala Leu Ser His Arg Ile Ile Asn Arg Ile Thr Glu Ala Arg Phe
145                 150                 155                 160

Asn Lys Glu Val Asp Trp Leu Arg Pro Asp Asn Lys Ser Gln Val Thr
                165                 170                 175

Val Glu Tyr Asp Gly Asn Arg Pro Val Arg Ile Glu Ala Val Val Val
                180                 185                 190

Ser Ala Gln His Gly Pro Asp Val Ser His Asp Glu Ile Glu Lys Phe
                195                 200                 205

Val Ile Glu Asn Val Val Lys Pro Ser Ile Pro Ala Glu Leu Asp Lys
210                 215                 220

Gly Asp Ile Lys Tyr His Ile Asn Pro Thr Gly Lys Phe Ile Ile Gly
225                 230                 235                 240

Gly Pro His Gly Asp Cys Gly Leu Thr Gly Arg Lys Ile Ile Val Asp
                245                 250                 255

Thr Tyr Gly Gly Trp Gly Arg His Gly Gly Gly Ala Phe Ser Gly Lys
                260                 265                 270

Asp Ser Thr Lys Val Asp Arg Ser Ala Ala Tyr Met Ala Arg Tyr Val
                275                 280                 285

Ala Lys Asn Ile Val Ala Ala Gly Leu Ala Glu Arg Cys Glu Val Gln
290                 295                 300

Leu Ala Tyr Ala Ile Gly Val Thr Glu Pro Val Ser Val His Val Asp
305                 310                 315                 320

Thr Glu Gly Thr Gly Lys Ile Glu Asp Ala Lys Leu Cys Glu Leu Ile
                325                 330                 335

Arg Glu His Phe Pro Leu Thr Pro Gly Gly Ile Ile Asp His Leu Gln
                340                 345                 350

Leu Arg Arg Pro Val Phe Val Glu Thr Thr Ala Gly His Phe Gly
                355                 360                 365

Arg Asp Gly Glu Gly Phe Thr Trp Glu Lys Thr Asp Lys Ala Asp Ala
                370                 375                 380

Leu Ala Glu Ala Ala Gly Ala Thr Ala Thr Ala
385                 390                 395

<210> SEQ ID NO 124
<211> LENGTH: 395
<212> TYPE: PRT
<213> ORGANISM: Lactobacillus plantarum

<400> SEQUENCE: 124

Met Ser Glu Arg His Leu Phe Thr Ser Glu Ser Val Ser Glu Gly His
1               5                   10                  15

Pro Asp Lys Ile Ala Asp Gln Ile Ser Asp Ala Ile Leu Asp Ala Met
                20                  25                  30

Leu Ala Gln Asp Pro Gln Ala Arg Val Ala Val Glu Thr Ser Val Thr
            35                  40                  45

Thr Gly Leu Val Leu Val Phe Gly Glu Val Ser Thr Lys Ala Tyr Val
        50                  55                  60

Asp Ile Gln Lys Val Val Arg Asp Thr Ile Lys Ser Ile Gly Tyr Val
65                  70                  75                  80

Asp Gly Gln Tyr Gly Phe Asp Gly Asp Asn Cys Ala Val Leu Val Ser
                85                  90                  95

Leu Asp Glu Gln Ser Pro Asp Ile Ala Gln Gly Val Asp Asp Ser Leu
                100                 105                 110
```

```
Glu Thr Arg Ser Gly Asp Ala Asp Pro Leu Asp Gln Ile Gly Ala Gly
        115                 120                 125

Asp Gln Gly Met Met Phe Gly Tyr Ala Ile Asn Glu Thr Pro Glu Leu
    130                 135                 140

Met Pro Leu Pro Ile Ala Leu Ser His Arg Leu Met Arg Lys Ile Ala
145                 150                 155                 160

Ala Leu Arg Lys Asp Gly Thr Ile Lys Trp Leu Arg Pro Asp Ala Lys
                165                 170                 175

Ala Gln Val Thr Val Glu Tyr Asp Glu Asp Asn Gln Pro Lys Arg Ile
            180                 185                 190

Asp Thr Val Val Leu Ser Thr Gln His Asp Pro Asp Val Asp Leu Asp
        195                 200                 205

Thr Ile Arg Gln Thr Val Ile Asp Gln Val Ile Lys Ala Val Leu Pro
    210                 215                 220

Ala Asp Leu Leu Asp Asp Gln Thr Lys Tyr Leu Val Asn Pro Thr Gly
225                 230                 235                 240

Arg Phe Val Ile Gly Gly Pro Gln Gly Asp Ala Gly Leu Thr Gly Arg
                245                 250                 255

Lys Val Ile Val Asp Thr Tyr Gly Gly Phe Ala His His Gly Gly Gly
            260                 265                 270

Ala Phe Ser Gly Lys Asp Ala Thr Lys Val Asp Arg Ser Ala Ser Tyr
        275                 280                 285

Ala Ala Arg Tyr Ile Ala Lys Asn Val Val Ala Gly Leu Ala Asp
    290                 295                 300

Gln Val Glu Val Gln Leu Ala Tyr Ala Ile Gly Val Ala Glu Pro Val
305                 310                 315                 320

Ser Ile Ala Val Asp Thr Ala Gly Thr Gly Lys Val Ser Asp Glu Ala
                325                 330                 335

Leu Ile Asn Ala Ile Arg Glu Asn Phe Asp Leu Arg Pro Ala Gly Ile
            340                 345                 350

Ile Lys Met Leu Asp Leu Gln Arg Pro Ile Tyr Arg Gln Thr Ala Ala
        355                 360                 365

Tyr Gly His Phe Gly Arg Thr Asp Ile Asp Leu Pro Trp Glu His Thr
    370                 375                 380

Asp Lys Val Asp Ala Leu Lys Ala Val Phe Lys
385                 390                 395

<210> SEQ ID NO 125
<211> LENGTH: 407
<212> TYPE: PRT
<213> ORGANISM: Corynebacterium glutamicum

<400> SEQUENCE: 125

Met Ala Gln Pro Thr Ala Val Arg Leu Phe Thr Ser Glu Ser Val Thr
1               5                   10                  15

Glu Gly His Pro Asp Lys Ile Cys Asp Ala Ile Ser Thr Ile Leu
                20                  25                  30

Asp Ala Leu Leu Glu Lys Asp Pro Gln Ser Arg Val Ala Val Glu Thr
            35                  40                  45

Val Val Thr Thr Gly Ile Val His Val Gly Glu Val Arg Thr Ser
        50                  55                  60

Ala Tyr Val Glu Ile Pro Gln Leu Val Arg Asn Lys Leu Ile Glu Ile
65                  70                  75                  80

Gly Phe Asn Ser Ser Glu Val Gly Phe Asp Gly Arg Thr Cys Gly Val
```

```
                        85                  90                  95
Ser Val Ser Ile Gly Glu Gln Ser Gln Glu Ile Ala Asp Gly Val Asp
                100                 105                 110

Asn Ser Asp Glu Ala Arg Thr Asn Gly Asp Val Glu Glu Asp Asp Arg
                115                 120                 125

Ala Gly Ala Gly Asp Gln Gly Leu Met Phe Gly Tyr Ala Thr Asn Glu
            130                 135                 140

Thr Glu Glu Tyr Met Pro Leu Pro Ile Ala Leu Ala His Arg Leu Ser
145                 150                 155                 160

Arg Arg Leu Thr Gln Val Arg Lys Glu Gly Ile Val Pro His Leu Arg
                165                 170                 175

Pro Asp Gly Lys Thr Gln Val Thr Phe Ala Tyr Asp Ala Gln Asp Arg
                180                 185                 190

Pro Ser His Leu Asp Thr Val Val Ile Ser Thr Gln His Asp Pro Glu
            195                 200                 205

Val Asp Arg Ala Trp Leu Glu Thr Gln Leu Arg Glu His Val Ile Asp
        210                 215                 220

Trp Val Ile Lys Asp Ala Gly Ile Glu Asp Leu Ala Thr Gly Glu Ile
225                 230                 235                 240

Thr Val Leu Ile Asn Pro Ser Gly Ser Phe Ile Leu Gly Gly Pro Met
                245                 250                 255

Gly Asp Ala Gly Leu Thr Gly Arg Lys Ile Ile Val Asp Thr Tyr Gly
            260                 265                 270

Gly Met Ala Arg His Gly Gly Gly Ala Phe Ser Gly Lys Asp Pro Ser
            275                 280                 285

Lys Val Asp Arg Ser Ala Ala Tyr Ala Met Arg Trp Val Ala Lys Asn
        290                 295                 300

Ile Val Ala Ala Gly Leu Ala Asp Arg Ala Glu Val Gln Val Ala Tyr
305                 310                 315                 320

Ala Ile Gly Arg Ala Lys Pro Val Gly Leu Tyr Val Glu Thr Phe Asp
                325                 330                 335

Thr Asn Lys Glu Gly Leu Ser Asp Glu Gln Ile Gln Ala Ala Val Leu
            340                 345                 350

Glu Val Phe Asp Leu Arg Pro Ala Ala Ile Ile Arg Glu Leu Asp Leu
        355                 360                 365

Leu Arg Pro Ile Tyr Ala Asp Thr Ala Ala Tyr Gly His Phe Gly Arg
        370                 375                 380

Thr Asp Leu Asp Leu Pro Trp Glu Ala Ile Asp Arg Val Asp Glu Leu
385                 390                 395                 400

Arg Ala Ala Leu Lys Leu Ala
                405

<210> SEQ ID NO 126
<211> LENGTH: 402
<212> TYPE: PRT
<213> ORGANISM: Streptomyces coelicolor

<400> SEQUENCE: 126

Met Ser Arg Arg Leu Phe Thr Ser Glu Ser Val Thr Glu Gly His Pro
1               5                   10                  15

Asp Lys Ile Ala Asp Gln Ile Ser Asp Thr Ile Leu Asp Ala Leu Leu
                20                  25                  30

Arg Glu Asp Pro Thr Ser Arg Val Ala Val Glu Thr Leu Ile Thr Thr
            35                  40                  45
```

```
Gly Leu Val His Val Ala Gly Glu Val Thr Thr Lys Ala Tyr Ala Asp
    50                  55                  60

Ile Ala Asn Leu Val Arg Gly Lys Ile Leu Glu Ile Gly Tyr Asp Ser
65                  70                  75                  80

Ser Lys Lys Gly Phe Asp Gly Ala Ser Cys Gly Val Ser Val Ser Ile
                85                  90                  95

Gly Ala Gln Ser Pro Asp Ile Ala Gln Gly Val Asp Thr Ala Tyr Glu
            100                 105                 110

Asn Arg Val Glu Gly Asp Glu Asp Leu Asp Arg Gln Gly Ala Gly
            115                 120                 125

Asp Gln Gly Leu Met Phe Gly Tyr Ala Ser Asp Glu Thr Pro Thr Leu
        130                 135                 140

Met Pro Leu Pro Val Phe Leu Ala His Arg Leu Ser Lys Arg Leu Ser
145                 150                 155                 160

Glu Val Arg Lys Asn Gly Thr Ile Pro Tyr Leu Arg Pro Asp Gly Lys
                165                 170                 175

Thr Gln Val Thr Ile Glu Tyr Asp Gly Asp Lys Ala Val Arg Leu Asp
            180                 185                 190

Thr Val Val Val Ser Ser Gln His Ala Ser Asp Ile Asp Leu Glu Ser
        195                 200                 205

Leu Leu Ala Pro Asp Ile Lys Glu Phe Val Val Glu Pro Glu Leu Lys
210                 215                 220

Ala Leu Leu Glu Asp Gly Ile Lys Ile Asp Thr Glu Asn Tyr Arg Leu
225                 230                 235                 240

Leu Val Asn Pro Thr Gly Arg Phe Glu Ile Gly Gly Pro Met Gly Asp
                245                 250                 255

Ala Gly Leu Thr Gly Arg Lys Ile Ile Ile Asp Thr Tyr Gly Gly Met
            260                 265                 270

Ala Arg His Gly Gly Gly Ala Phe Ser Gly Lys Asp Pro Ser Lys Val
        275                 280                 285

Asp Arg Ser Ala Ala Tyr Ala Met Arg Trp Val Ala Lys Asn Val Val
    290                 295                 300

Ala Ala Gly Leu Ala Ala Arg Cys Glu Val Gln Val Ala Tyr Ala Ile
305                 310                 315                 320

Gly Lys Ala Glu Pro Val Gly Leu Phe Val Glu Thr Phe Gly Thr Ala
                325                 330                 335

Lys Val Asp Thr Glu Lys Ile Glu Lys Ala Ile Asp Glu Val Phe Asp
            340                 345                 350

Leu Arg Pro Ala Ala Ile Ile Arg Ala Leu Asp Leu Leu Arg Pro Ile
        355                 360                 365

Tyr Ala Gln Thr Ala Ala Tyr Gly His Phe Gly Arg Glu Leu Pro Asp
    370                 375                 380

Phe Thr Trp Glu Arg Thr Asp Arg Val Asp Ala Leu Arg Glu Ala Ala
385                 390                 395                 400

Gly Leu

<210> SEQ ID NO 127
<211> LENGTH: 406
<212> TYPE: PRT
<213> ORGANISM: Bifidobacterium longum

<400> SEQUENCE: 127

Met Thr Glu Glu His Arg Leu Ile Ser Ala Glu Ser Val Thr Glu Gly
1               5                   10                  15
```

His Pro Asp Lys Val Cys Asp Gln Ile Ser Asp Ala Ile Leu Asp Asp
                 20                  25                  30

Leu Leu Ala Gln Asp Ser Ser His Val Ala Val Glu Thr Ser Ala
         35                  40                  45

Ala Thr Gly Val Phe Leu Val Phe Gly Glu Val Thr Ser Glu Gly Tyr
 50                  55                  60

Cys Asp Val Gln Ser Lys Val Arg Glu Thr Leu Arg Asn Ile Gly Tyr
 65                  70                  75                  80

Thr Ser Ser Glu Val Gly Leu Asp Ala Asp Ser Cys Gly Val Val Val
             85                  90                  95

Ala Ile Thr Glu Gln Ser Ala Glu Ile Asn Gln Gly Val Ala Arg Leu
            100                 105                 110

Thr Gly Asp Gln Glu Thr Ala Ala Ser Arg Glu Glu Arg Tyr Glu Ala
            115                 120                 125

Gln Gly Ala Gly Asp Gln Gly Val Met Phe Gly Tyr Ala Thr Asp Glu
        130                 135                 140

Thr Pro Thr Leu Met Pro Leu Pro Ile Tyr Leu Ala His Arg Leu Ala
145                 150                 155                 160

Phe His Leu Thr Glu Val Arg Lys Ser Gly Glu Val Pro His Leu Arg
                165                 170                 175

Pro Asp Gly Lys Thr Gln Val Thr Ile Glu Tyr Asp Asp Asp Asp Lys
                180                 185                 190

Pro Val Arg Leu Asp Thr Val Leu Ile Ser Thr Gln His Asp Pro Glu
                195                 200                 205

Val Thr Gln Asp Trp Leu Ala Val Glu Leu Lys Lys His Val Ile Asp
210                 215                 220

Pro Val Leu Asp Glu Val Leu Gly Ser Lys Val Pro His Asp Asn Tyr
225                 230                 235                 240

Arg Gln Leu Val Asn Pro Thr Gly Ser Phe Ile Leu Gly Gly Pro Ala
                245                 250                 255

Ala Asp Ala Gly Leu Thr Gly Arg Lys Ile Ile Val Asp Thr Tyr Gly
                260                 265                 270

Gly Ala Ala His His Gly Gly Gly Ala Phe Ser Gly Lys Asp Pro Ser
            275                 280                 285

Lys Val Asp Arg Ser Ala Ala Tyr Ala Thr Arg Trp Val Ala Lys Asn
290                 295                 300

Ile Val Ala Ala Gly Leu Ala His Lys Val Glu Ile Gln Ile Ala Tyr
305                 310                 315                 320

Ala Ile Gly Val Ala Asp Pro Val Ser Val Asn Val Glu Thr Phe Gly
                325                 330                 335

Thr Glu Gln Gly Val Thr Arg Gly Gln Ile Ala Ala Val Arg Lys
            340                 345                 350

Val Phe Asp Leu Arg Pro Ala Ala Ile Ile Asp Glu Leu Asp Leu Lys
        355                 360                 365

Arg Pro Ile Tyr Leu Lys Thr Ala Ala Tyr Gly His Phe Gly Arg Thr
        370                 375                 380

Asp Val Glu Phe Pro Trp Glu Lys Thr Asp Lys Val Glu Glu Leu Lys
385                 390                 395                 400

Ala Ala Ile Ala Ala Glu
                405

<210> SEQ ID NO 128
<211> LENGTH: 419
<212> TYPE: PRT

<213> ORGANISM: Synechococcus sp.

<400> SEQUENCE: 128

```
Met Ser Arg Tyr Val Phe Thr Ser Glu Ser Val Thr Glu Gly His Pro
1               5                   10                  15
Asp Lys Ile Cys Asp Gln Val Ser Asp Ala Val Leu Asp Ala Leu Leu
            20                  25                  30
Ala Gln Asp Pro Ser Ser Arg Val Ala Cys Glu Thr Val Val Asn Thr
        35                  40                  45
Gly Leu Cys Met Ile Thr Gly Glu Val Thr Ser Lys Ala Gln Val Asp
    50                  55                  60
Phe Ile His Leu Val Arg Asn Val Ile Lys Glu Ile Gly Tyr Ser Gly
65                  70                  75                  80
Ala Arg Ala Gly Gly Phe Asp Ala Asn Ser Cys Ala Val Leu Val Ala
                85                  90                  95
Leu Asp Gln Gln Ser Pro Asp Ile Ala Gln Gly Val Asp Glu Ala Asp
            100                 105                 110
Asp His Glu Gly Asp Pro Leu Asp Arg Val Gly Ala Gly Asp Gln Gly
        115                 120                 125
Ile Met Phe Gly Tyr Ala Cys Asn Glu Thr Pro Glu Leu Met Pro Leu
130                 135                 140
Pro Ile Ser Leu Ala His Arg Leu Ala Lys Arg Leu Ala Glu Val Arg
145                 150                 155                 160
His Asn Gly Ser Leu Glu Tyr Leu Leu Pro Asp Gly Lys Thr Gln Val
                165                 170                 175
Ser Val Val Tyr Glu Asn Asp Lys Pro Val Ala Ile Asp Thr Ile Leu
            180                 185                 190
Ile Ser Thr Gln His Thr Ala Glu Val Ala Gly Ile Ser Asp Glu Gln
        195                 200                 205
Gly Ile Arg Glu Arg Ile Thr Glu Asp Leu Trp Thr His Val Val Glu
    210                 215                 220
Pro Ala Thr Ala Asp Leu Ala Leu Lys Pro Ser Arg Glu Ala Thr Lys
225                 230                 235                 240
Tyr Leu Val Asn Pro Thr Gly Lys Phe Val Val Gly Gly Pro Gln Gly
                245                 250                 255
Asp Ala Gly Leu Thr Gly Arg Lys Ile Ile Val Asp Thr Tyr Gly Gly
            260                 265                 270
Tyr Ala Arg His Gly Gly Gly Ala Phe Ser Gly Lys Asp Pro Thr Lys
        275                 280                 285
Val Asp Arg Ser Ala Ala Tyr Ala Ala Arg Tyr Val Ala Lys Cys Leu
    290                 295                 300
Val Ala Ser Gly Leu Ala Glu Arg Ala Glu Val Gln Leu Ser Tyr Ala
305                 310                 315                 320
Ile Gly Val Ala Lys Pro Val Ser Ile Leu Val Glu Ser Phe Gly Thr
                325                 330                 335
Gly Lys Val Ser Asn Ala Glu Leu Thr Glu Leu Val Gln Glu His Phe
            340                 345                 350
Asp Leu Arg Pro Gly Ala Ile Ile Glu Thr Phe Gly Leu Arg Asn Leu
        355                 360                 365
Pro Gln Gln Arg Gly Gly Arg Phe Tyr Gln Asp Thr Ala Ala Tyr Gly
    370                 375                 380
His Phe Gly Arg Asn Asp Leu Lys Ala Pro Trp Glu Asp Val Ala Ala
385                 390                 395                 400
```

```
Lys Ser Glu Glu Leu Val Lys Ala Glu Ala Lys Arg Ile Lys Gln Gly
                405                 410                 415

Ala Thr Val

<210> SEQ ID NO 129
<211> LENGTH: 410
<212> TYPE: PRT
<213> ORGANISM: Prochlorococcus marinus

<400> SEQUENCE: 129

Met Pro Ser Phe Val Phe Thr Ser Glu Ser Val Thr Glu Gly His Pro
1               5                   10                  15

Asp Lys Ile Cys Asp Gln Val Ser Asp Ala Ile Leu Asp Ala Leu Leu
            20                  25                  30

Asp Gln Asp Pro Asn Ser Arg Val Ala Cys Glu Thr Val Val Asn Thr
        35                  40                  45

Gly Leu Cys Leu Ile Thr Gly Glu Val Thr Ser Lys Ala Lys Val Asp
    50                  55                  60

Phe Ile Asn Leu Val Arg Glu Val Ile Lys Glu Ile Gly Tyr Phe Gly
65                  70                  75                  80

Ala Lys Ala Gly Gly Phe Asp Ser Asn Ser Cys Ser Val Leu Val Ala
                85                  90                  95

Leu Asp Gln Gln Ser Pro Asp Ile Ala Gln Gly Val Asp Glu Ala Asp
            100                 105                 110

Asp His Ser Gly Asn Pro Phe Asp Gln Val Gly Ala Gly Asp Gln Gly
        115                 120                 125

Ile Met Phe Gly Phe Ala Cys Asp Glu Thr Pro Glu Leu Met Pro Leu
    130                 135                 140

Pro Ile Ser Leu Ala His Arg Leu Ser Arg Arg Leu Ala Lys Val Arg
145                 150                 155                 160

His Asp Gly Thr Leu Lys Tyr Leu Leu Pro Asp Gly Lys Thr Gln Val
                165                 170                 175

Ser Val Leu Tyr Glu Asn Asn Lys Pro Thr Ala Ile Asp Thr Ile Leu
            180                 185                 190

Ile Ser Thr Gln His Thr Ala Glu Val Glu Gly Ile Thr Ser Glu Lys
        195                 200                 205

Gly Ile Arg Glu Gln Ile Ser Lys Asp Leu Trp Glu Leu Val Val Lys
    210                 215                 220

Pro Ala Thr Glu Asp Leu Pro Ile Lys Pro Ile Gln Glu Lys Thr Arg
225                 230                 235                 240

Phe Leu Val Asn Pro Thr Gly Lys Phe Val Val Gly Pro Gln Gly
                245                 250                 255

Asp Ala Gly Leu Thr Gly Arg Lys Ile Ile Val Asp Thr Tyr Gly Gly
            260                 265                 270

Tyr Ala Arg His Gly Gly Gly Ala Phe Ser Gly Lys Asp Pro Thr Lys
        275                 280                 285

Val Asp Arg Ser Ala Ala Tyr Ala Ala Arg Phe Val Ala Lys Ser Leu
    290                 295                 300

Val Ala Ala Gly Leu Ala Ser Arg Val Glu Val Gln Leu Ser Tyr Ala
305                 310                 315                 320

Ile Gly Val Ala Asn Pro Val Ser Ile Leu Val Glu Ala Phe Gly Ser
                325                 330                 335

Gly Lys Met Ser Asn Glu Ala Leu Thr Glu Leu Val Thr Glu Asn Phe
            340                 345                 350
```

Asp Leu Arg Pro Gly Ala Ile Ile Glu Gln Phe Gly Leu Arg Ser Leu
            355                 360                 365

Pro Asn Gln Arg Gln Gly Arg Phe Tyr Arg Asp Val Ala Ala Tyr Gly
        370                 375                 380

His Phe Gly Arg Pro Asp Leu Asn Leu Pro Trp Glu Asp Val Gln Asp
385                 390                 395                 400

Lys Ala Lys Glu Leu Ile Glu Ser Gln Lys
                405                 410

<210> SEQ ID NO 130
<211> LENGTH: 419
<212> TYPE: PRT
<213> ORGANISM: Gloeobacter violaceus

<400> SEQUENCE: 130

Met Ser Arg Tyr Leu Phe Ser Ser Glu Ser Val Thr Glu Gly His Pro
1               5                   10                  15

Asp Lys Ile Cys Asp Gln Ile Ser Asp Thr Ile Leu Asp Ala Leu Leu
            20                  25                  30

Thr Gln Asp Pro Arg Ser Arg Val Ala Ala Glu Val Val Val Asn Thr
        35                  40                  45

Gly Met Val Val Thr Gly Glu Ile Thr Thr Ala Asn Val Asn
    50                  55                  60

Phe Thr Lys Leu Val Arg Asp Lys Ile Arg Glu Ile Gly Tyr Thr Glu
65                  70                  75                  80

Ala Asp Asn Gly Phe Ser Ala Asp Ser Cys Ala Val Phe Leu Ala Leu
                85                  90                  95

Asp Glu Gln Ser Pro Glu Ile Ala Gln Gly Val Ser Cys Ala Leu Glu
            100                 105                 110

Val Arg Thr Ser Glu Glu Asp Ala Leu Asp Arg Ile Gly Ala Gly Asp
        115                 120                 125

Gln Gly Leu Met Phe Gly Phe Ala Cys Thr Glu Thr Pro Glu Leu Met
    130                 135                 140

Pro Leu Pro Ile Ser Val Ala His Arg Leu Thr Arg Arg Leu Ala Gln
145                 150                 155                 160

Val Arg Lys Asp Gly Thr Leu Ala Tyr Leu Lys Pro Asp Gly Lys Ala
                165                 170                 175

Gln Val Thr Val Glu Tyr Glu Arg Lys Asp Gly Val Asp Arg Pro Gly
            180                 185                 190

Arg Ile Asp Thr Ile Leu Ile Ser Thr Gln His Ala Ala Val Ile Asp
        195                 200                 205

Asp Leu Ser Asp Asn Asp Ala Val Gln Ala Arg Ile Lys Ala Asp Leu
    210                 215                 220

Gln Thr His Val Ile Gly Pro Val Phe Ala Asp Leu Asp Ile Arg Pro
225                 230                 235                 240

Asp Ala Gln Thr Arg Leu Leu Val Asn Pro Ser Gly Arg Phe Val Ile
                245                 250                 255

Gly Gly Pro Gln Gly Asp Ser Gly Leu Thr Gly Arg Lys Ile Ile Val
            260                 265                 270

Asp Thr Tyr Gly Gly Tyr Ala Arg His Gly Gly Gly Ala Phe Ser Gly
        275                 280                 285

Lys Asp Pro Thr Lys Val Asp Arg Ser Ala Ala Tyr Ala Ala Arg Tyr
    290                 295                 300

Val Ala Lys Asn Ile Val Ala Ala Glu Leu Ala Asp Arg Cys Glu Val
305                 310                 315                 320

```
Gln Val Ala Tyr Ala Ile Gly Val Ala Arg Pro Val Ser Ile Phe Val
                325                 330                 335

Glu Thr Phe Gly Thr Gly Arg Val Ser Asp Glu Ala Leu Met Leu Leu
            340                 345                 350

Val Arg Glu His Phe Asp Leu Arg Pro Ala Ala Ile Leu Arg Asp Phe
        355                 360                 365

Asp Leu Cys Arg Leu Pro Ala Gln Arg Gly Gly Arg Phe Tyr Gln Asp
    370                 375                 380

Val Ala Ala Tyr Gly His Leu Gly Arg Pro Asp Leu Asp Leu Pro Trp
385                 390                 395                 400

Glu His Thr Asp Lys Ala Ala Thr Leu Lys Gln Ala Ile Gln Thr Ala
                405                 410                 415

Ala Ala Val

<210> SEQ ID NO 131
<211> LENGTH: 398
<212> TYPE: PRT
<213> ORGANISM: Rhodopseudomonas palustris

<400> SEQUENCE: 131

Met Arg Ala Ser Tyr Met Phe Thr Ser Glu Ser Val Ser Glu Gly His
1               5                   10                  15

Pro Asp Lys Val Cys Asp Arg Ile Ser Asp Glu Ile Val Asp Leu Phe
            20                  25                  30

Tyr Arg Glu Gly Pro Lys Ala Gly Ile Asp Pro Trp Ala Ile Arg Ala
        35                  40                  45

Ala Cys Glu Thr Leu Ala Thr Thr Asn Lys Val Val Ile Ala Gly Glu
    50                  55                  60

Thr Arg Gly Pro Ala Ser Val Thr Asn Glu Gln Ile Glu Gln Val Val
65                  70                  75                  80

Arg Asp Ala Ile Lys Asp Ile Gly Tyr Glu Gln Glu Gly Phe His Trp
                85                  90                  95

Lys Thr Ala Asp Ile Glu Ile Leu Leu His Pro Gln Ser Ala Asp Ile
            100                 105                 110

Ala Gln Gly Val Asp Ala Leu Gln Pro Gly Thr Asn Lys Glu Glu Gly
        115                 120                 125

Ala Gly Asp Gln Gly Ile Met Phe Gly Tyr Ala Thr Asn Glu Thr Pro
    130                 135                 140

Asp Leu Met Pro Ala Pro Ile Phe Tyr Ala His Lys Ile Leu Arg Leu
145                 150                 155                 160

Ile Ser Glu Ala Arg His Ser Gly Lys Glu Lys Val Leu Gly Pro Asp
                165                 170                 175

Ser Lys Ser Gln Val Thr Ile Gln Tyr Glu Asn Gly Lys Pro Gln Tyr
            180                 185                 190

Val Arg Glu Ile Val Ser His Gln His Leu Ile Glu Asp Leu Ser
        195                 200                 205

Ser Asn Gln Ile Arg Asp Cys Val Glu Pro Tyr Val Arg Gln Ala Leu
    210                 215                 220

Pro Asp Gly Trp Ile Thr Asp Asn Thr Ile Trp His Ile Asn Pro Thr
225                 230                 235                 240

Gly Lys Phe Tyr Ile Gly Gly Pro Asp Gly Asp Thr Gly Leu Thr Gly
                245                 250                 255

Arg Lys Ile Ile Val Asp Thr Tyr Gly Gly Ala Ala Pro His Gly Gly
            260                 265                 270
```

```
Gly Ala Phe Ser Gly Lys Asp Pro Thr Lys Val Asp Arg Ser Ala Ala
        275                 280                 285

Tyr Ala Ala Arg Tyr Leu Ala Lys Asn Val Val Ala Ser Gly Leu Ala
        290                 295                 300

Asp Lys Cys Thr Leu Gln Leu Ala Tyr Ala Ile Gly Val Ala Arg Pro
305                 310                 315                 320

Leu Ser Ile Tyr Ile Asp Thr His Gly Thr Gly Lys Val Ser Glu Asp
                325                 330                 335

Lys Leu Glu Thr Ile Val Ala Glu Val Met Asp Leu Thr Pro Arg Gly
                340                 345                 350

Ile Arg Thr His Leu Asp Leu Asn Lys Pro Ile Tyr Ala Arg Thr Ser
                355                 360                 365

Ser Tyr Gly His Phe Gly Arg Thr Pro Asp Ala Asp Gly Gly Phe Ser
        370                 375                 380

Trp Glu Lys Thr Asp Leu Ala Asp Ala Met Lys Arg Ala Val
385                 390                 395

<210> SEQ ID NO 132
<211> LENGTH: 398
<212> TYPE: PRT
<213> ORGANISM: Rhodopseudomonas palustris

<400> SEQUENCE: 132

Met Arg Ala Ser Tyr Met Phe Thr Ser Glu Ser Val Ser Glu Gly His
1               5                   10                  15

Pro Asp Lys Val Cys Asp Arg Ile Ser Asp Glu Ile Val Asp Leu Phe
                20                  25                  30

Tyr Arg Glu Gly Pro Lys Ala Gly Ile Asp Pro Trp Ala Ile Arg Ala
            35                  40                  45

Ala Cys Glu Thr Leu Ala Thr Thr Asn Lys Val Val Ile Ala Gly Glu
        50                  55                  60

Thr Arg Gly Pro Ala Ser Val Thr Asn Glu Gln Ile Glu Gln Val Val
65                  70                  75                  80

Arg Asp Ala Ile Lys Asp Ile Gly Tyr Glu Gln Glu Gly Phe His Trp
                85                  90                  95

Lys Thr Ala Asp Ile Glu Ile Leu Leu His Pro Gln Ser Ala Asp Ile
                100                 105                 110

Ala Gln Gly Val Asp Ala Leu Gln Pro Gly Thr Asn Lys Glu Glu Gly
            115                 120                 125

Ala Gly Asp Gln Gly Ile Met Phe Gly Tyr Ala Thr Asn Glu Thr Pro
        130                 135                 140

Asp Leu Met Pro Ala Pro Ile Phe Tyr Ala His Lys Ile Leu Arg Leu
145                 150                 155                 160

Ile Ser Glu Ala Arg His Ser Gly Lys Glu Lys Val Leu Gly Pro Asp
                165                 170                 175

Ser Lys Ser Gln Val Thr Ile Gly Tyr Glu Asn Gly Lys Pro Gln Tyr
            180                 185                 190

Val Arg Glu Ile Val Val Ser His Gln His Leu Ile Glu Asp Leu Ser
        195                 200                 205

Ser Asn Gln Ile Arg Asp Cys Val Glu Pro Tyr Val Arg Gln Ala Leu
    210                 215                 220

Pro Asp Gly Trp Ile Thr Asp Asn Thr Ile Trp His Ile Asn Pro Thr
225                 230                 235                 240

Gly Lys Phe Tyr Ile Gly Gly Pro Asp Gly Asp Thr Gly Leu Thr Gly
```

```
                    245                 250                 255
Arg Lys Ile Ile Val Asp Thr Tyr Gly Gly Ala Ala Pro His Gly Gly
            260                 265                 270

Gly Ala Phe Ser Gly Lys Asp Pro Thr Lys Val Asp Arg Ser Ala Ala
            275                 280                 285

Tyr Ala Ala Arg Tyr Leu Ala Lys Asn Val Val Ala Ser Gly Leu Ala
            290                 295                 300

Asp Lys Cys Thr Leu Gln Leu Ala Tyr Ala Ile Gly Val Ala Arg Pro
305                 310                 315                 320

Leu Ser Ile Tyr Ile Asp Thr His Gly Thr Gly Lys Val Ser Glu Asp
            325                 330                 335

Lys Leu Glu Thr Ile Val Ala Glu Val Met Asp Leu Thr Pro Arg Gly
            340                 345                 350

Ile Arg Thr His Leu Asp Leu Asn Lys Pro Ile Tyr Ala Arg Thr Ser
            355                 360                 365

Ser Tyr Gly His Phe Gly Arg Thr Pro Asp Ala Asp Gly Gly Phe Ser
            370                 375                 380

Trp Glu Lys Thr Asp Leu Ala Asp Ala Met Lys Arg Ala Val
385                 390                 395

<210> SEQ ID NO 133
<211> LENGTH: 429
<212> TYPE: PRT
<213> ORGANISM: Porphyromonas gingivalis

<400> SEQUENCE: 133

Met Ser Tyr Leu Phe Thr Ser Glu Ser Val Ser Glu Gly His Pro Asp
1               5                   10                  15

Lys Val Ser Asp Gln Ile Ser Asp Ala Ile Leu Asp Gln Phe Leu Ala
            20                  25                  30

Thr Asp Pro Asp Ser Lys Val Ala Cys Glu Thr Leu Val Thr Thr Gly
            35                  40                  45

Gln Val Val Leu Ala Gly Glu Val Lys Ser Arg Ser Tyr Val Asp Val
        50                  55                  60

Gln Glu Thr Ala Arg Arg Val Ile Glu Arg Ile Gly Tyr Thr Lys Ser
65                  70                  75                  80

Glu Tyr Gly Phe Asp Thr Arg Ser Cys Gly Ile Phe Ser Ser Ile His
                85                  90                  95

Glu Gln Ser Ala Asp Ile Asn Arg Gly Val Asp Arg Ser Asp Arg Ser
            100                 105                 110

Glu Gln Gly Ala Gly Asp Gln Gly Met Met Phe Gly Tyr Ala Thr Asn
            115                 120                 125

Glu Thr Glu Asn Tyr Met Pro Leu Thr Val Asp Leu Ala His His Leu
        130                 135                 140

Leu Tyr Glu Leu Ala Ala Ile Arg Lys Glu Pro Ser Ser Pro Met Pro
145                 150                 155                 160

Tyr Leu Arg Pro Asp Ala Lys Ser Gln Val Thr Ile Glu His Asp Asp
                165                 170                 175

Glu Gly Arg Pro Val Arg Ile Asp Thr Ile Val Ile Ser Thr Gln His
            180                 185                 190

Asp Glu Phe Val Gln Ala Ser Asp Gly Ile Ser Glu Ala Glu Ala Asp
            195                 200                 205

Arg Met Met Gln Glu Arg Ile His His Asp Ile Ala Thr Ile Leu Ile
        210                 215                 220
```

```
Pro Arg Val Lys Met Leu Tyr Lys Pro Glu Ile Ala Ala Leu Phe Asp
225                 230                 235                 240

Glu Lys Val Arg Leu Phe Val Asn Pro Thr Gly Lys Phe Val Ile Gly
            245                 250                 255

Gly Pro His Gly Asp Thr Gly Leu Thr Gly Arg Lys Ile Ile Val Asp
        260                 265                 270

Thr Tyr Gly Gly Arg Ala Ser His Gly Gly Ala Phe Ser Gly Lys
    275                 280                 285

Asp Pro Ser Lys Val Asp Arg Ser Ala Ala Tyr Ala Arg His Ile
290                 295                 300

Ala Lys Asn Met Val Ala Ala Gly Val Ala Asp Glu Met Leu Val Gln
305                 310                 315                 320

Val Ala Tyr Ala Ile Gly Val Ala Glu Pro Val Ser Ile Tyr Val Asn
                325                 330                 335

Thr Lys Gly Arg Ser His Val Ala Leu Ser Asp Gly Gln Ile Ala Glu
                340                 345                 350

Lys Ile Lys Lys Ile Phe Asp Met Arg Pro Tyr Ala Ile Glu Gln Arg
            355                 360                 365

Leu Lys Leu Arg Asn Pro Ile Tyr Glu Glu Thr Ala Ala Tyr Gly His
370                 375                 380

Phe Gly Arg Glu Pro Tyr Glu Ala Tyr Lys Thr Phe Val Asp Glu His
385                 390                 395                 400

Gly Thr Glu Gln Met Arg Ile Val Glu Leu Phe Thr Trp Glu Lys Leu
                405                 410                 415

Asp Tyr Val Asp Lys Ile Arg Ala Glu Phe Gly Leu Ser
            420                 425

<210> SEQ ID NO 134
<211> LENGTH: 341
<212> TYPE: PRT
<213> ORGANISM: Clostridium perfringens

<400> SEQUENCE: 134

Met Val Met Gly Glu Ile Thr Thr Asn Cys Tyr Val Asp Ile Pro Lys
1               5                   10                  15

Ile Ala Arg Glu Thr Ile Lys Asn Ile Gly Tyr Asp Arg Ala Lys Tyr
                20                  25                  30

Gly Phe Asp Cys Glu Thr Cys Ser Val Met Thr Thr Ile Asp Glu Gln
            35                  40                  45

Ser Ser Asp Ile Ala Met Gly Val Asp Glu Ala Leu Glu Ser Arg Ala
50                  55                  60

Gly Glu Lys Ile Asp Ile Asp Ala Val Gly Ala Asp Gln Gly Met
65                  70                  75                  80

Met Phe Gly Phe Ala Thr Asn Glu Thr Glu Glu Phe Met Pro Ala Pro
                85                  90                  95

Ile Ala Met Ala His Arg Leu Ser Arg Arg Leu Thr Glu Val Arg Lys
                100                 105                 110

Asn Gly Thr Leu Pro Tyr Leu Arg Pro Asp Gly Lys Thr Gln Val Thr
            115                 120                 125

Val Glu Tyr Glu Asn Asp Lys Pro Val Arg Ile Asp Ala Ile Val Ile
130                 135                 140

Ser Thr Gln His Gly Pro Glu Val Ser Gln Glu Gln Ile Gln Ala Asp
145                 150                 155                 160

Leu Met Glu His Val Ile Lys Ala Val Ile Pro Ala Glu Leu Leu Asp
                165                 170                 175
```

```
Glu Asn Thr Lys Tyr Tyr Ile Asn Pro Thr Gly Arg Phe Val Ile Gly
            180                 185                 190

Gly Pro Gln Gly Asp Ala Gly Leu Thr Gly Arg Lys Ile Ile Val Asp
        195                 200                 205

Thr Tyr Gly Gly Tyr Gly Arg His Gly Gly Gly Ala Phe Ser Gly Lys
    210                 215                 220

Asp Pro Thr Lys Val Asp Arg Ser Ala Ala Tyr Ala Ala Arg Trp Val
225                 230                 235                 240

Ala Lys Asn Leu Val Ala Gly Ile Ala Asp Lys Leu Glu Val Gln
            245                 250                 255

Val Ala Tyr Ala Ile Gly Val Ala Lys Pro Val Ser Ile Ile Val Asp
            260                 265                 270

Thr Phe Gly Thr Gly Lys Ile Ser Asp Glu Glu Ile Val Asn Ile Ile
        275                 280                 285

Asn Lys Val Phe Asp Leu Arg Pro Gly Ala Ile Ile Arg Asp Leu Asp
        290                 295                 300

Leu Arg Arg Pro Ile Tyr Arg Gln Thr Ala Ala Tyr Gly His Phe Gly
305                 310                 315                 320

Arg Thr Asp Leu Asp Leu Pro Trp Glu Asn Leu Asn Lys Val Glu Glu
                325                 330                 335

Ile Lys Lys Tyr Leu
            340

<210> SEQ ID NO 135
<211> LENGTH: 378
<212> TYPE: PRT
<213> ORGANISM: Mycoplasma penetrans

<400> SEQUENCE: 135

Met Glu Leu Arg Lys Ile Met Thr Ser Glu Ser Val Gly Lys Gly His
1               5                   10                  15

Pro Asp Lys Ile Cys Asp Gln Ile Ser Asp Ala Val Leu Asp Glu Cys
            20                  25                  30

Leu Lys Gln Asp Pro Asn Ser Lys Val Ala Cys Glu Val Phe Ala Ala
        35                  40                  45

Asn Arg Leu Ile Val Ile Gly Gly Glu Ile Thr Thr Ala Gly Tyr Val
    50                  55                  60

Asp Val Val Lys Met Ala Trp Asn Val Leu Ile Pro Leu Gly Tyr Asp
65                  70                  75                  80

Glu Ser Asp Phe Thr Ile Ile Ser Asn Val Asn Ser Gln Ser Asn Glu
                85                  90                  95

Ile Phe Asn Ala Val Glu Lys Asp Asn Gln Ile Gly Ala Gly Asp Gln
            100                 105                 110

Gly Val Val Tyr Gly Tyr Ala Thr Asp Glu Cys Glu Asn Phe Met Pro
        115                 120                 125

Leu Pro Ile Asn Ile Ala His Asp Leu Val Lys Cys Ala Glu Gln Val
    130                 135                 140

Ile Trp Asn Thr Lys Ile Asp Phe Ile Lys His Asp Met Lys Ser Gln
145                 150                 155                 160

Val Thr Ile Asp Tyr Ala Asp Ser Gln Asn Pro Lys Ile Asp Gln Ile
                165                 170                 175

Ile Met Ser Val Gln His Ser Gln Asn Ala Thr Lys Glu Ser Ile Glu
            180                 185                 190

Ser Phe Cys Asn Ala Ile Ile Asp Phe Val Val Lys Lys Tyr Asn Leu
```

```
                195                 200                 205
Asn Ser Asp Phe Lys Arg Ile Ile Asn Ser Gly Lys Phe Thr Ile
    210                 215                 220
Gly Gly Pro Ile Gly Asp Thr Gly Leu Thr Gly Arg Lys Leu Met Val
225                 230                 235                 240
Asp Thr Tyr Gly Ser Leu Ala Lys His Gly Gly Ala Phe Ser Gly
                245                 250                 255
Lys Asp Cys Thr Lys Val Asp Arg Ser Gly Ala Tyr Phe Ala Arg Tyr
                260                 265                 270
Ile Ala Lys Asn Ile Val Ala Ala Lys Leu Ala Lys Lys Cys Glu Val
                275                 280                 285
Gln Leu Ser Phe Ala Ile Gly Ala Ser Lys Pro Ile Ala Phe Ala Val
    290                 295                 300
Asp Thr Phe Gly Thr Ser Lys Tyr Ser Asp Glu Gln Ile Tyr Glu Ile
305                 310                 315                 320
Ile Val Asn Thr Phe Asp Phe Ser Ile Lys Ser Phe Ile Glu Lys Phe
                325                 330                 335
Asn Met Arg Ser Pro Ile Tyr Ser Pro Phe Ser Thr Tyr Gly His Phe
                340                 345                 350
Gly Arg Thr Glu Leu Asn Pro Gly Trp Glu Gln Leu Asp Lys Val Glu
                355                 360                 365
Glu Ile Leu Glu Phe Thr Lys Lys Tyr Asn
    370                 375

<210> SEQ ID NO 136
<211> LENGTH: 398
<212> TYPE: PRT
<213> ORGANISM: Campylobacter jejuni

<400> SEQUENCE: 136

Met Tyr Leu Phe Thr Ser Glu Val Val Ser Ala Gly His Pro Asp Lys
1               5                   10                  15
Cys Ala Asp Ile Ile Ala Asp Thr Ile Val Asp Ile Leu Leu Lys Asn
                20                  25                  30
Asp Lys Asn Ser Arg Val Ala Ser Glu Val Phe Val Ala Gly Asn Lys
            35                  40                  45
Val Val Ile Gly Gly Glu Val Lys Ser Asn His Lys Leu Ser Lys Ala
        50                  55                  60
Asp Tyr Asp Asn Leu Val Lys Asp Val Leu Lys Asn Ile Gly Tyr Asp
65                  70                  75                  80
Gly Ala Gly His Phe Ser Lys Glu Gln Cys Leu His Pro Asp Glu Val
                85                  90                  95
Asp Val Met Val Phe Leu Asn Gln Ser Pro Asp Ile Asn Gln Gly
                100                 105                 110
Val Asp Gln Glu Asp Gly Glu Thr Gly Ala Gly Asp Gln Gly Ile Met
            115                 120                 125
Phe Gly Phe Ala Ser Cys Glu Ala Glu Tyr Met Pro Ala Ala Ile
    130                 135                 140
Ser Tyr Ala Arg Met Leu Cys Asp Arg Val Tyr Ala Tyr Ala Lys Ala
145                 150                 155                 160
Asn Pro His Glu Leu Gly Val Asp Ile Lys Thr Gln Val Thr Ile Asp
                165                 170                 175
Tyr Gly Thr Lys Ala Asn Phe Glu Asn Cys Lys Pro Gln Ser Ile His
                180                 185                 190
```

```
Thr Ile Val Val Ser Ala Pro Cys Val Glu Ser Met Lys Ile Glu Asp
            195                 200                 205

Leu Arg Ser Leu Val Met Lys Leu Ile Leu Asp Ser Asn Leu Pro Lys
210                 215                 220

Glu Leu Phe Asp Pro Asn Lys Thr Arg Ile Leu Ile Asn Pro Thr Gly
225                 230                 235                 240

Lys Tyr Val Asn His Ser Ser Leu His Asp Ser Gly Leu Thr Gly Arg
                245                 250                 255

Lys Leu Ile Val Asp Ser Phe Gly Gly Tyr Ser Pro Ile Gly Gly Gly
                260                 265                 270

Ala Gln Ser Ser Lys Asp Tyr Thr Lys Val Asp Arg Ser Gly Leu Tyr
                275                 280                 285

Ala Gly Arg Trp Leu Ala Lys Asn Ile Val Ala Ala Gly Leu Ala Lys
            290                 295                 300

Lys Cys Ile Val Gln Leu Ser Tyr Ala Ile Gly Val Ala Lys Pro Thr
305                 310                 315                 320

Ser Val Ser Val Asp Cys Met Gly Thr Asn Thr Ser Val Asn Asp Asp
                325                 330                 335

Val Leu Ser Asp Phe Val Met Gln Asn Phe Ser Leu Thr Pro Asn Trp
                340                 345                 350

Ile Arg Asp Lys Phe His Leu Asp Lys Pro Ser Lys Glu Thr Phe Leu
            355                 360                 365

Tyr Ala Asp Val Ala Ala Arg Gly Gln Val Gly Gln Lys Asp Tyr Pro
370                 375                 380

Trp Glu Lys Leu Asp Ala Leu Glu Gln Phe Lys Lys Leu Leu
385                 390                 395

<210> SEQ ID NO 137
<211> LENGTH: 384
<212> TYPE: PRT
<213> ORGANISM: Escherichia coli
<220> FEATURE:
<221> NAME/KEY: MOD_RES
<222> LOCATION: (60)..(60)
<223> OTHER INFORMATION: Ser or Asn
<220> FEATURE:
<221> NAME/KEY: MOD_RES
<222> LOCATION: (90)..(90)
<223> OTHER INFORMATION: Cys or Ala
<220> FEATURE:
<221> NAME/KEY: MOD_RES
<222> LOCATION: (106)..(106)
<223> OTHER INFORMATION: Gly or Ser
<220> FEATURE:
<221> NAME/KEY: MOD_RES
<222> LOCATION: (116)..(116)
<223> OTHER INFORMATION: Gly or Ser
<220> FEATURE:
<221> NAME/KEY: MOD_RES
<222> LOCATION: (138)..(138)
<223> OTHER INFORMATION: Pro or Leu
<220> FEATURE:
<221> NAME/KEY: MOD_RES
<222> LOCATION: (143)..(143)
<223> OTHER INFORMATION: His or Tyr
<220> FEATURE:
<221> NAME/KEY: MOD_RES
<222> LOCATION: (162)..(162)
<223> OTHER INFORMATION: Arg or Cys
<220> FEATURE:
<221> NAME/KEY: MOD_RES
<222> LOCATION: (185)..(185)
<223> OTHER INFORMATION: Val or Asp
<220> FEATURE:
<221> NAME/KEY: MOD_RES
<222> LOCATION: (190)..(190)
```

```
<223> OTHER INFORMATION: His or Tyr
<220> FEATURE:
<221> NAME/KEY: MOD_RES
<222> LOCATION: (228)..(228)
<223> OTHER INFORMATION: Thr or Ile
<220> FEATURE:
<221> NAME/KEY: MOD_RES
<222> LOCATION: (236)..(236)
<223> OTHER INFORMATION: Pro or Ser
<220> FEATURE:
<221> NAME/KEY: MOD_RES
<222> LOCATION: (240)..(240)
<223> OTHER INFORMATION: Cys or Ala
<220> FEATURE:
<221> NAME/KEY: MOD_RES
<222> LOCATION: (254)..(254)
<223> OTHER INFORMATION: Gly or Asp
<220> FEATURE:
<221> NAME/KEY: MOD_RES
<222> LOCATION: (274)..(274)
<223> OTHER INFORMATION: Ser or Phe
<220> FEATURE:
<221> NAME/KEY: MOD_RES
<222> LOCATION: (303)..(303)
<223> OTHER INFORMATION: Ile or Leu
<220> FEATURE:
<221> NAME/KEY: MOD_RES
<222> LOCATION: (379)..(379)
<223> OTHER INFORMATION: Asp or Ala
<220> FEATURE:
<221> NAME/KEY: MOD_RES
<222> LOCATION: (380)..(380)
<223> OTHER INFORMATION: Ala or Met
<220> FEATURE:
<221> NAME/KEY: MOD_RES
<222> LOCATION: (381)..(381)
<223> OTHER INFORMATION: Ala or Leu
<220> FEATURE:
<221> NAME/KEY: MOD_RES
<222> LOCATION: (382)..(382)
<223> OTHER INFORMATION: Gly or Pro
<220> FEATURE:
<221> NAME/KEY: MOD_RES
<222> LOCATION: (383)..(383)
<223> OTHER INFORMATION: Leu or Val

<400> SEQUENCE: 137

Met Ala Lys His Leu Phe Thr Ser Glu Ser Val Ser Glu Gly His Pro
1               5                   10                  15

Asp Lys Ile Ala Asp Gln Ile Ser Asp Ala Val Leu Asp Ala Ile Leu
            20                  25                  30

Glu Gln Asp Pro Lys Ala Arg Val Ala Cys Glu Thr Tyr Val Lys Thr
        35                  40                  45

Gly Met Val Leu Val Gly Gly Glu Ile Thr Thr Xaa Ala Trp Val Asp
50                  55                  60

Ile Glu Glu Ile Thr Arg Asn Thr Val Arg Glu Ile Gly Tyr Val His
65                  70                  75                  80

Ser Asp Met Gly Phe Asp Ala Asn Ser Xaa Ala Val Leu Ser Ala Ile
                85                  90                  95

Gly Lys Gln Ser Pro Asp Ile Asn Gln Xaa Val Asp Arg Ala Asp Pro
            100                 105                 110

Leu Glu Gln Xaa Ala Gly Asp Gln Gly Leu Met Phe Gly Tyr Ala Thr
        115                 120                 125

Asn Glu Thr Asp Val Leu Met Pro Ala Xaa Ile Thr Tyr Ala Xaa Arg
    130                 135                 140

Leu Val Gln Arg Gln Ala Glu Val Arg Lys Asn Gly Thr Leu Pro Trp
145                 150                 155                 160

Leu Xaa Pro Asp Ala Lys Ser Gln Val Thr Phe Gln Tyr Asp Asp Gly
```

```
                   165                 170                 175
Lys Ile Val Gly Ile Asp Ala Val Xaa Leu Ser Thr Gln Xaa Ser Glu
                180                 185                 190

Glu Ile Asp Gln Lys Ser Leu Gln Glu Ala Val Met Glu Glu Ile Ile
                195                 200                 205

Lys Pro Ile Leu Pro Ala Glu Trp Leu Thr Ser Ala Thr Lys Phe Phe
        210                 215                 220

Ile Asn Pro Xaa Gly Arg Phe Val Ile Gly Gly Xaa Met Gly Asp Xaa
225                 230                 235                 240

Gly Leu Thr Gly Arg Lys Ile Ile Val Asp Thr Tyr Gly Xaa Met Ala
                245                 250                 255

Arg His Gly Gly Gly Ala Phe Ser Gly Lys Asp Pro Ser Lys Val Asp
                260                 265                 270

Arg Xaa Ala Ala Tyr Ala Ala Arg Tyr Val Ala Lys Asn Ile Val Ala
        275                 280                 285

Ala Gly Leu Ala Asp Arg Cys Glu Ile Gln Val Ser Tyr Ala Xaa Gly
        290                 295                 300

Val Ala Glu Pro Thr Ser Ile Met Val Glu Thr Phe Gly Thr Glu Lys
305                 310                 315                 320

Val Pro Ser Glu Gln Leu Thr Leu Leu Val Arg Glu Phe Phe Asp Leu
                325                 330                 335

Arg Pro Tyr Gly Leu Ile Gln Met Leu Asp Leu Leu His Pro Ile Tyr
                340                 345                 350

Lys Glu Thr Ala Ala Tyr Gly His Phe Gly Arg Glu His Phe Pro Trp
                355                 360                 365

Glu Lys Thr Asp Lys Ala Gln Leu Leu Arg Xaa Xaa Xaa Xaa Xaa Lys
        370                 375                 380

<210> SEQ ID NO 138
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 138
gcaaattttc tggttatctt cagctatctg gatgtctaaa cgtataagcg tatgtagtga    60
ggtaatcagg ttatgccgat tcgtgtgccg gacgagc                            97
```